(12) United States Patent
Grant et al.

(10) Patent No.: US 9,737,286 B2
(45) Date of Patent: *Aug. 22, 2017

(54) IMPLANTS AND METHODS FOR PERCUTANEOUS PERFORATION CLOSURE

(71) Applicant: VIVASURE MEDICAL LIMITED, Dangan, Galway (IE)

(72) Inventors: Peter Grant, Dangan (IE); Christopher Martin, Oughterard (IE); Michael Dunning, Athlone (IE); Damien Ryan, Galway (IE); Joseph Dolphin, Ballinasloe (IE); Micheál Hession, Claremorris (IE); Bartosz Pawlikowski, Moycullen (IE); Mark McGoldrick, Athlone (IE); Ger Brett, Claregalway (IE); Michael McCartin, Craughwell (IE); Des Regan, Loughrea (IE); Matthew Murphy, Whiterock Hill (IE)

(73) Assignee: Vivasure Medical Limited, Dangan, Parkmore Business Park West, Galway (IE)

( * ) Notice: Subject to any disclaimer, the term of this patent is extended or adjusted under 35 U.S.C. 154(b) by 328 days.

This patent is subject to a terminal disclaimer.

(21) Appl. No.: 13/781,628

(22) Filed: Feb. 28, 2013

(65) Prior Publication Data

US 2014/0018846 A1    Jan. 16, 2014

Related U.S. Application Data

(60) Provisional application No. 61/605,093, filed on Feb. 29, 2012, provisional application No. 61/716,345, filed on Oct. 19, 2012.

(51) Int. Cl.
*A61B 17/00* (2006.01)
*A61B 50/33* (2016.01)
(Continued)

(52) U.S. Cl.
CPC .......... *A61B 17/0057* (2013.01); *A61B 50/33* (2016.02); *A61B 2017/00004* (2013.01);
(Continued)

(58) Field of Classification Search
CPC .......... A61B 17/12022; A61B 17/0057; A61B 2017/00575; A61B 2017/00579;
(Continued)

(56) References Cited

U.S. PATENT DOCUMENTS

| 321,721 A | 7/1885 | Hassan |
|---|---|---|
| 2,001,638 A | 5/1935 | Tornsjo |

(Continued)

FOREIGN PATENT DOCUMENTS

| DE | 102010048908 A1 | 4/2012 |
|---|---|---|
| EP | 0761250 A1 | 3/1997 |

(Continued)

OTHER PUBLICATIONS

U.S. Appl. No. 62/092,212, McGoldrick et al.
(Continued)

*Primary Examiner* — Dianne Dornbusch
(74) *Attorney, Agent, or Firm* — Choate, Hall & Stewart LLP; William R. Haulbrook; Su Kyung Suh

(57) ABSTRACT

A device for sealing an aperture in a tissue includes: a foot including a distal portion configured to be disposed distal to the tissue when the device is implanted in a position to seal the aperture; and a flexible wing positionable against a distal surface of the tissue adjacent the aperture such that the flexible wing is disposed between the distal portion of the foot and the distal surface adjacent the aperture.

34 Claims, 79 Drawing Sheets

(51) Int. Cl.
*A61B 17/22* (2006.01)
*A61B 50/30* (2016.01)
*A61B 90/00* (2016.01)

(52) U.S. Cl.
CPC ............... *A61B 2017/0053* (2013.01); *A61B 2017/00336* (2013.01); *A61B 2017/00367* (2013.01); *A61B 2017/00477* (2013.01); *A61B 2017/00597* (2013.01); *A61B 2017/00623* (2013.01); *A61B 2017/00654* (2013.01); *A61B 2017/00659* (2013.01); *A61B 2017/00862* (2013.01); *A61B 2017/22038* (2013.01); *A61B 2050/314* (2016.02); *A61B 2090/036* (2016.02); *A61B 2090/037* (2016.02)

(58) Field of Classification Search
CPC  A61B 2017/00584; A61B 2017/00588; A61B 2017/00592; A61B 2017/00601; A61B 2017/00606; A61B 2017/0061; A61B 2017/00615; A61B 2017/00619; A61B 2017/00623; A61B 2017/00628; A61B 2017/00632; A61B 2017/00637; A61B 2017/00641; A61B 2017/1205; A61B 2017/12054; A61B 2017/12086; A61B 2017/12095; A61B 2017/00477
See application file for complete search history.

(56) References Cited

U.S. PATENT DOCUMENTS

| | | | |
|---|---|---|---|
| 2,560,162 | A | 7/1951 | Ferguson |
| 2,778,254 | A | 1/1957 | Carapellotti |
| 3,874,388 | A | 4/1975 | King et al. |
| 4,299,230 | A | 11/1981 | Kubota |
| 4,583,540 | A | 4/1986 | Malmin |
| 4,650,472 | A | 3/1987 | Bates |
| 4,705,040 | A | 11/1987 | Mueller et al. |
| 4,744,364 | A | 5/1988 | Kensey |
| 4,852,568 | A | 8/1989 | Kensey |
| 4,890,612 | A | 1/1990 | Kensey |
| 4,896,668 | A | 1/1990 | Popoff et al. |
| 5,021,059 | A | 6/1991 | Kensey et al. |
| 5,037,433 | A | 8/1991 | Wilk et al. |
| 5,053,046 | A | 10/1991 | Janese |
| 5,085,661 | A | 2/1992 | Moss |
| 5,127,412 | A | 7/1992 | Cosmetto et al. |
| 5,171,258 | A | 12/1992 | Bales et al. |
| 5,192,301 | A * | 3/1993 | Kamiya ............ A61B 17/0057 604/907 |
| 5,269,804 | A | 12/1993 | Bales et al. |
| 5,282,827 | A | 2/1994 | Kensey et al. |
| 5,330,488 | A | 7/1994 | Goldrath |
| 5,336,231 | A | 8/1994 | Adair |
| 5,342,393 | A * | 8/1994 | Stack ............... A61B 17/0057 24/453 |
| 5,350,399 | A | 9/1994 | Erlebacher et al. |
| 5,366,480 | A | 11/1994 | Corriveau et al. |
| 5,391,182 | A | 2/1995 | Chin |
| 5,431,639 | A | 7/1995 | Shaw |
| 5,462,560 | A | 10/1995 | Stevens |
| 5,470,337 | A | 11/1995 | Moss |
| 5,501,691 | A | 3/1996 | Goldrath |
| 5,501,700 | A | 3/1996 | Hirata |
| 5,507,755 | A | 4/1996 | Gresl et al. |
| 5,527,322 | A | 6/1996 | Klein et al. |
| 5,531,759 | A | 7/1996 | Kensey et al. |
| 5,545,178 | A | 8/1996 | Kensey et al. |
| 5,549,633 | A | 8/1996 | Evans et al. |
| 5,593,422 | A | 1/1997 | Muijs Van de Moer et al. |
| 5,601,557 | A | 2/1997 | Hayhurst |
| 5,601,571 | A | 2/1997 | Moss |
| 5,620,461 | A * | 4/1997 | Muijs Van De Moer ............ A61B 17/0057 606/213 |
| 5,653,716 | A | 8/1997 | Malo et al. |
| 5,662,681 | A | 9/1997 | Nash et al. |
| 5,665,096 | A | 9/1997 | Yoon |
| 5,676,689 | A | 10/1997 | Kensey et al. |
| 5,690,674 | A | 11/1997 | Diaz |
| 5,700,273 | A | 12/1997 | Buelna et al. |
| 5,700,277 | A * | 12/1997 | Nash ............... A61B 17/0057 128/887 |
| 5,707,393 | A | 1/1998 | Kensey et al. |
| 5,722,981 | A | 3/1998 | Stevens |
| 5,755,727 | A | 5/1998 | Kontos |
| 5,782,861 | A | 7/1998 | Cragg et al. |
| 5,797,939 | A | 8/1998 | Yoon |
| 5,814,065 | A | 9/1998 | Diaz |
| 5,817,074 | A | 10/1998 | Racz |
| 5,827,281 | A | 10/1998 | Levin |
| 5,860,990 | A | 1/1999 | Nobles et al. |
| 5,861,003 | A * | 1/1999 | Latson ............. A61B 17/0057 606/157 |
| 5,868,762 | A | 2/1999 | Cragg et al. |
| 5,916,236 | A | 6/1999 | Muijs Van de Moer et al. |
| 5,935,147 | A | 8/1999 | Kensey et al. |
| 5,941,899 | A | 8/1999 | Granger et al. |
| 5,954,732 | A | 9/1999 | Hart et al. |
| 5,997,515 | A | 12/1999 | de la Torre et al. |
| 6,007,563 | A | 12/1999 | Nash et al. |
| 6,033,427 | A | 3/2000 | Lee |
| 6,056,768 | A | 5/2000 | Cates et al. |
| 6,080,183 | A | 6/2000 | Tsugita et al. |
| 6,126,675 | A * | 10/2000 | Shchervinsky .... A61B 17/0057 606/213 |
| 6,136,010 | A | 10/2000 | Modesitt et al. |
| 6,179,863 | B1 | 1/2001 | Kensey et al. |
| 6,190,400 | B1 | 2/2001 | Van De Moer et al. |
| 6,200,328 | B1 | 3/2001 | Cragg et al. |
| 6,206,895 | B1 | 3/2001 | Levinson |
| 6,241,768 | B1 * | 6/2001 | Agarwal .............. A61F 2/0063 606/151 |
| 6,245,080 | B1 | 6/2001 | Levinson |
| 6,296,658 | B1 | 10/2001 | Gershony et al. |
| 6,319,263 | B1 | 11/2001 | Levinson |
| 6,350,274 | B1 | 2/2002 | Li |
| 6,375,671 | B1 | 4/2002 | Kobayashi et al. |
| 6,383,208 | B1 | 5/2002 | Sancoff et al. |
| 6,395,015 | B1 | 5/2002 | Borst et al. |
| 6,398,796 | B2 | 6/2002 | Levinson |
| 6,425,911 | B1 | 7/2002 | Akerfeldt et al. |
| 6,461,364 | B1 | 10/2002 | Ginn et al. |
| 6,485,481 | B1 | 11/2002 | Pfeiffer |
| 6,500,184 | B1 | 12/2002 | Chan et al. |
| 6,508,828 | B1 | 1/2003 | Akerfeldt et al. |
| 6,520,951 | B1 | 2/2003 | Carrillo, Jr. et al. |
| 6,596,012 | B2 | 7/2003 | Akerfeldt et al. |
| 6,596,014 | B2 | 7/2003 | Levinson et al. |
| 6,596,915 | B1 | 7/2003 | Satyapal et al. |
| 6,638,286 | B1 | 10/2003 | Burbank et al. |
| 6,669,707 | B1 | 12/2003 | Swanstrom et al. |
| 6,669,735 | B1 | 12/2003 | Pelissier |
| 6,702,835 | B2 | 3/2004 | Ginn |
| 6,730,112 | B2 | 5/2004 | Levinson |
| 6,764,500 | B1 | 7/2004 | Muijs Van De Moer et al. |
| 6,770,070 | B1 | 8/2004 | Balbierz |
| 6,779,701 | B2 | 8/2004 | Bailly et al. |
| 6,786,915 | B2 | 9/2004 | Akerfeldt et al. |
| 6,860,895 | B1 * | 3/2005 | Akerfeldt ........... A61B 17/0057 606/139 |
| 6,890,342 | B2 | 5/2005 | Zhu et al. |
| 6,932,824 | B1 | 8/2005 | Roop et al. |
| 6,939,363 | B2 | 9/2005 | Akerfeldt |
| 6,942,674 | B2 | 9/2005 | Belef et al. |
| 6,949,107 | B2 | 9/2005 | McGuckin, Jr. et al. |
| 6,949,114 | B2 | 9/2005 | Milo et al. |
| 6,964,668 | B2 | 11/2005 | Modesitt et al. |
| 6,969,397 | B2 | 11/2005 | Ginn |
| 6,984,219 | B2 | 1/2006 | Ashby et al. |
| 6,989,022 | B2 | 1/2006 | Nowakowski |
| 6,997,940 | B2 | 2/2006 | Bonutti |
| 7,001,398 | B2 | 2/2006 | Carley et al. |
| 7,001,400 | B1 | 2/2006 | Modesitt et al. |

(56) References Cited

U.S. PATENT DOCUMENTS

| | | | |
|---|---|---|---|
| 7,008,440 B2 | 3/2006 | Sing et al. | |
| 7,008,441 B2 | 3/2006 | Zucker | |
| 7,008,442 B2 | 3/2006 | Brightbill | |
| 7,094,248 B2 | 8/2006 | Bachinski et al. | |
| 7,169,168 B2 | 1/2007 | Muijs Van De Moer et al. | |
| 7,326,221 B2 | 2/2008 | Sakamoto et al. | |
| 7,462,188 B2 | 12/2008 | McIntosh | |
| 7,534,248 B2 | 5/2009 | Mikkaichi et al. | |
| 7,569,063 B2 | 8/2009 | Bailly et al. | |
| 7,662,161 B2 | 2/2010 | Briganti et al. | |
| 7,678,133 B2 | 3/2010 | Modesitt | |
| 7,753,935 B2 | 7/2010 | Brett et al. | |
| 7,846,180 B2 | 12/2010 | Cerier | |
| 7,918,868 B2 | 4/2011 | Marshall et al. | |
| 7,998,169 B2 | 8/2011 | Modesitt | |
| 8,002,791 B2 | 8/2011 | Modesitt | |
| 8,002,792 B2 | 8/2011 | Modesitt | |
| 8,002,793 B2 | 8/2011 | Modesitt | |
| 8,012,168 B2 | 9/2011 | Modesitt | |
| 8,083,767 B2 | 12/2011 | Modesitt | |
| 8,137,380 B2 * | 3/2012 | Green | A61B 17/0057 606/151 |
| 8,177,795 B2 | 5/2012 | Niese et al. | |
| 8,241,325 B2 | 8/2012 | Modesitt | |
| 8,267,942 B2 | 9/2012 | Szabo et al. | |
| 8,361,092 B1 * | 1/2013 | Asfora | A61B 17/08 606/153 |
| 8,597,324 B2 | 12/2013 | Briganti et al. | |
| 8,652,166 B2 | 2/2014 | Åkerfeldt | |
| 8,821,507 B2 | 9/2014 | Axelson, Jr. et al. | |
| 8,906,050 B2 | 12/2014 | Brett et al. | |
| 9,060,751 B2 | 6/2015 | Martin et al. | |
| 2001/0044631 A1 * | 11/2001 | Akin | A61B 17/11 606/153 |
| 2002/0019648 A1 | 2/2002 | Akerfeldt et al. | |
| 2002/0019649 A1 | 2/2002 | Sikora et al. | |
| 2002/0055767 A1 * | 5/2002 | Forde | A61B 17/0057 623/1.11 |
| 2002/0107506 A1 | 8/2002 | McGuckin et al. | |
| 2002/0169377 A1 | 11/2002 | Khairkhahan et al. | |
| 2002/0177864 A1 | 11/2002 | Camrud | |
| 2003/0050665 A1 | 3/2003 | Ginn | |
| 2003/0060846 A1 | 3/2003 | Egnelov et al. | |
| 2003/0078598 A1 | 4/2003 | Ginn et al. | |
| 2003/0093093 A1 | 5/2003 | Modesitt et al. | |
| 2003/0120305 A1 | 6/2003 | Jud et al. | |
| 2003/0144695 A1 | 7/2003 | McGuckin et al. | |
| 2003/0216756 A1 | 11/2003 | Klein et al. | |
| 2004/0082906 A1 | 4/2004 | Tallarida et al. | |
| 2004/0092964 A1 | 5/2004 | Modesitt et al. | |
| 2004/0092969 A1 | 5/2004 | Kumar | |
| 2004/0093025 A1 | 5/2004 | Egnelov | |
| 2004/0098044 A1 * | 5/2004 | Van de Moer | A61B 17/0057 606/213 |
| 2004/0133238 A1 | 7/2004 | Cerier | |
| 2004/0176798 A1 | 9/2004 | Epstein et al. | |
| 2004/0243122 A1 | 12/2004 | Auth et al. | |
| 2005/0021055 A1 | 1/2005 | Toubia et al. | |
| 2005/0033326 A1 | 2/2005 | Briganti et al. | |
| 2005/0070957 A1 * | 3/2005 | Das | A61B 17/0057 606/213 |
| 2005/0149065 A1 | 7/2005 | Modesitt | |
| 2005/0209613 A1 | 9/2005 | Roop et al. | |
| 2005/0251201 A1 | 11/2005 | Roue et al. | |
| 2005/0267520 A1 | 12/2005 | Modesitt | |
| 2005/0273135 A1 * | 12/2005 | Chanduszko | A61B 17/0057 606/213 |
| 2005/0288706 A1 | 12/2005 | Widomski et al. | |
| 2006/0100665 A1 | 5/2006 | Von Oepen et al. | |
| 2006/0106418 A1 * | 5/2006 | Seibold | A61B 17/0057 606/213 |
| 2006/0142784 A1 | 6/2006 | Kontos | |
| 2006/0142797 A1 | 6/2006 | Egnelov | |
| 2006/0265008 A1 * | 11/2006 | Maruyama | A61B 17/0057 606/232 |
| 2006/0287673 A1 | 12/2006 | Brett et al. | |
| 2007/0112385 A1 | 5/2007 | Conlon | |
| 2007/0135826 A1 | 6/2007 | Zaver et al. | |
| 2007/0179509 A1 | 8/2007 | Nagata et al. | |
| 2007/0179527 A1 * | 8/2007 | Eskuri | A61B 17/0057 606/213 |
| 2007/0197858 A1 * | 8/2007 | Goldfarb | A61B 17/0401 600/37 |
| 2007/0255313 A1 | 11/2007 | Modesitt | |
| 2007/0282351 A1 | 12/2007 | Harada et al. | |
| 2007/0282373 A1 | 12/2007 | Ashby et al. | |
| 2008/0109017 A1 | 5/2008 | Herweck et al. | |
| 2008/0228204 A1 | 9/2008 | Hamilton et al. | |
| 2008/0243148 A1 | 10/2008 | Mikkaichi et al. | |
| 2008/0312646 A9 | 12/2008 | Auth et al. | |
| 2009/0012521 A1 | 1/2009 | Axelson, Jr. et al. | |
| 2009/0018574 A1 | 1/2009 | Martin | |
| 2009/0048559 A1 | 2/2009 | Grathwohl | |
| 2009/0088723 A1 | 4/2009 | Khosravi et al. | |
| 2009/0112257 A1 * | 4/2009 | Preinitz | A61B 17/0057 606/215 |
| 2009/0143815 A1 | 6/2009 | Eidenschink et al. | |
| 2009/0143821 A1 | 6/2009 | Stupak | |
| 2009/0312786 A1 | 12/2009 | Trask et al. | |
| 2010/0022823 A1 * | 1/2010 | Goldfarb | A61B 17/0401 600/37 |
| 2010/0094425 A1 | 4/2010 | Bentley et al. | |
| 2010/0125296 A1 | 5/2010 | Modesitt | |
| 2010/0152772 A1 | 6/2010 | Brett et al. | |
| 2010/0222796 A1 | 9/2010 | Brett et al. | |
| 2010/0228184 A1 | 9/2010 | Mavani et al. | |
| 2010/0292717 A1 | 11/2010 | Petter-Puchner et al. | |
| 2011/0077667 A1 | 3/2011 | Singhatat et al. | |
| 2011/0082495 A1 * | 4/2011 | Ruiz | A61B 17/0057 606/213 |
| 2011/0087270 A1 | 4/2011 | Penner et al. | |
| 2011/0224728 A1 | 9/2011 | Martin et al. | |
| 2011/0270284 A1 | 11/2011 | Beauchamp et al. | |
| 2012/0089166 A1 | 4/2012 | Modesitt | |
| 2012/0226308 A1 | 9/2012 | Martin et al. | |
| 2012/0226309 A1 | 9/2012 | Jonsson | |
| 2012/0296275 A1 | 11/2012 | Martin et al. | |
| 2013/0218125 A1 | 8/2013 | Stopek et al. | |
| 2013/0274795 A1 | 10/2013 | Grant et al. | |
| 2014/0018847 A1 | 1/2014 | Grant et al. | |
| 2014/0194926 A1 | 7/2014 | Bailly et al. | |
| 2014/0345109 A1 | 11/2014 | Grant et al. | |
| 2016/0051239 A1 | 2/2016 | Martin et al. | |

FOREIGN PATENT DOCUMENTS

| | | |
|---|---|---|
| EP | 0894475 A1 | 2/1999 |
| EP | 2260770 A2 | 12/2010 |
| WO | WO-94/08513 A1 | 4/1994 |
| WO | WO-00/33744 A1 | 6/2000 |
| WO | WO-02/102236 A2 | 12/2002 |
| WO | WO-2004/012601 A2 | 2/2004 |
| WO | WO-2004/012627 A1 | 2/2004 |
| WO | WO-2006/117766 A2 | 11/2006 |
| WO | WO-2007/011353 A2 | 1/2007 |
| WO | WO-2008/042229 A2 | 4/2008 |
| WO | WO-2008/152617 A2 | 12/2008 |
| WO | WO-2009/149455 A1 | 12/2009 |
| WO | WO-2010/027693 A2 | 3/2010 |
| WO | WO-2010/123821 A1 | 10/2010 |
| WO | WO-2011/080588 A2 | 7/2011 |
| WO | WO-2012/090069 A2 | 7/2012 |
| WO | WO-2012/156819 A2 | 11/2012 |
| WO | WO-2013/007534 A1 | 1/2013 |
| WO | WO-2013/128292 A2 | 9/2013 |

(56) References Cited

FOREIGN PATENT DOCUMENTS

| WO | WO-2013/188351 A2 | 12/2013 |
|----|-------------------|---------|
| WO | WO-2014/141209 A1 | 9/2014  |

OTHER PUBLICATIONS

U.S. Appl. No. 62/092,235, Grant et al.
U.S. Appl. No. 62/092,240, Grant et al.
Grant et al., Hales' 1733 Haemastaticks, Anesthesiology, 112:1:65 (2010).
Hales, Stephen, Statical Essays, vol. 2 (1773).
International Preliminary Report on Patentability for PCT/IB2010/003461 dated Jul. 12, 2012, published on Dec. 1, 2011.
International Preliminary Report on Patentability in PCT/IE2006/000043, mailed on Oct. 30, 2007.
International Search Report for PCT/IB2010/003461 dated Oct. 11, 2011, published on Dec. 1, 2011.
International Search Report for PCT/IB2011/003295 Jun. 29, 2012.
International Search Report for PCT/IB2013/000839, dated Jan. 14, 2014, published as WO 2013/128292 (6 pages).
International Search Report, PCT/IB2014/059848, 5 pages, Jul. 7, 2014.
Supplementary Partial European Search Report, Application No. EP 11852355.4, Sep. 28, 2015, 7 pages.
Written Opinion for PCT/IB2011/003295, Jun. 29, 2012.
Written Opinion for PCT/IB2013/000839, dated Jan. 14, 2014, published as WO 2013/128292 (11 pages).
Written Opinion of the International Searching Authority in PCT/IE2006/000043, mailed on Oct. 29, 2007.
Written Opinion of the ISA for PCT/IB2010/003461 dated Oct. 11, 2011, published on Dec. 1, 2011.
Written Opinion, PCT/IB2014/059848, 8 pages (Jul. 7, 2014).

\* cited by examiner

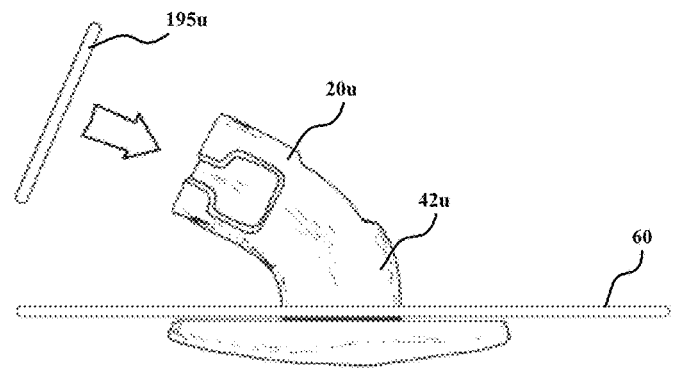
FIG. 17A
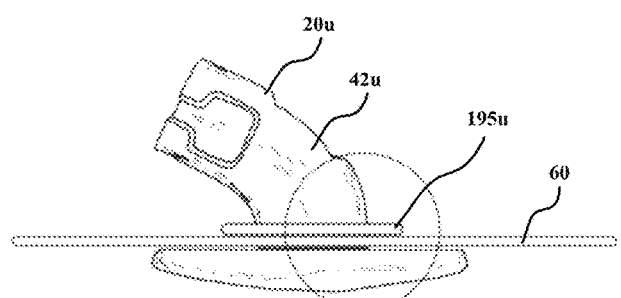 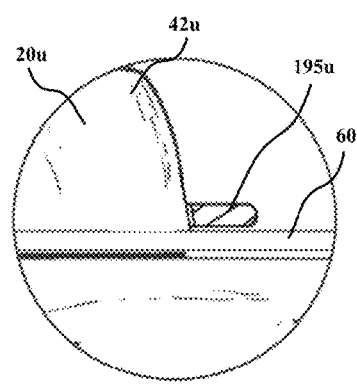
FIG. 17B FIG. 17C

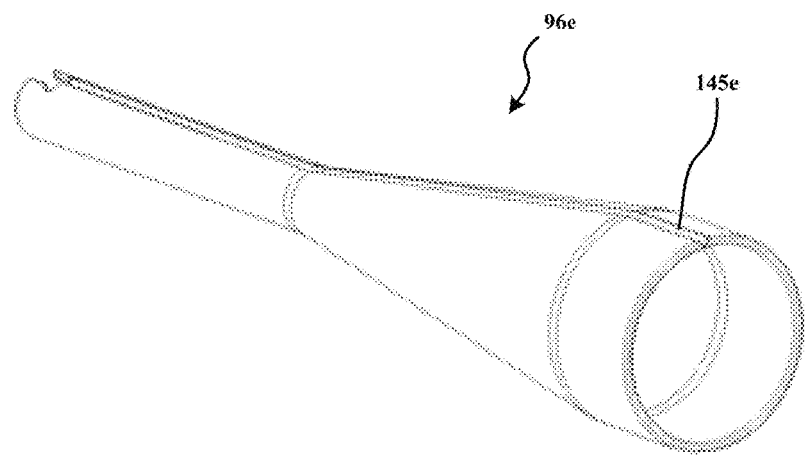
FIG. 43B
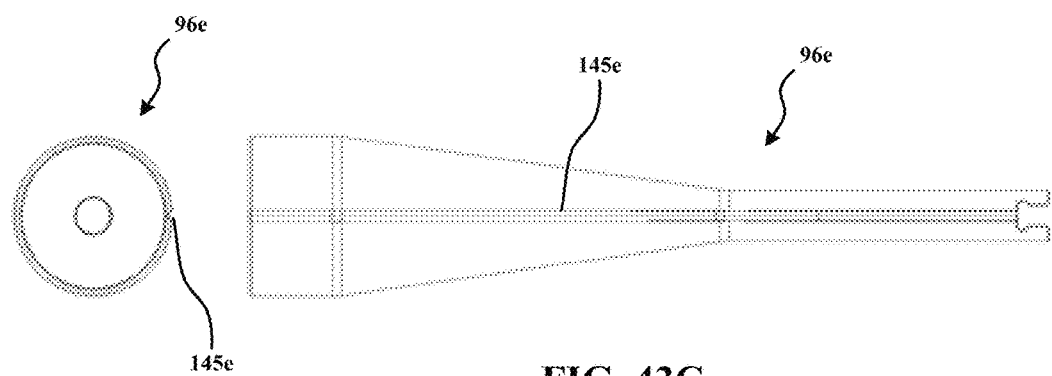
FIG. 43D   FIG. 43C

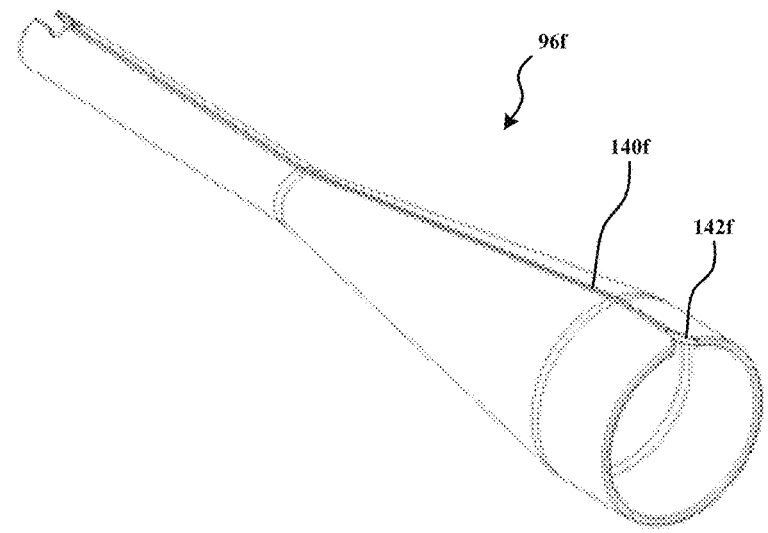
FIG. 43E
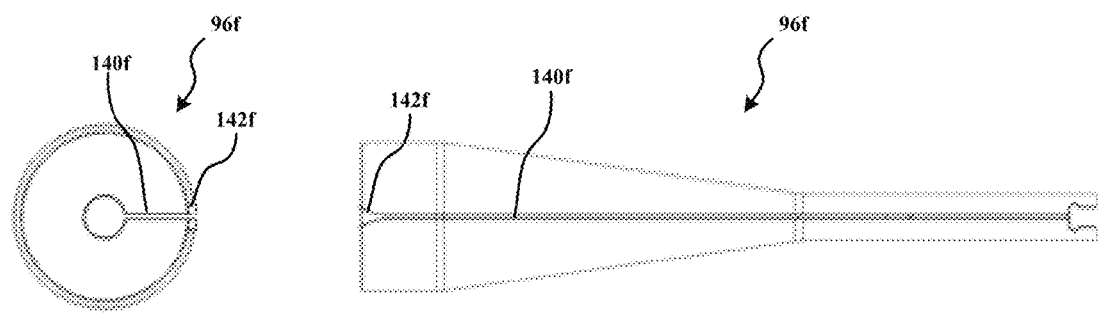
FIG. 43G
FIG. 43F

IMPLANTS AND METHODS FOR PERCUTANEOUS PERFORATION CLOSURE

CROSS-REFERENCE TO RELATED APPLICATIONS

This application claims the benefit of U.S. Provisional Patent Application Ser. No. 61/605,093, filed Feb. 29, 2012, the entire content of which is hereby incorporated by reference, and U.S. Provisional Patent Application Ser. No. 61/716,345, filed Oct. 19, 2012, the entire content of which is hereby incorporated by reference.

Further, each of the following is incorporated herein in its entirety by reference: U.S. patent application Ser. No. 13/781,625, filed Feb. 28, 2013; U.S. patent application Ser. No. 13/781,630, filed Feb. 28, 2013; and PCT Application No. PCT/US13/28451, filed Feb. 28, 2013.

TECHNICAL FIELD

The present invention relates generally to closure systems, devices, and methods for use in surgical procedures.

BACKGROUND

Minimally invasive procedures are continually increasing in number and variation in part because such techniques offer an immediate advantage over more traditional, yet highly invasive surgeries. Endoscopic surgery, for example, uses one or more scopes inserted through small incisions for diagnosing and treating disease. In particular, endovascular surgery gives access to many regions of the body, such as the heart, through major blood vessels. Typically, the technique involves introducing a surgical instrument percutaneously into a blood vessel, such as, for example, the femoral artery. The currently emerging percutaneous endovascular procedures include aortic valve replacement, mitral valve repair, abdominal and thoracic aneurysm repair and tricuspid valve replacement. Other procedures requiring access to the femoral artery include coronary, carotid and cerebral angiographic procedures.

Other examples of a minimally invasive procedure include NOTES (Natural Orifice Translumenal Endoscopic Surgery) based surgery, e.g. transgastric, transvesical, and transcolonic approaches.

A key feature of these minimally invasive surgical procedures is the forming of a temporary pathway, usually an incision or dilated perforation, to the surgical site. For example, in the emerging percutaneous endovascular procedures, an access site (e.g. incision, puncture hole, or perforation) ranging from approximately 10 to 30 French units is formed as a temporary pathway to access the target site. Various instruments, such as procedural sheaths, guidewires and catheters, are inserted through the access site, as well as specialized medical instruments, such as, balloon catheters and stents.

Currently, these large (10 to 30 French (F)) puncture holes (or perforations) or access sites are routinely created after surgical cut down to the blood vessel and post procedure are closed via cut-down surgical repair. This method is very invasive and fraught with complications. Accordingly, the rapid development of percutaneous endovascular surgery, of which interventional radiology and cardiology are a major component, has led to the need for instrumentation to minimize the risk of complications associated with closing the access site after a procedure.

SUMMARY

In accordance with example embodiments, a device for sealing an aperture in a tissue includes: a foot including a distal portion configured to be disposed distally beyond a distal surface of the tissue when the device is in a sealing position, and a proximal portion configured to extend proximally through the aperture and proximally beyond a proximal surface of the tissue when the device is in the sealing position; a flexible wing positionable against the distal surface of the tissue adjacent the aperture such that the flexible wing is disposed between the anterior distal portion of the foot and the distal surface of the tissue when the device is in the sealing position; and an elongated retention member supported by the proximal portion of the foot, the retention member moveable with respect to the proximal portion from a first position to a second position such that a portion of the tissue is disposed between the retention member and the flexible wing when the device is in the sealing position.

The device may be configured to seal a surgical perforation in a cavity such as a gastrointestinal tract, heart, peritoneal cavity, esophagus, vagina, rectum, trachea, bronchi, or a blood vessel.

The device may be configured to seal a surgical perforation in an artery, the flexible wing being positionable against an internal luminal surface of the artery adjacent to the surgical perforation.

The foot may be configured to provide support to the tissue in regions of the distal surface that surround the aperture.

The distal portion of the foot may have an elongated shape.

The device may be configured to seal a surgical perforation having a diameter that is less than a length of the distal portion of the foot.

The distal portion of the foot may have two opposed lateral projections that extend outwardly from the longitudinal axis of the elongated shape.

The lateral projections may be rounded.

The foot may have a transverse width measured from an outer edge of one of the lateral projections to an outer edge of the other lateral projection that is constant along at least a portion of the lateral projections.

The distal portion of the foot may be rectangular.

The distal portion of the foot may be circular.

The device may include a recessed surface disposed in the distal portion of the foot and into which the device flexible portion is received and crimped to provide an effective fluid seal between the wing and the distal portion of the foot.

The device crimping of the flexible wing may be achieved using (a) mechanical (b) chemical, and (c) chemical methods. In some examples, the crimping may be achieved using at least one of (a) mechanical crimping, (b) chemical crimping, and (c) thermal crimping.

The device may further include a passageway extending through at least one of the foot and the flexible wing and configured to receive a guidewire there through, such that the entire device is freely movable along the guidewire.

The device may further include a closure member configured to move from a first position to a second position after complete removal of the guidewire, the movement of the closure member from the first position to the second position causing the passageway to be sealed.

The closure member may be part of the retention member.

The passageway may include an enlarged portion configured to maintain a seal via coagulation.

The enlarged portion may be tapered.

At least one of the foot, the flexible wing, and the retention member may be formed at least in part of a material having an inherent viscosity in a range from 0.5 to 7.0 dl/g.

A longitudinal axis of the proximal portion of the foot may be flexible with respect to a longitudinal axis of the distal portion of the foot.

A longitudinal axis of the proximal portion of the foot may form an angle in a range from 10 to 70 degrees with respect to a longitudinal axis of the distal portion of the foot.

A longitudinal axis of the proximal portion of the foot may form an angle of 30 degrees with respect to a proximal surface of the distal portion of the foot.

The distal portion of the foot may have a length this is greater than a diameter of the aperture.

The proximal portion may be flexible relative to the distal portion of the foot.

The distal portion of the foot may be configured to reinforce the flexible wing to facilitate sealing of the aperture.

The elongated retention member may be configured to provide a safety mechanism against the foot being fully pushed or pulled distally through the aperture.

The device may further include a guide channel configured to receive a guide wire.

The retention member may be configured to block the guide channel when the pin is in the second position.

The pin may be configured to leave the guide channel open when the pin is the second position.

In accordance with example embodiments, a device for sealing an aperture in a tissue includes: a foot including a distal portion configured to be disposed distally beyond a distal surface of the tissue when the device is in a sealing position; and a flexible wing positionable against the distal surface of the tissue and adjacent the aperture such that the flexible wing is disposed between the distal portion of the foot and the distal surface of the tissue when the device is in the sealing position, wherein the foot and wing are configured to be introduced through the aperture over a guidewire.

The device may be configured to seal a surgical perforation in an artery, the flexible wing being positionable against an internal luminal surface of the artery adjacent to the surgical perforation.

In accordance with example embodiments of the present invention, a device includes: a flexible wing positionable against a distal surface of a tissue adjacent an aperture in the tissue, the flexible wing having (a) an anterior surface configured to face the distal surface when the wing is positioned against the distal surface of the tissue and (b) a posterior surface configured to face away from the distal surface of the tissue when the wing is positioned against the distal surface of the tissue, wherein at least one surface of the flexible wing has a wettability that is increased from a base state of a material from which the flexible wing is formed.

The flexible wing may be configured to seal a surgical perforation in an artery, the flexible wing being positionable against an internal luminal surface of the artery adjacent the surgical perforation.

The increased wettability may be provided by at least one of (a) providing an electrical charge to at least one of the anterior surface and the posterior surface; (b) providing a surface texture to at least one of the anterior surface and the posterior surface; (c) attaching a protein to at least one of the anterior surface and the posterior surface; (d) applying a drug coating to at least one of the anterior surface and the posterior surface; and (e) etching at least one of the anterior surface and the posterior surface.

The increased wettability may be provided by grooves formed in at least one of the anterior surface and the posterior surface.

The grooves may have a depth that is in a range from 1 μm to 100 μm.

The grooves may have a depth that is in a range from 7 μm to 40 μm.

In accordance with example embodiments, a method includes: increasing a wettability of an implant configured to seal an aperture in a tissue and including (i) an anterior surface configured to contact the tissue at one or more locations adjacent to the aperture and (ii) a posterior surface, the wettability being increased by at least one of (a) providing an electrical charge to at least one of the anterior surface and the posterior surface; (b) providing a surface texture to at least one of the anterior surface and the posterior surface; (c) attaching a protein to at least one of the anterior surface and the posterior surface; and (d) etching at least one of the anterior surface and the posterior surface.

The increasing of the wettability of the implant may comprise increasing the wettability of the anterior surface of the implant, the anterior surface corresponding to an anterior side of a flexible wing positionable against a distal surface of the tissue adjacent to the aperture in the tissue, the anterior surface of the wing being configured to face the distal surface of the tissue when the wing is positioned against the distal surface of the tissue.

The increasing of the wettability may include forming grooves in at least one of the anterior surface and the posterior surface.

The grooves may have a depth that is in a range from 1 μm to 100 μm.

The grooves may have a depth that is in a range from 7 μm to 40 μm.

In accordance with example embodiments, a device for sealing an aperture in a tissue includes: a base portion; a flexible portion extending from the base portion and configured to contact the tissue adjacent the aperture; a passageway extending through at least one of the base portion and the flexible member and configured to receive a guidewire there through, such that the entire device is freely movable along the guidewire; and a closure member configured to move from a first position to a second position after complete removal of the guidewire, the movement of the closure member from the first position to the second position causing the passageway to be sealed.

In accordance with example embodiments, a device for sealing an aperture in a tissue includes: a foot including a distal portion configured to be disposed distally beyond a distal surface of the tissue when the device is in a sealing position, and a proximal portion configured to extend proximally through the aperture and proximally beyond a proximal surface of the tissue when the device is in the sealing position; a flexible wing positionable against the distal surface of the tissue adjacent the aperture such that the flexible wing is disposed between the anterior distal portion of the foot and the distal surface of the tissue when the device is in the sealing position; and an elongated retention member supported by the proximal portion of the foot, wherein the device is formed of a polymer adapted to remain shelf stable and functional for sealing after terminal sterilization.

The polymer may be adapted to remain shelf stable and functional for sealing after terminal sterilization using at least one of (a) ethylene oxide, (b) electron-beam, (c) gamma irradiation, and (d) nitrous oxide.

In accordance with example embodiments, a device for sealing an aperture in a tissue includes: a foot including a distal portion configured to be disposed distally beyond a distal surface of the tissue when the device is in a sealing position, and a proximal portion configured to extend proximally through the aperture and proximally beyond a proximal surface of the tissue when the device is in the sealing position; a flexible wing positionable against the distal surface of the tissue adjacent the aperture such that the flexible wing is disposed between the anterior distal portion of the foot and the distal surface of the tissue when the device is in the sealing position; and an elongated retention member supported by the proximal portion of the foot, wherein at least one of the foot, the flexible wing, and the elongated retention member is formed at least in part of a polymer that is biodegradable.

The entire device may be formed of a polymer that is biodegradable.

The polymer may comprise Polydioxanone, Poly-L-lactide, Poly-D-lactide, Poly-DL-lactide, Polyglycolide, ϵ-Caprolactone, Polyethylene glycol, or combinations thereof.

The polymer may comprise polydioxanone.

In one aspect of example embodiments of the invention, an implantable device for sealing a surgical perforation is provided. In accordance with example embodiments, this device is polymer-based. For example, the device may be formed of a biodegradable polymer. The resulting biodegradable polymer may be biocompatible and bioresorbable with the ability to degrade when implanted in-vivo.

Biodegradable polymers can have crystalline and amorphous regions and are therefore, in general, semi-crystalline in nature. Degradation of a biodegradable polymer such as initiates in the amorphous regions, with the crystalline regions also degrading but at a slower rate relative to the amorphous regions. Without wishing to be tied to a theory, degradation of a polymer such as Polydioxanone (PDO) occurs along the polymer back bone by hydrolysis of the ester bonds. This non-specific ester bond scission occurs randomly along the polymer chain with water penetration initially cutting the chemical bonds and converting the long polymer chains into natural monomeric acids found in the body, such as lactic acid. Such monomeric acids are then phagocytized by the enzymatic action of special types of mononuclear and multinuclear white blood cells. The polymer is thus degraded into non-toxic, low molecular weight residues that are capable of being eliminated from the body by normal metabolic pathways, e.g. via exhalation and/or excretion. Such a pathway thereby enables reference to the breakdown of such polymers in-vivo through terminology such as absorbable, bioabsorbable, degradation, biodegradation, resorbtion, bioresorbtion, etc.

In another aspect, the biodegradable polymer may be shelf stable even after terminal sterilization, e.g. using ethylene oxide, gamma irradiation, e-beam irradiation, nitrous oxide, etc. for in vivo use. In accordance with example embodiments, the biodegradable polymer is designed to withstand terminal sterilization, such as ethylene oxide sterilization, and still maintain long-term shelf life stability and product functionality. Terminal sterilization, such as by ethylene oxide, can have a dramatic effect on the structural stability of polymers as they are either degraded into low molecular weight species or cross linked into complex polymeric systems, which can negatively alter the post-sterilization polymer properties. Accordingly, in order to provide a post sterilization, shelf-stable, biocompatible polymeric implant; the polymer, in accordance with example embodiments of the present invention, is able to survive the terminal sterilization procedure and still maintain functionality.

It has been found that post-sterilization stability is achievable by using polymers with an inherent viscosity [IV] (which is a method of evaluating the relative molecular weight of the polymeric system) that is of a sufficient starting range to endure a drop in IV post-sterilization and still meet the required implant design requirements. Without wishing to be tied to a theory, it is believed that polymers are susceptible to degrade into lower molecular weight species during terminal sterilization, thereby affecting the inherent viscosity of the implant during storage. By starting with a polymer system with an IV value in its upper range pre-sterilization, it is possible to have a sterile system, post-sterilization with an IV lower than that of the starting system but that is designed to meet the required shelf-life stability. This IV value is typically in the range of 0.5-7.0 dl/g Additionally, in accordance with example embodiments, the use of a specific and defined atmosphere for storage of the implant pre- and post-sterilization further adds to increasing the post-sterilization shelf-life stability of the polymer in question. One such method is the use of a controlled atmosphere, specifically one where excessive moisture is reduced via a vacuum or low moisture containing dried gases such as nitrogen, argon, etc. Furthermore, the use of packaging materials with a low moisture vapor transmission rate, for example orientated polypropylene (OPP), Polyethylene terephthalate (PET), Linear low-density polyethylene (LLDPE), polyethylene (PE), foil-based packaging materials (e.g. aluminium), or combinations thereof, in combination with a low moisture environment can further aid in enhancing the stability of the polymeric material post-sterilization.

Further features and aspects of example embodiments of the present invention are described in more detail below with reference to the appended Figures.

BRIEF DESCRIPTION OF THE DRAWINGS

FIG. 17A shows an implant that utilizes a wing-retention collar.

FIG. 17B shows the implant of FIG. 17B with the collar mounted.

FIG. 17C is an enlarged partial view of the implant of FIG. 17B.

FIG. 43B shows a perspective view of a splittable funnel body with a notched wall.

FIG. 43C shows a side view of the funnel body of FIG. 43B.

FIG. 43D shows a rear view of the funnel body of FIG. 43B.

FIG. 43E shows a perspective view of a splittable funnel body with a notched wall and lead-in notch.

FIG. 43F shows a side view of the funnel body of FIG. 43E.

FIG. 43G shows a rear view of the funnel body of FIG. 43E.

FIG. 55A shows a cross-sectional view of the handle portion of the delivery system of FIG. 52 with the thumb slider moved to a distal position.

FIG. 55B shows an enlarged partial cross-sectional view of the handle portion of the delivery system of FIG. 52 with the thumb slider moved to the distal position.

FIG. 56a shows an enlarged partial cross-sectional view of the handle portion of the delivery system of FIG. 52 with the thumb slider in a proximal position.

FIG. 56B shows an enlarged partial cross-sectional view of the handle portion of the delivery system of FIG. 52 with the thumb slider moved to the distal position.

FIG. 57A shows a cross-sectional view of the handle portion of the delivery system of FIG. 52 at the onset of proximal actuation of the thumb slider.

FIG. 57B shows a cross-sectional view of the handle portion of the delivery system of FIG. 52 with the thumb slider returned to the proximal position after both distal actuation and subsequent proximal actuation.

FIG. 57C shows a cross-sectional view of the handle portion of the delivery system of FIG. 52 with the thumb slider moved to distal position a second time.

FIG. 58 shows a packaged surgical closure device product.

FIGS. 59 and 60 show a loading funnel of the product of FIG. 58.

FIG. 61 shows an exploded view of components of a delivery system and a closure device.

FIG. 62 shows components of a device after removal from a packaging tray of FIG. 58.

DETAILED DESCRIPTION

Figure 1A:
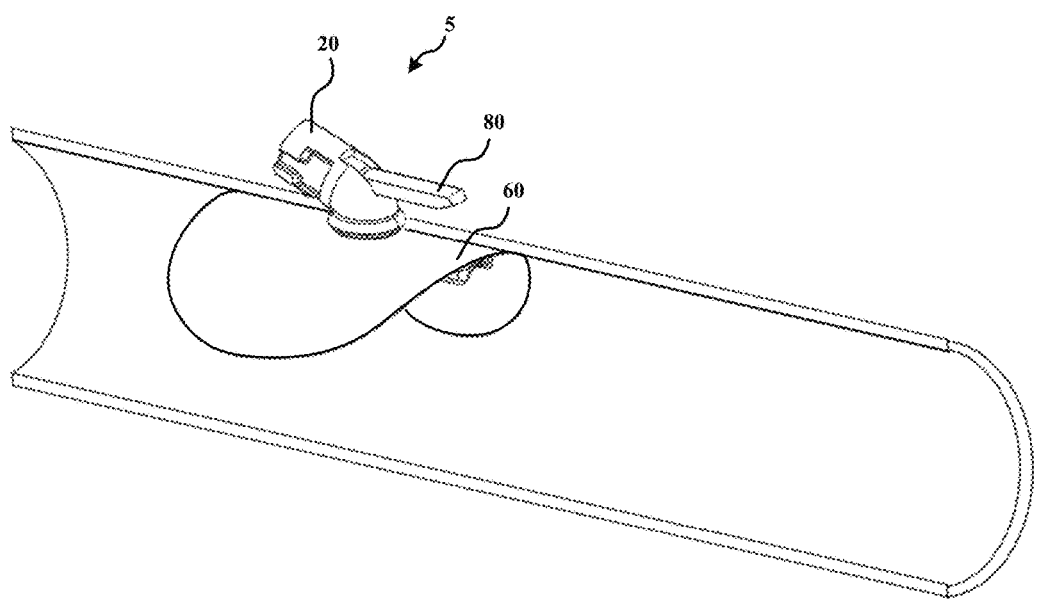
FIG. 1A shows a perspective view of a closure device with an alternative extra-luminal pin and situated on a guidewire extending into an artery, the artery shown in cross-section.

Various example embodiments are described in detail herein. These embodiments generally share certain features in common. Accordingly, the various embodiments each share common features, except to the extent indicated otherwise. As such, for the sake of conciseness, the description of the common features is not repeated in connection with the description of each described embodiment. Further, features that are the same or analogous among the various embodiments are, in connection with some embodiments, given like reference numbers, but followed by a letter associated with the particular embodiment. For example, if an embodiment has an element 7, the corresponding or analogous element in further embodiments would be designated 7a, 7b, 7c, and so on. For convenience, the description of these features is not repeated in connection with each embodiment; rather, it should be understood that the description of these features in connection with other embodiment(s) applies unless indicated otherwise.

As described herein, example embodiments of the present invention provide surgical closure systems, devices, and methods. As such, provided systems, devices, and methods are useful for closing a perforation (i.e., a hole, puncture, tear, rip, or cut, etc.) in any hollow vessel associated with a mammalian surgical procedure. One of ordinary skill in the art will appreciate that the systems, devices, and methods are useful for closing a perforation in any lumen of a mammal, including, for example, the gastrointestinal tract (e.g. the stomach, intestines, colon, etc.), heart, peritoneal cavity, esophagus, vagina, rectum, trachea, bronchi, or a blood vessel.

Although certain figures and embodiments relate to use of systems and devices for closure of a perforation associated with vascular surgery, one of ordinary skill in the art will appreciate that components of a provided device are not size dependent (i.e., are scalable) and are therefore useful for closure of any perforation in a lumen of a mammal.

Some embodiments of the present invention are directed to a closure system, device, and method of percutaneous closure of an arteriotomy following an endovascular/intraarterial procedures.

One of ordinary skill in the art will recognize that many mammalian lumina are comprised of one or more friable tissues. Thus, a common difficulty associated with surgical closure of a perforation in such lumina is that suture material, used in typical closure systems, tends to cause tears in the friable tissue. Such tearing of the luminal tissue impedes healing and causes scarring. Indeed, such tearing of the friable tissues of the internal lumina of blood vessels can lead to scarring, dislodgment of tissue particles, blockage, or even eventual death of the patient. In view of the fragile nature of luminal tissues, an aspect of example embodiments of the present invention is to provide systems, devices, and methods that allow a seal to be formed closure of a tissue perforation in a reliable manner with minimal trauma to the luminal tissue, for example, by providing a sutureless seal.

With regards to the arterial wall morphology, in the context of example embodiments directed to closing arterial perforations, the fibrous adventitial layer of an artery (i.e., the outer layer) is relatively tough, whilst the intimal and endothelial layers are friable. Because of the morphology of the arterial wall, an arteriotomy may be circumferential in nature and perpendicular to the longitudinal axis of the artery.

Closure Device

Referring to FIG. 1A, a percutaneous Vascular Closure Device (VCD) 5 is configured to provide relatively large vascular closures. An example of an intended application of this device 5 is the percutaneous closure of 12-30 F arteriotomies following endovascular/intraarterial procedures. In clinical practice, commonly targeted arteries may include, for example, the common femoral artery, the subclavian artery, axillary artery, ascending aorta, brachial artery, and other vessels used for endovascular access. At the conclusion of the interventional procedure, the implant or device 5 is percutaneously delivered into the artery 2 via a procedural sheath 100 (illustrated, e.g. in FIG. 30) over a guidewire 150.

Figure 1B:
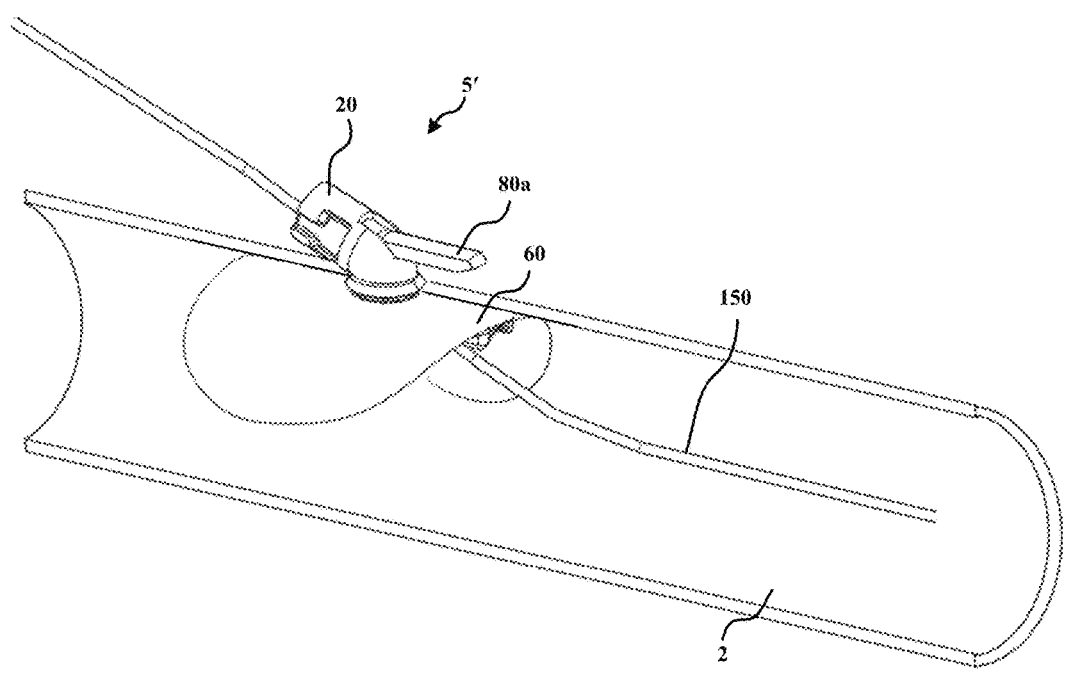
FIG. 1B shows a perspective view of the closure device of FIG. 1A with an alternative extra-luminal pin and situated on a guidewire extending into the artery of FIG. 1A, the artery shown in cross-section.

The device 5' shown in FIG. 1B, differs from the device 5 only in that the device 5' employs an extra-luminal pin 80a that differs from an extra-luminal pin 80 of the device 5. In particular, referring to FIGS. 7C and 7D, the extra-luminal pin 80a has a slot 85a to facilitate the pin 80a being moved into its distal or deployed position, as described in further detail herein, while the guidewire 150 remains in situ, whereas the extra-luminal pin 80 is configured to prevent full distal extension of the extra-luminal pin 80 when the guidewire 150 remains in situ. Aside from this difference, as well as the presence of the guidewire in certain views, the devices 5 and 5' should be considered identical. Moreover, for the sake of conciseness, the description of the device 5 is considered interchangeable with the device 5', except to the extent indicated otherwise.

Figure 1C:
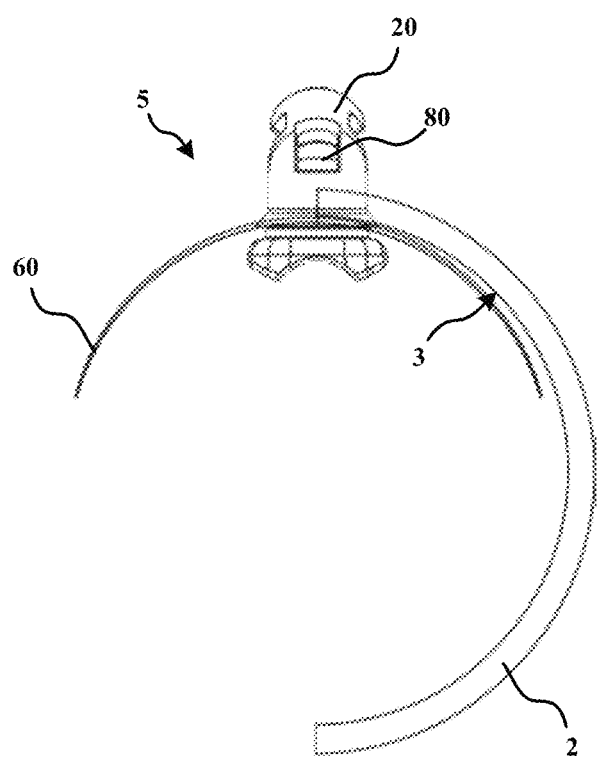
FIG. 1C shows a front view of the closure device of FIG. 1A engaging the artery, the artery shown in cross-section.

FIGS. 1A to 1C illustrate final closure dynamics of the device 5, 5' in situ in a sectioned artery 2, with FIG. 1A showing the device 5 after removal of the guidewire 150. The implant device 5, 5' includes a body or foot core 20, a flexible wing 60, and the extra-luminal pin 80, 80a.

All implant device components (e.g., the foot core 20, the flexible wing 60, and the extra-luminal pin 80, 80a in the illustrated examples of FIGS. 1A to 1C) are manufactured from synthetic absorbable materials, although other suitable non-synthetic and/or non-absorbable materials may be used instead of, or in addition to, these synthetic absorbable materials. The flexible wing 60, the foot core 20, and the extra-luminal pin 80, 80a may each be manufactured from any suitable material, e.g. Polydioxanone (PDO), Poly-L-lactide (PLLA), Poly-D-lactide (PDLA), blend of D-lactide and L-lactide, i.e. poly-DL-lactide (PDLLA), Polyglycolide (PGA), blend of Poly-L-lactide and Polyglycolide (PLGA), ε-Caprolactone, Poly (ethylene glycol) (PEG), magnesium alloy, 3-hydroxypropionic acid, Polyanhydrides, poly(saccharide) materials or combinations of these. It should be appreciated, however, that any one or more of the components of the implant device 5, 5' may be formed of any suitable material. Moreover, some or all of the components of the device 5 may be made of the same or different materials relative to each other. The flexible wing may be manufactured as a thin sheet, it may also be made of a woven material, e.g. using electrospinning, weaving and knitting processes.

FIGS. 1A to 1C represent each of these components in situ. The arteriotomy seal is achieved in large part by the hydraulic haemodynamic pressure, which acts on the flexible wing 60 to force the flexible wing 60 against the luminal surface and conform to the luminal topography to seal around the arteriotomy.

FIGS. 2A to 2D show the assembled implant 5 showing three components—foot core 20, flexible wing 60, and extra-luminal pin 80. Although the example illustrated in FIGS. 2A to 2D consists of three pieces, it should be appreciated that more or few pieces may be provided. For example, the flexible wing 60 may be integrally formed with the foot 20 as a single, monolithic piece.

Figure 2A:
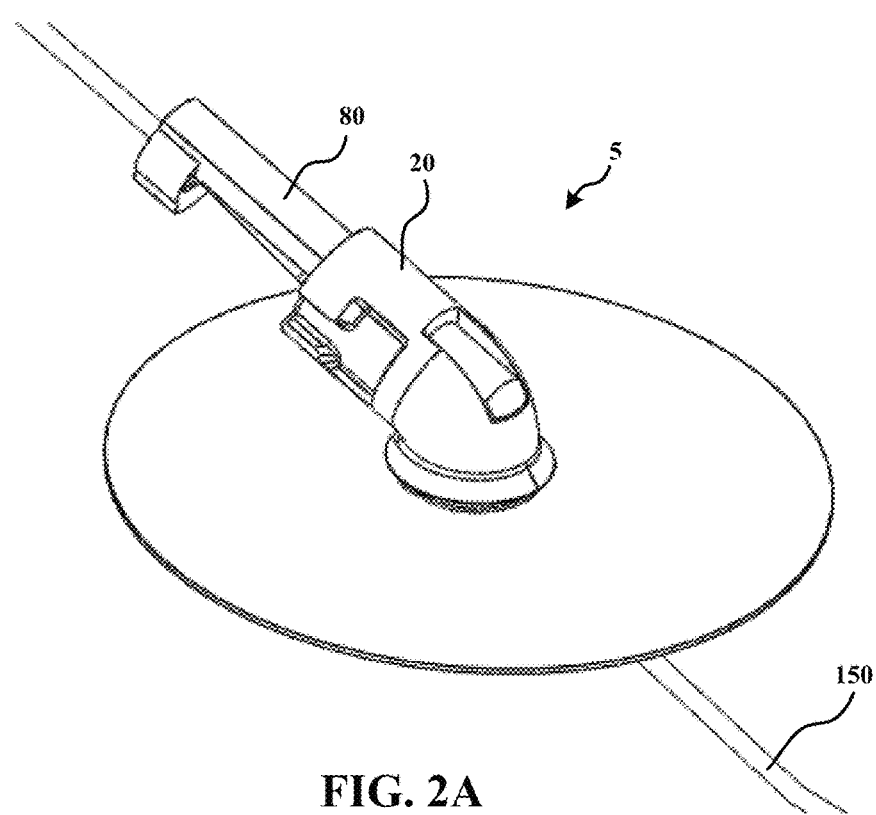
FIG. 2A shows a perspective view of the closure device of FIG. 1A when not engaged with the artery, disposed on a guidewire, and with an extra-luminal pin in a retracted position.
Figure 2B:
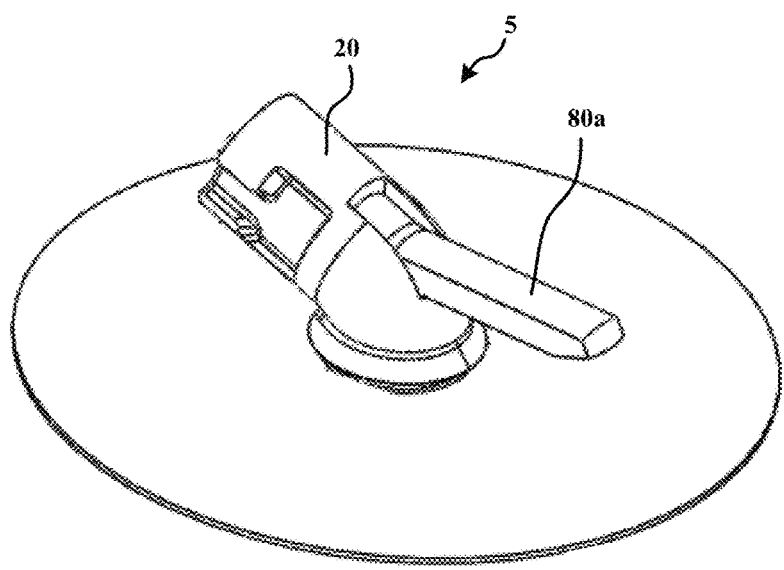
FIG. 2B shows a perspective view of the closure device of FIG. 2A when not engaged with the artery, and with the extra-luminal pin in a deployed position.
Figure 2C:
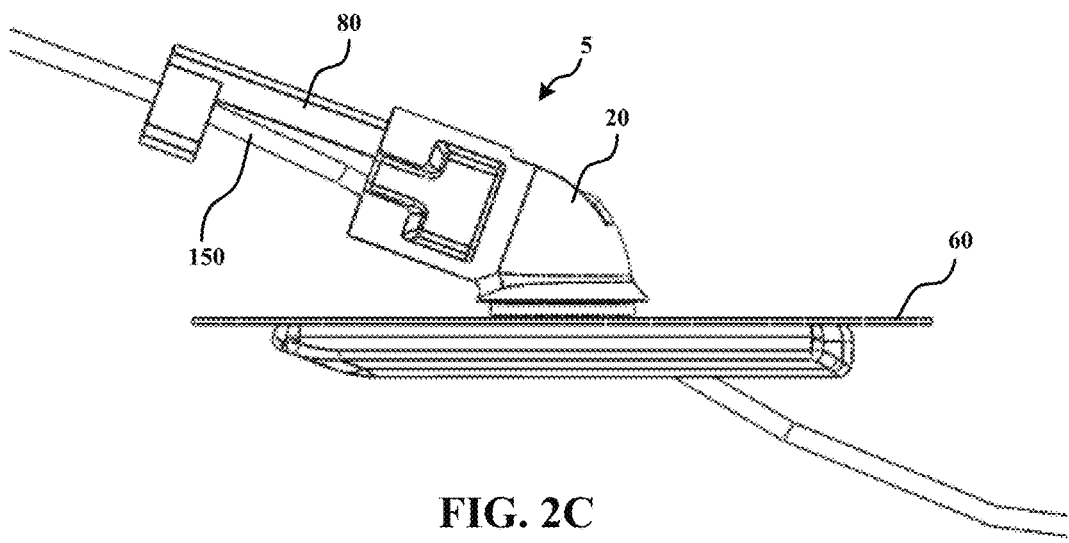
FIG. 2C shows a right side view of the closure device shown in FIG. 2A.
Figure 2D:
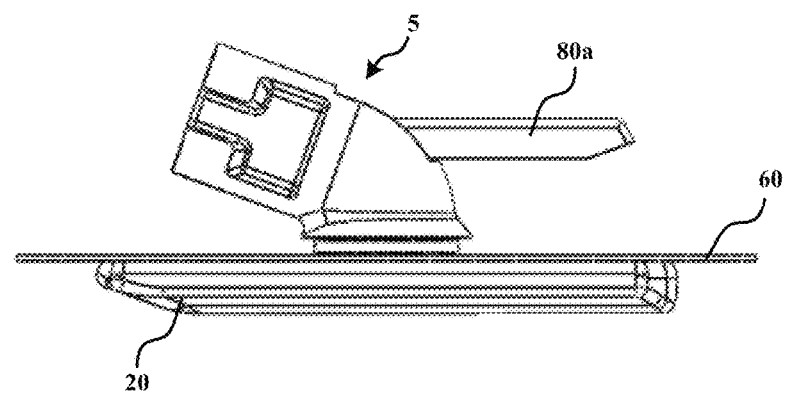
FIG. 2D shows a right side view of the closure device shown in FIG. 2B.

As illustrated in FIGS. 2A and 2C, a guidewire 150 extends through the implant 5. FIGS. 2B and 2D show the implant 5 after proximal retraction of the guidewire 150 and subsequent extension, or deployment, of the extra-arterial pin 80 to its distal, or deployed, position relative to the foot core 20.

FIGS. 2A and 2C show the implant 5 with the extra-luminal pin 80 in a retracted or undeployed state, and FIGS. 2B and 2D show the extra-luminal pin 80 in a distally extended or deployed state.

Figure 30:
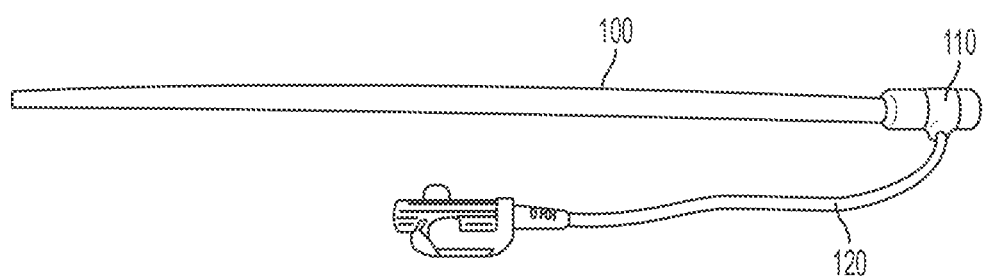
FIG. 30 shows a side view of a procedural sheath.

The implant 5 is inserted into the artery 2 through a procedural sheath 100 illustrated in FIG. 30 and over the guidewire 150, which extends through the sheath 100 and into the intra-arterial space.

Referring, for example, to FIGS. 3A to 3D, the foot core 20 includes both an intra-luminal section 25 which is configured to be maintained in the interior of the artery 2, or other tissue structure, when the implant 5 is in situ, and an extra-luminal section 40 which passes through the arteriotomy across the arterial wall when the implant 5 is in situ. The intra-luminal section 25 and the extra-luminal section 40 are separated at a recess 22, which is configured to receive the wing 60 such that a cylindrical recessed surface 23 is maintained inside a circular central cut-out or aperture 65 in the wing 60. The aperture 65 is illustrated, for example, in FIGS. 6A and 6B.

It is noted that since some illustrated examples are provided in the context of an arteriotomy, the terms "intra-luminal" and "extra-luminal" may be referred to as "intra-arterial" and "extra-arterial" in the context of the illustrated embodiments, it being understood that the arteriotomy-closure application is non-limiting and the closure of any suitable tissue aperture may be performed by example embodiments of the present invention.

The extra-luminal section 40 of the foot core 20 is provided in the form of a neck 42 which extends from the intra-luminal section 25 at an angle, e.g. selected from a range from 10° to 70°, and has five primary functions:

1. Secure the flexible wing 60 within the recessed section 22. This recessed section 22 also provides an effective seal between the flexible wing 60 and foot core 20. In the example illustrated, e.g. in FIGS. 1A to 1C, the flexible wing 60 is free to rotate within this recess 22. It should be understood, however, that the engagement of the wing 60 in the recess 22 may be provided such that the wing 60 is not rotatable within the recess 22.

2. Secures and allows release of the entire implant to a delivery system via interlock recesses 45 in the neck 42. This functionality is described in further detail elsewhere herein.

3. Houses the extra-luminal pin 80 and secures it when deployed to its final position.

4. Houses a guidewire channel or conduit 50. The guidewire channel 50 is illustrated, e.g. in FIG. 3D.

5. The 10°-70° incline on the neck in combination with the extra-luminal pin 80, or 80a, also provides, e.g. for safety purposes, protection against the implant being pushed off the luminal surface by application of extracorporeal pressure above the implantation site or due to patient movements.

The intra-luminal section 25 of the foot core 20 has a primary function to provide a rigid scaffold to support the flexible wing 60. The underside of the intra-luminal section 25 may be concave in cross-section to reduce its profile within the artery 2 and has a hollow entry portion or port 52 of the guidewire channel 50 adjacent the neck 42, shown in the sectioned foot core 20 of FIG. 3D.

FIGS. 4A to 4F show another foot core 20a. This configuration has a circular intra-luminal portion 25a in plan view and a concave surface 30a which is concave in cross-sectional profile within the artery 2.

Figure 5A:
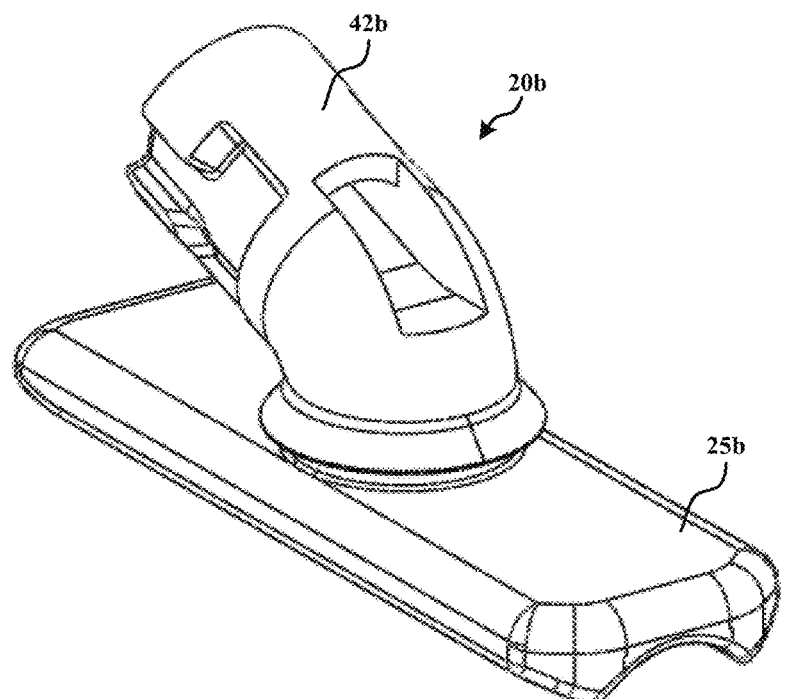
FIG. 5A shows a perspective view of another foot core.
Figure 5B:
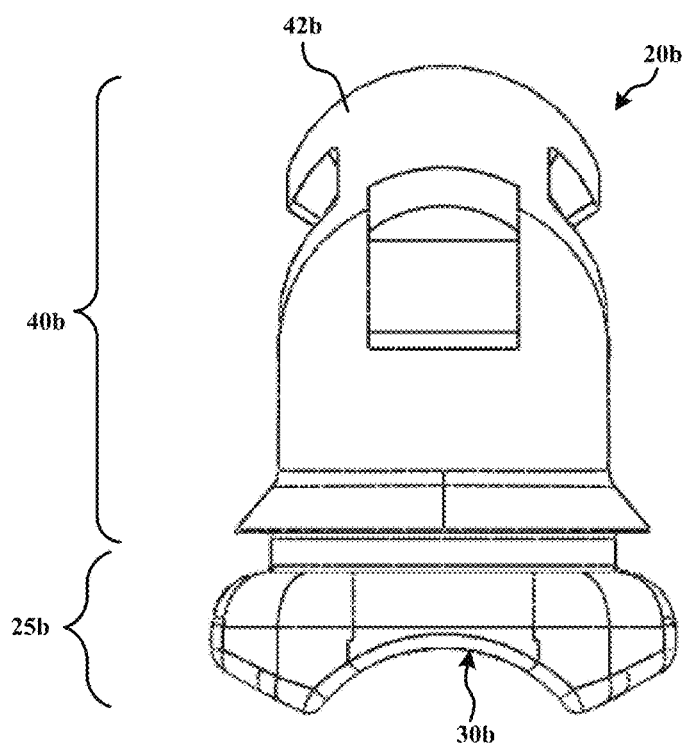
FIG. 5B shows a front view of the foot core of FIG. 5A.

It should be appreciated that many variations of the intra-luminal portion may be provided, only a limited number of which are shown herein. For example, FIGS. 5A to 5B show another foot core 20b having an intra-luminal portion 25b that is generally rectangular in plan view and includes a concave bottom surface.

Figure 6A:
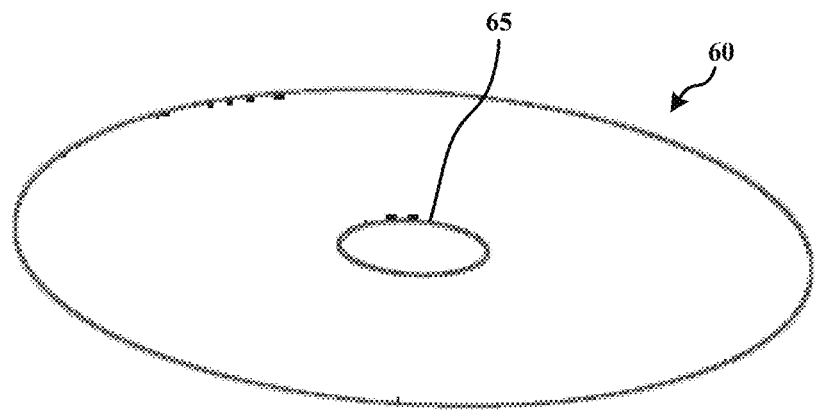
FIG. 6A shows a wing element of the device of FIG. 1A in a flat state.
Figure 6B:
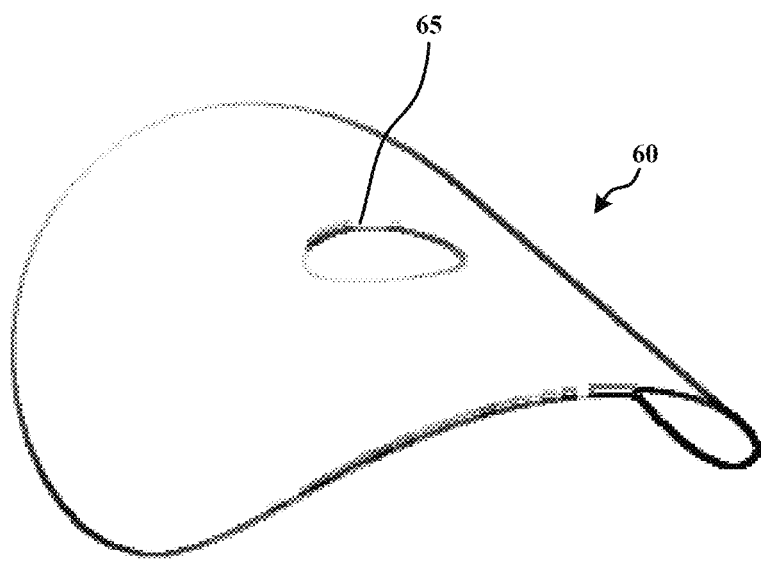
FIG. 6B shows the wing element of FIG. 6A in a folded or curved state.

The flexible wing 60, FIGS. 6A and 6B, is a thin disc sized to be larger than the arteriotomy diameter (arteriotomy diameter is equivalent to the outer diameter of the delivery/procedural sheath 100). The central hole 65 and disc portion are circular in shape, in plan view. It should be understood, however, that other geometries may be provided for the hole and/or the disk portion of the wing 60. The central hole 65 is sized to accept recessed cylindrical surface 23 within the foot core 20's flexible-wing retention recess 22 shown, e.g. in FIGS. 3A and 3B, and is free to rotate relative to the foot core 20 about the concentric axis of the recessed cylindrical surface 23.

FIG. 6A shows the flexible wing 60 in its flat and relaxed state, and FIG. 6B shows the flexible wing 60 in its curved state, which corresponds to the final configuration within the artery 2. The curvature of the wing 60 shown in FIG. 6B corresponds to the curvature of the interior of the artery to which the wing 60 conforms in its final implanted state. When implanted, the wing 60 is pressed against the artery interior wall by hemodynamic hydraulic pressure exerted by the blood in the artery 2. Although the wing 60 is flat, or planar, in its relaxed state, it should be appreciated that the wing 60 may be curved or have any other suitable geometry in its relaxed state.

Referring, e.g. to FIGS. 1A to 1C, the flexible wing 60 is positioned within the artery 2 against the luminal surface 3 adjacent the arteriotomy and held in this position with the aid of the hemodynamic hydraulic pressure it acts as the primary seal around the arteriotomy to control bleeding. Referring to FIG. 1C, the wing 60 is illustrated slightly pulled away from the luminal surface 3 only to facilitate illustration.

In addition to elastically deforming to conform to the luminal surface 3 of the artery 2, the flexible wing 60 also elastically deforms to fit within the procedural sheath 100 for delivery into the artery 2. This is achieved by rolling the wing 60 into a cylinder-like configuration. Once within the artery 2, and beyond the procedural sheath 100, the flexible wing 60 intrinsically recovers towards its flat state to allow the hemodynamic hydraulic pressure in the artery 2 to conform the wing 60 to the shape of the arterial luminal and surface topography 3. In this regard, the elasticity of the wing 60 allows the wing 60 deform locally at differing areas of the luminal surface 3 of the artery 2. This allows the wing 60 to conform to local irregularities along the surface 3 to ensure that the arteriotomy is adequately sealed despite such irregularities.

The flexibility of the wing 60 is not just important in a lateral configuration to facilitate collapse during delivery, but it is also important to flex in a longitudinal plane. Flexibility in both lateral and longitudinal planes is important to ensure an effective seal around the arteriotomy of arteries in differing disease states with different surface topographies and varying anatomical configurations. Longitudinal flex is facilitated by the configurations shown, e.g. in FIGS. 2A-5D, by the flexible wing 60 and the foot core 20 being separate and distinct parts that are non-fixedly mated together. For example, since the wing 60 is not fixed to the foot 20, it is able to separate from the upper surface of the relatively rigid intra-luminal portion 25 of the foot core 20 at regions where the topography of the arterial surface 3 deviates or is disposed at a greater distance from the upper surface of the intra-luminal portion 25 than at adjacent regions of the surface 3.

Although the wing 60 has a circular outer periphery, it should be understood that the wing 60 may be provided with any suitable geometry. Further, although the wing 60 has a uniform thickness, it should be understood that the wing 60 may be provided with a thickness that varies at different regions of the wing 60. For example, the wing 60 could have a thickness in its central region that is greater than a thickness toward the circumferential periphery of the wing 60.

Figure 7A:
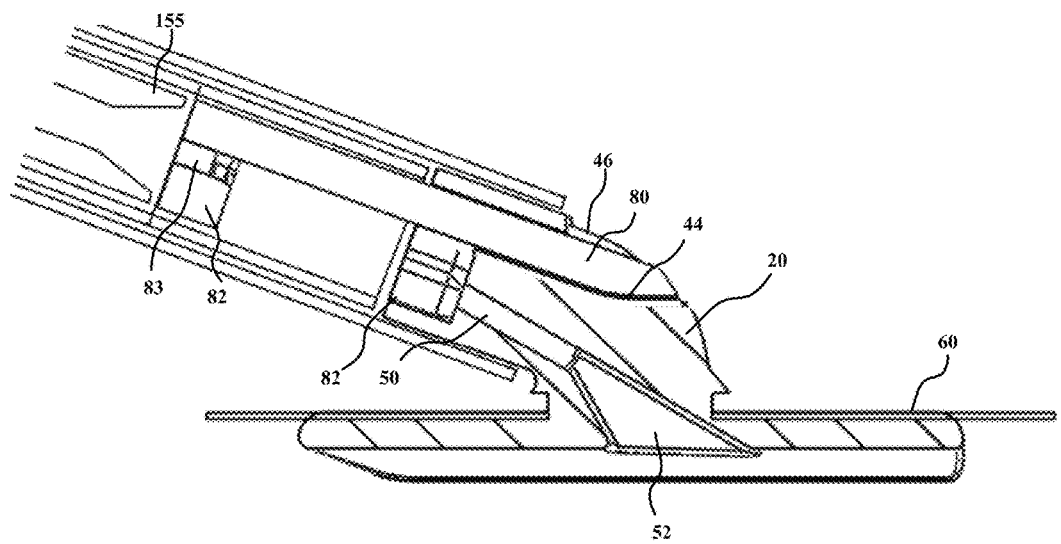
FIG. 7A shows a cross-sectional right side view of a closure system incorporating the closure device shown in FIG. 1A.
Figure 7B:
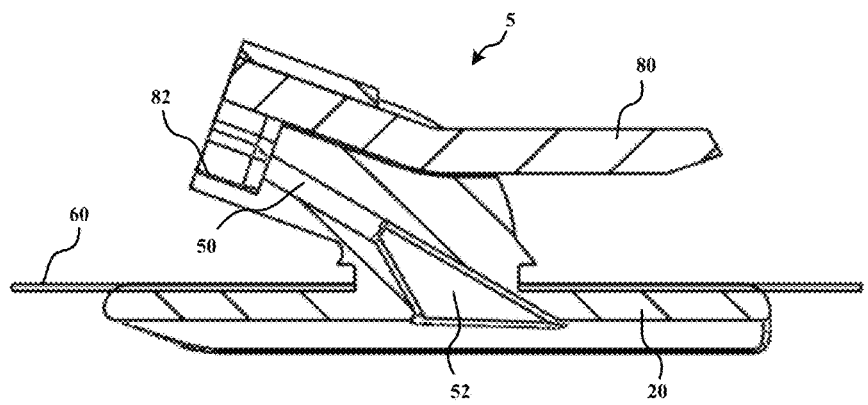
FIG. 7B shows a cross-sectional right side view of the closure device shown in FIG. 7A in a released state.
Figure 32:
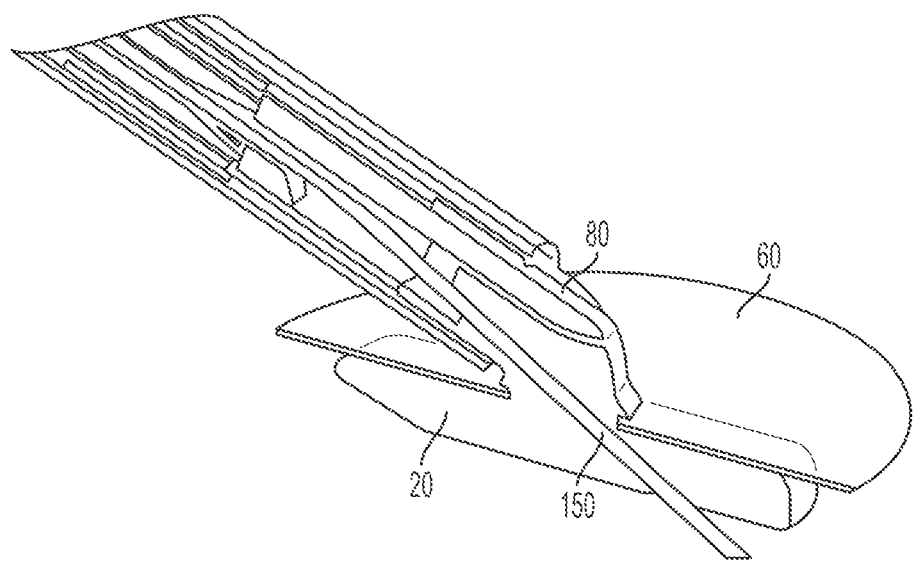
FIG. 32 is a cross-sectional perspective view of the closure device attached to a distal tip of the delivery system of FIG. 31A.

FIGS. 7A and 7B shows an assembled implant 5 in cross section. FIG. 7A shows the implant 5 in a state where the guidewire 150 would be in situ, as illustrated, e.g. in FIG. 32, or subsequent to removal of the guidewire 150. FIG. 7B shows the deployed implant 5.

The extra-luminal pin 80 is a safety feature of the closure system to prevent the implant being pushed off the luminal surface by application of extracorporeal pressure above the implantation site or due to patient movements. The extra-luminal pin 80 in the illustrated example does not generally contribute to or form part of the sealing function of the implant 5. The implant 5 will seal the arteriotomy in the absence of the extra-luminal pin 80 in accordance with some example embodiments. The extra-luminal pin 80 is deflected parallel to the artery 2 wall as it is advanced, as illustrated, e.g. in FIG. 7B. This deformation of the extra-luminal pin 80 helps secure it in its post deployment position. The pin 80 is also maintained in this position via a press fit between the proximal portion 82 of the pin and the proximal recess 47 of the foot core 20 into which the proximal portion 82 is pressed.

Figure 7C:
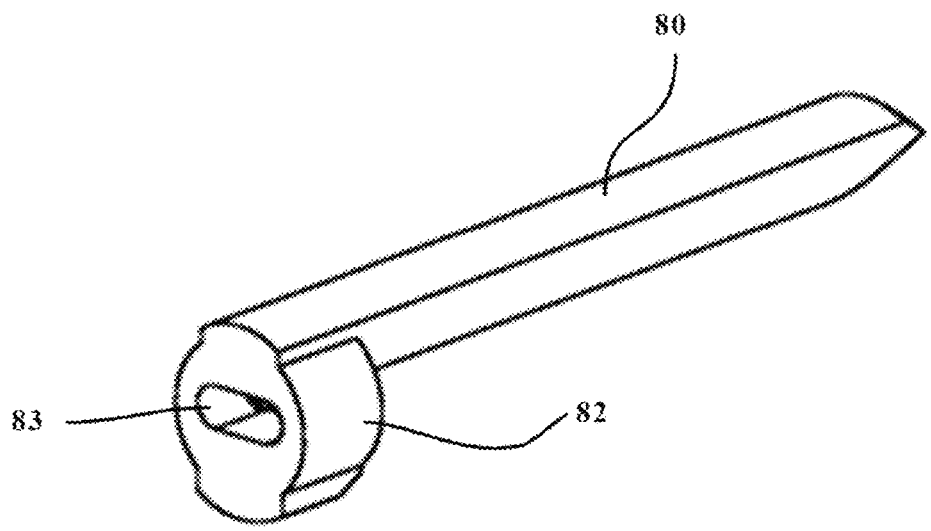
FIG. 7C shows a perspective view of the extra-luminal pin element.

Depending on implant design and requirements, the extra-luminal pin 80 may also be used to occlude the guidewire hole within the foot core 20 when deployed, e.g. in a configuration such as illustrated in FIGS. 7A and 7B, the pin 80 being illustrated in isolation in FIG. 7C. When deployed, as illustrated, e.g. in FIG. 7B, an enlarged proximal portion 82 of the extra-luminal pin 80 blocks the guidewire channel 50. In its proximal or retracted position, the pin 80 allows the guidewire 150 to pass through channel 83 in the enlarged proximal portion 82. When the pin 80 is moved into its distal or deployed position, the channel 83 does not align with the channel 50 in the foot core 20, thereby blocking the channel 50. In the proximal or retracted position, the guidewire is able to pass through both channels 50 and 83 since the channels 50 and 83 are sufficiently axially spaced apart.

It should be understood, however, that any other suitable mechanism may be provided for closing the guidewire channel 50. For example, again referring to FIGS. 7A and 7B, the formation of coagulated blood in the conically shaped entry portion 52 of the guidewire channel 50. The coagulated blood would then be pressed and locked into the narrowing conical geometry of the entry portion 52 by the hydraulic pressure exerted by the blood in the artery 2. To facilitate coagulation of the blood in the entry portion 52, the guidewire 150 may be left in place for, e.g. several minutes (e.g. 4 to 5 minutes). The presence of the guidewire may, during this period, induce sufficient clotting of the blood to form the closure in the entry portion 52. Then, upon retraction of the guidewire 150, the coagulated blood would compress and collapse to fill the void left by the removal of the guidewire 150.

Figure 7D:
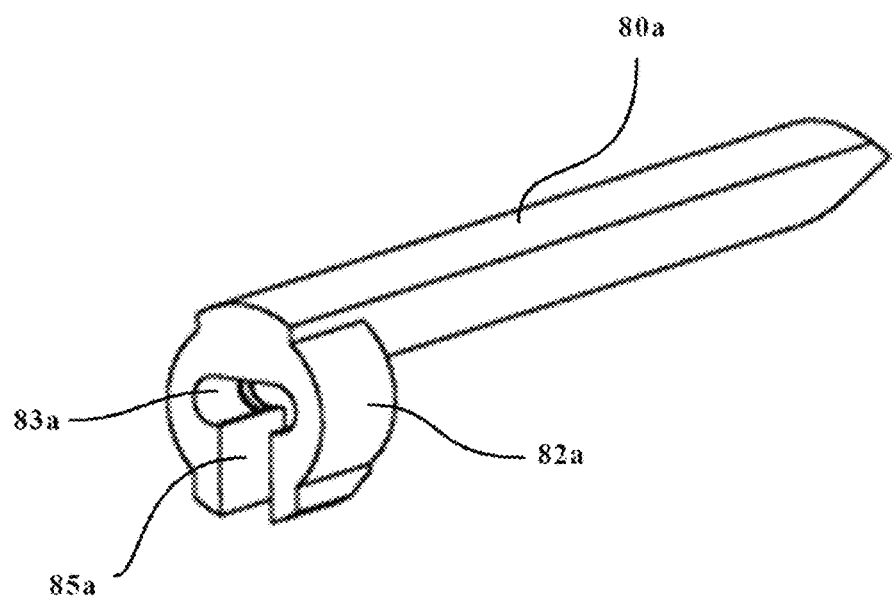
FIG. 7D shows a perspective view of another extra-luminal pin element.

Although the illustrated entry portion 52 of the guidewire channel 50 is conical, it should be appreciated that any suitable geometry may be provided. Referring to FIG. 7D, an alternative extra-luminal pin 80a is shown with an additional slot 85a to facilitate the pin 80a being moved into its distal or extended position whilst the guidewire 150 remains in place.

Some alternative embodiments to the extra-luminal pin 80 shown, e.g. in FIG. 7C, are shown in FIGS. 8A to 12B.

Figure 8A:
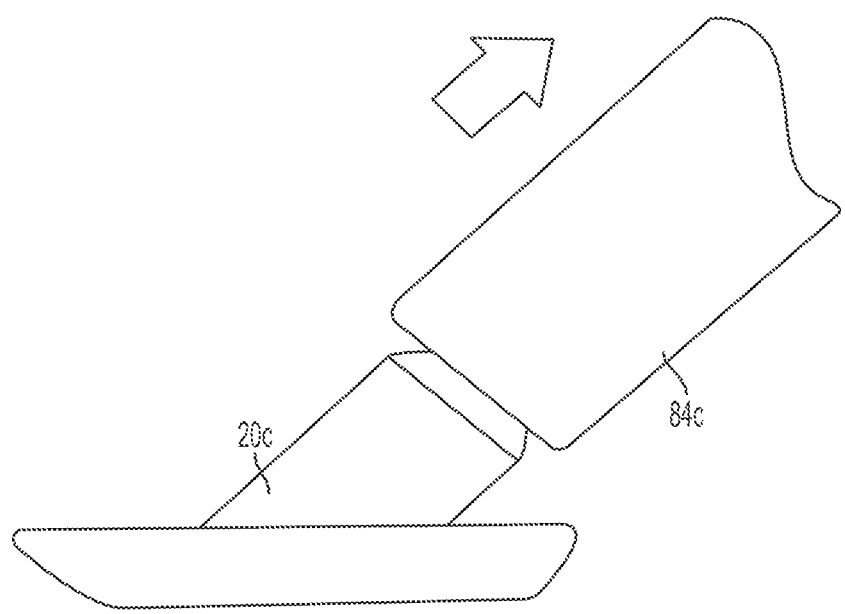
FIG. 8A shows a left side view of another closure system.
Figure 8B:
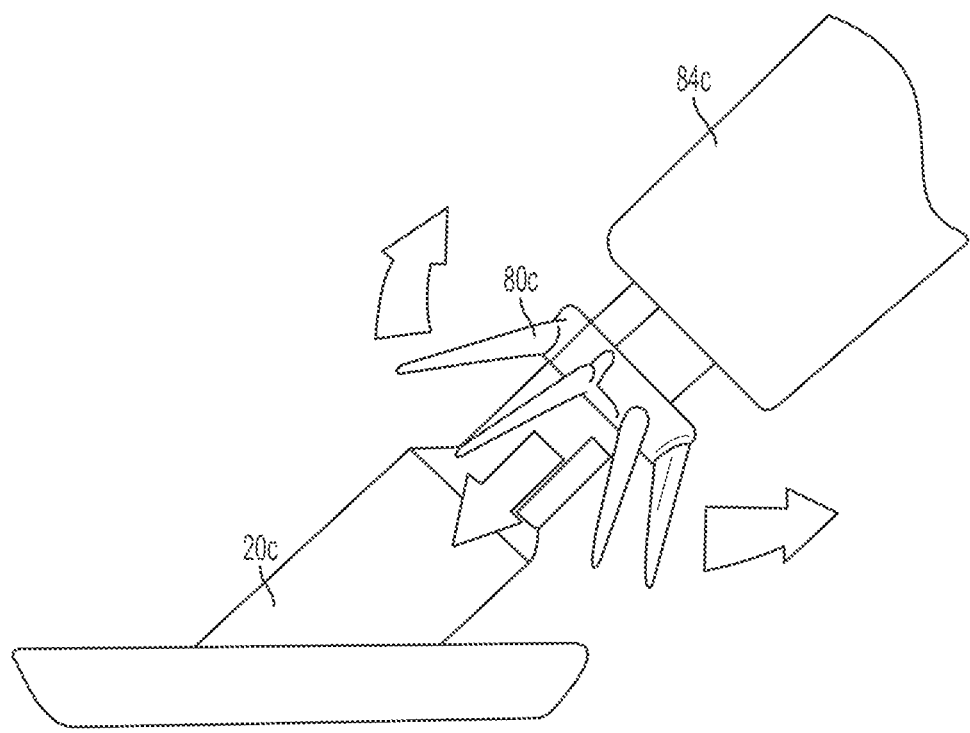
FIG. 8B shows a left side view of the closure system of FIG. 8B after deployment of an extra-luminal pin arrangement.

Referring to FIGS. 8A and 8B, provided are a series of protrusions 80c that, in the radially extended position of FIG. 8B, engage the extra-arterial subcuticular tissue to prevent the implant from being pushed forward. The protrusions 80c are exposed and allowed to spring into their radially extended position by proximal retraction of an outer shaft sleeve 84c configured to radially constrain and cover the protrusions 80c when the outer shaft sleeve 84c is in the distal position illustrated in FIG. 8A.

Figure 9A:
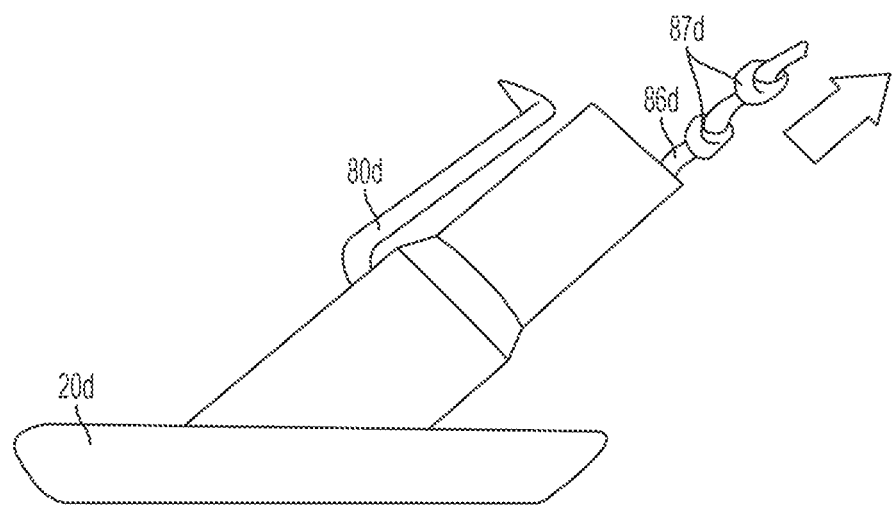
FIG. 9A shows a left side view of another closure system.
Figure 9B:
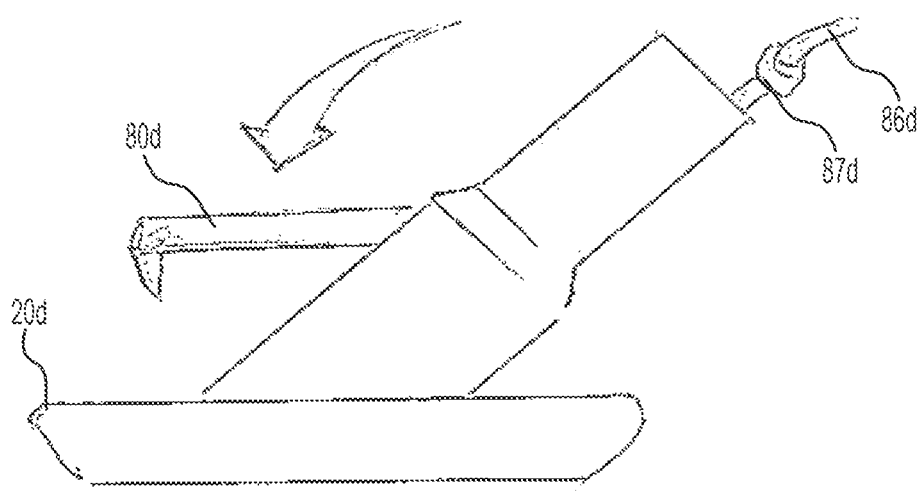
FIG. 9B shows a left side view of the closure system of FIG. 9A after deployment of an extra-luminal pin.

FIGS. 9A and 9B show an extra-luminal pin 80d attached to a suture 86d, which when pulled proximally, flips the pin forward to engage the extra-arterial subcuticular tissue to prevent the implant being inadvertently pushed forward. The suture 86d may include a series of knots 87d to lock and hold the pin 80d in any desired angle between the position shown in FIG. 9A and the position shown in FIG. 9B, depending on, e.g. tissue thickness and/or resistance. The suture 86d, or any other suture described herein, may be formed of any suitable material. For example, any of the sutures described herein may be formed, in whole or in part, of a bio-absorbable material.

Figure 10A:
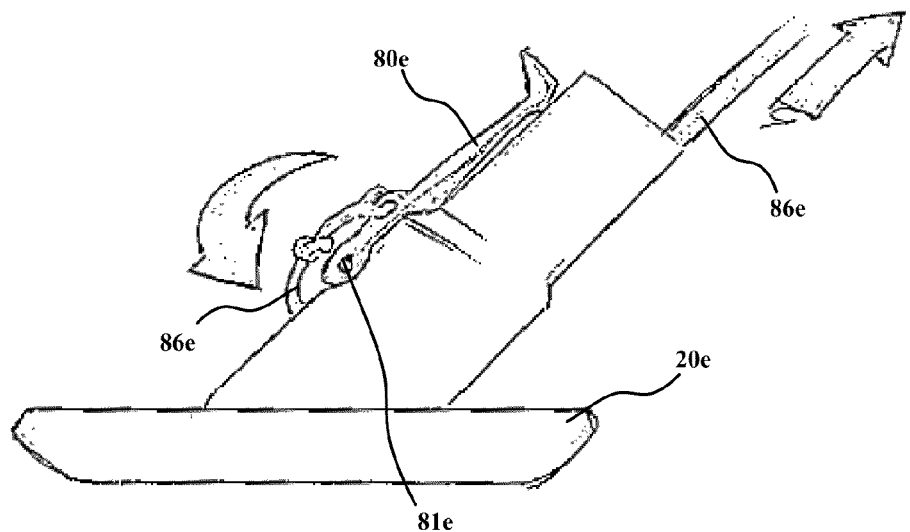
FIG. 10A shows a left side view of another closure system.
Figure 10B:
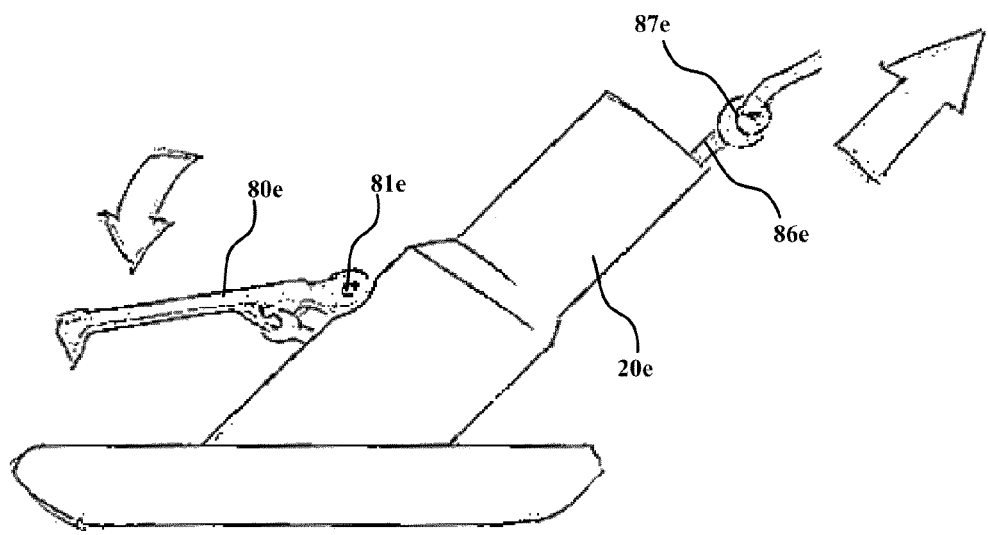
FIG. 10B shows a left side view of the closure system of FIG. 9A after deployment of an extra-luminal pin.

FIGS. 10A and 10B show an arrangement similar to that shown in FIGS. 9A and 9B. In this arrangement, the extra-luminal pin 80e is attached to a suture 86e; however the pin 80e has a pivot attachment or joint 81e to connect to the foot core 20e. By pulling the suture 86e, the pin flips forward, via rotation about the pivot attachment 81e, to engage the extra-arterial subcuticular tissue of the artery 2 to prevent the implant from being pushed forward. The suture 86e may include a series of knots 87e to lock and hold the pin 80e in any desired angle between the position shown in FIG. 10A and the position shown in FIG. 10B, depending on, e.g. tissue thickness and/or resistance.

Figure 11A:
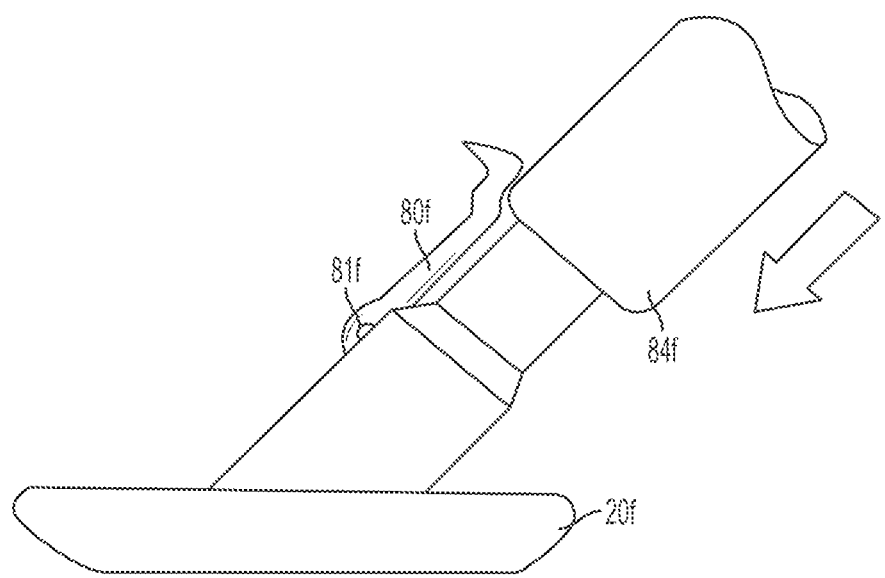
FIG. 11A shows a left side view of another closure system.
Figure 11B:
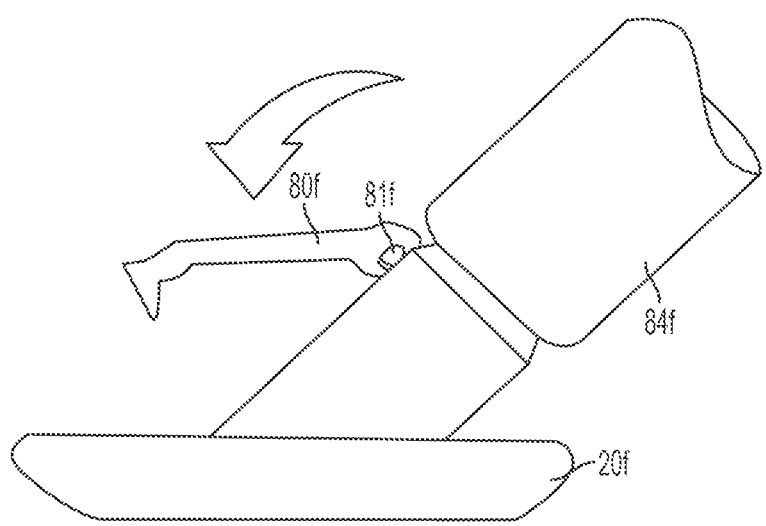
FIG. 11B shows a left side view of the closure system of FIG. 11A after deployment of an extra-luminal pin.

FIGS. 11A and 11B show an arrangement that is similar to that of FIGS. 10A and 10B, but without a suture. The pin 80f has a pivot joint or attachment 81f to the foot core 20f activated by movement of an outer shaft sleeve 84f to engage the extra-arterial subcuticular tissue of the artery 2 to prevent the implant from being inadvertently pushed forward. The sleeve 84f may engage an angled surface of the pin 80f to begin rotation of the pin 80f about the pivot attachment 81f. The pin may be moved to the position shown in FIG. 11B by any suitable mechanism. For example, the pin 80f may be spring biased toward the position shown in FIG. 11B, with the sleeve 84f, disengaging a latch, detent, or other mechanism that maintains the pin 80f in the position shown in FIG. 11A.

Figure 12A:
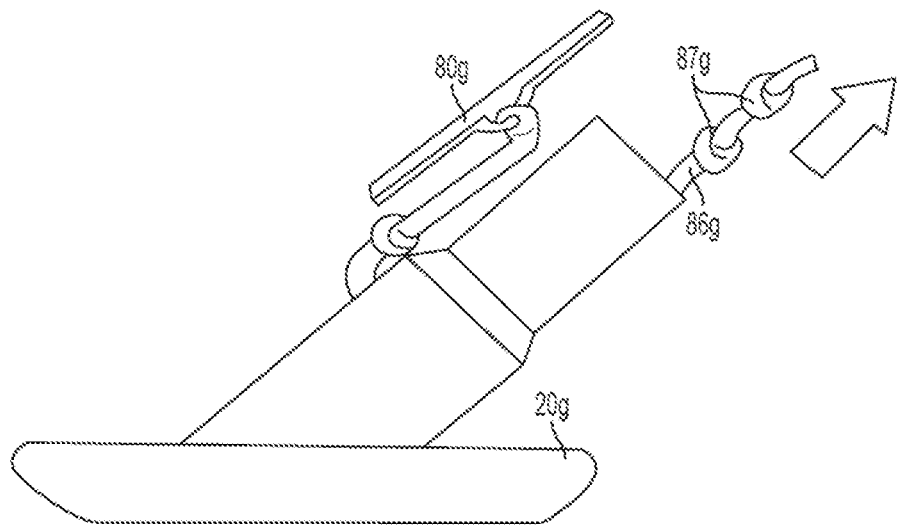
FIG. 12A shows a left side view of another closure system.
Figure 12B:
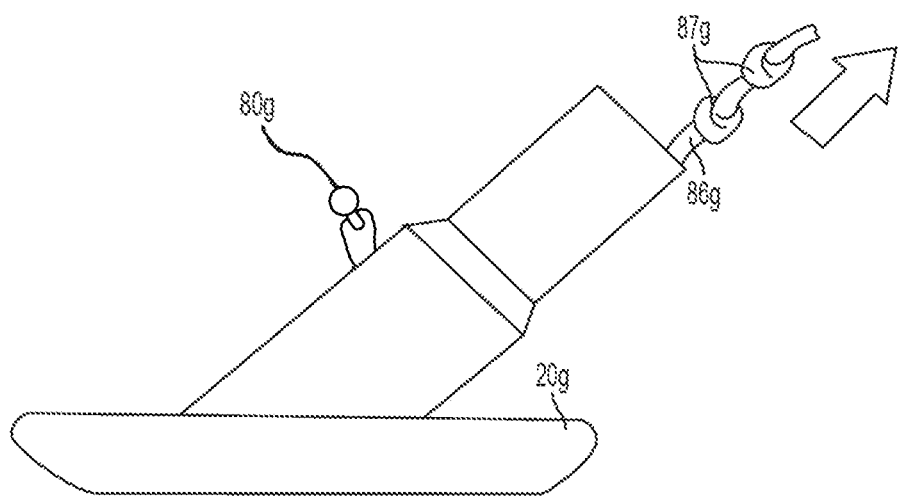
FIG. 12B shows a left side view of the closure system of FIG. 12A after deployment of an extra-luminal pin.

FIGS. 12A and 12B show an extra-luminal T-bar 80g attached to the end of a suture 86g, which when pulled proximally, engages the T-Bar 80g with the extra-arterial subcuticular tissue to prevent the implant from being inadvertently pushed forward. The suture 86g may include a series of knots 87g to lock and hold the pin 80g in any desired angle or position between the position shown in FIG. 12A and the position shown in FIG. 12B, depending on, e.g. tissue thickness and/or resistance.

FIGS. 13A to 18 show variations on the configuration of the foot core.

Figure 13A:
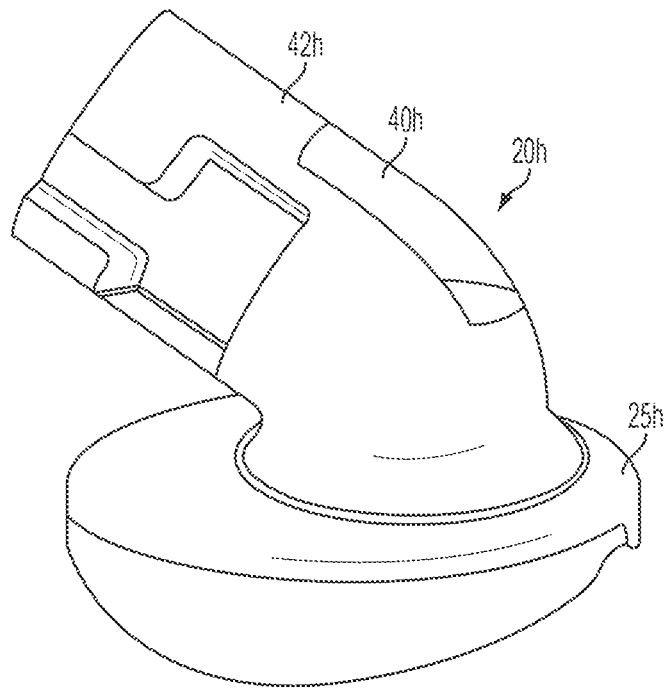
FIG. 13A shows another foot core.

The foot core 20h of FIG. 13A has the intra-luminal portion 25h off-set proximally, toward the rear of the neck section 42h. The intra-luminal portion 25h is circular in shape but the extra-luminal portion 40h meets the intra-luminal portion 25h at a location that is non-concentric to the circular cross-section of the intra-luminal portion 25h. An advantage to this bias is that during delivery of the implant, specifically, as the delivery device is withdrawn from the artery to position the implant against the arteriotomy, the biased intra-luminal portion 25h offers more security or overlap between the intra-luminal portion 25h of the foot core 20h and the distal wound edge of the arteriotomy to prevent inadvertent pull-out from the artery.

Figure 13B:
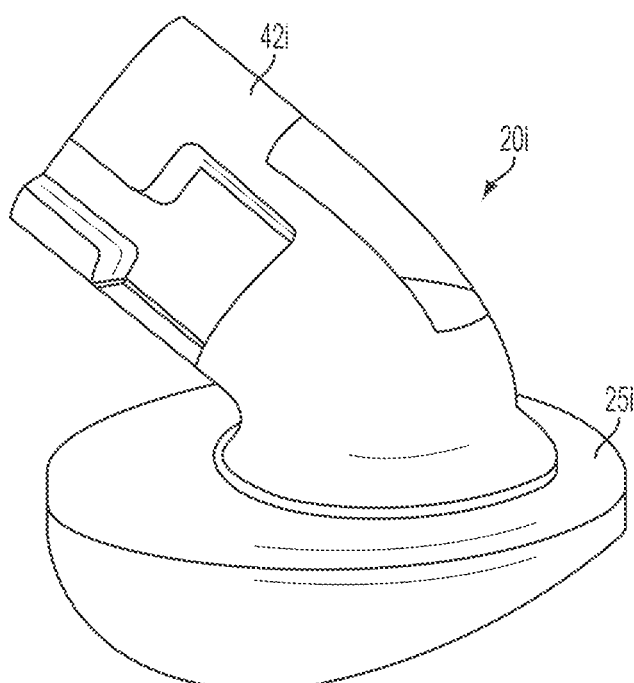
FIG. 13B shows another foot core.

The foot core 20i of FIG. 13B is similar to the foot core 20h of FIG. 13A, but with a larger angle between the intra-luminal section 25i and the neck 42i of the implant.

The larger angle has the advantage of further encouraging the heel of the intra-arterial implant to remain within the artery 2 during withdrawal of the delivery device 60 and positioning the implant against the lumen adjacent to the arteriotomy to prevent inadvertent pull-out from the artery 2. This assumes a constant withdrawal angle of the delivery device (described in additional detail herein) of 60 degrees. However, a larger angle increases the tolerance on the withdrawal angle and still ensures the implant hooks or otherwise engages the rear wall of the arteriotomy. The increase in angle between the neck 42*i* and intra-luminal foot section 25*i* may be limited by what will reasonably fit through a loading funnel, which is described in further detail elsewhere herein.

Figure 14:
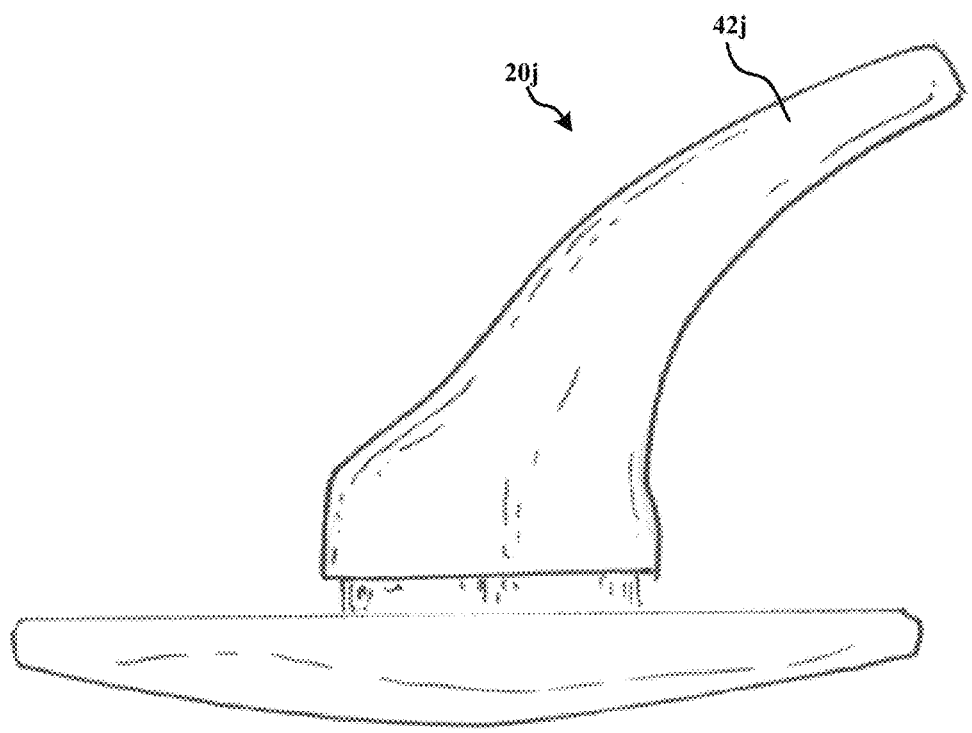
FIG. 14 shows another foot core.

To increase the flexibility of use, for example, another variation is to make the neck flexible. For example, FIG. 14 shows a foot core 20*j* with a flexible neck 42*j*. The neck 42*j* of the implant transitions from a round cross-section at its distal section to an elliptical cross-section at its proximal end. This allows the neck 42*j* to flex during its insertion through the loading-funnel.

Figure 51A:
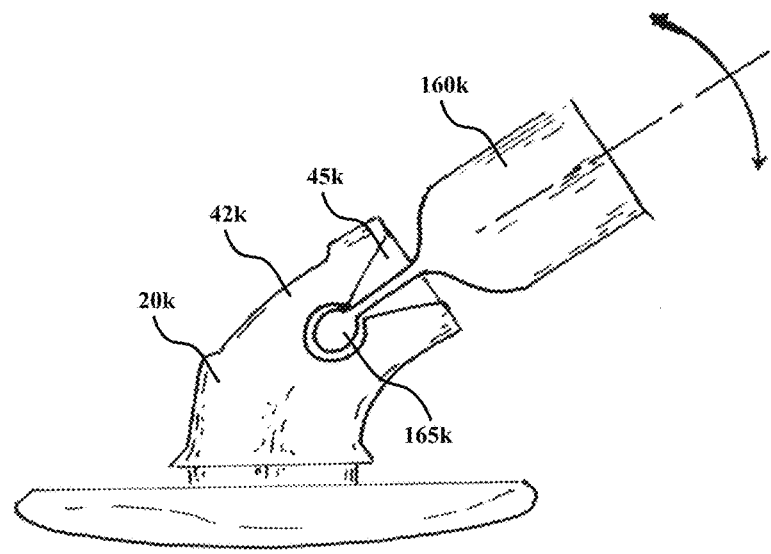
FIG. 51A shows a rotatable interlocking arrangement.
Figure 51B:
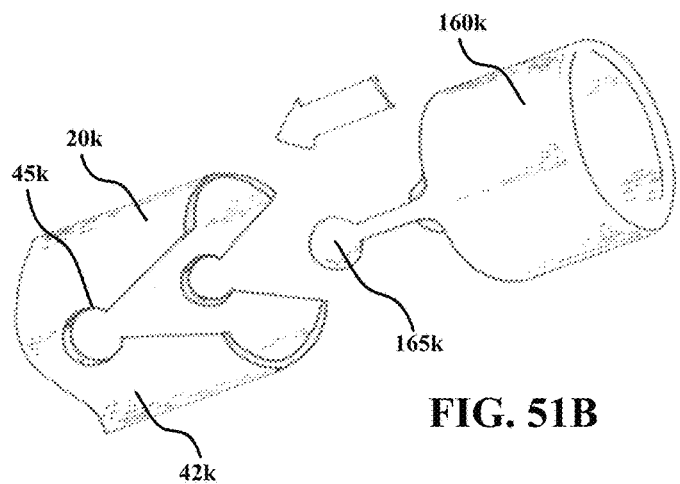
FIG. 51B shows the interlocking arrangement of FIG. 51A in a disengaged state.
Figure 51C:
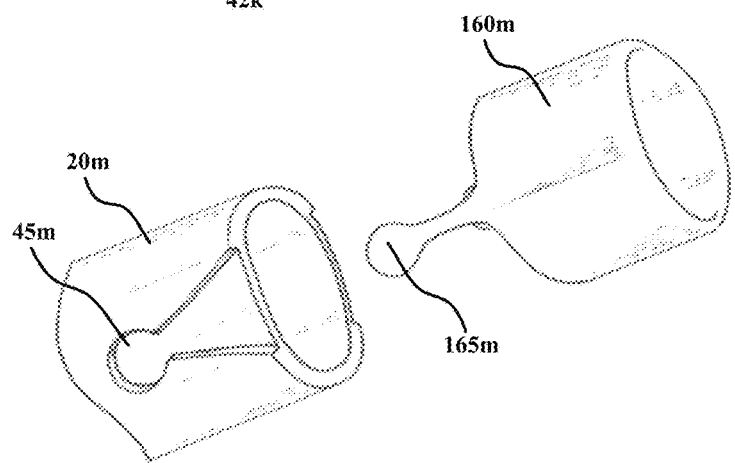
FIG. 51C shows another interlocking arrangement in a disengaged state.

Further variations to that shown in FIG. 14 is to articulate the implant relative to a delivery device as shown in FIGS. 51A to 51C. These configurations allow articulation between the delivery device and the implant. Securement of the implant to the delivery device is achieved by securing paddles or interlock projections 165*k*, 165*m* of retaining tubes 160*k*, 160*m* of a delivery device in place in corresponding interlock recesses 45*k*, 45*m* and preventing them from moving in a lateral direction by providing an external sleeve, such as, e.g. a release sleeve such as release sleeve 175 described in further detail herein.

The configuration of FIGS. 51A and 51B differs from that of FIG. 51C in that the interlock recesses 45*k* of FIGS. 51A and 51B extend laterally entirely though the wall of the neck 42*k*, whereas the recess 45*m* of FIG. 51C does not.

Figure 15A:
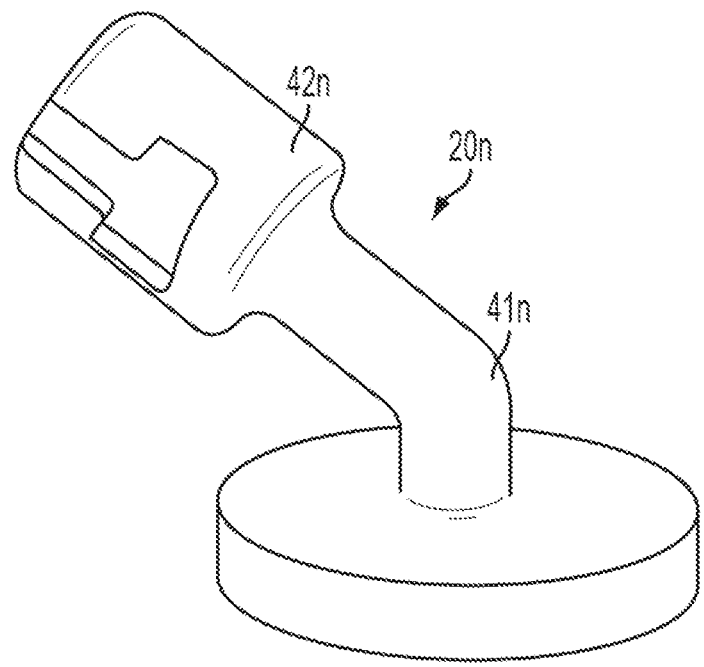
FIG. 15A shows a foot core having a flexible neck.
Figure 15B:
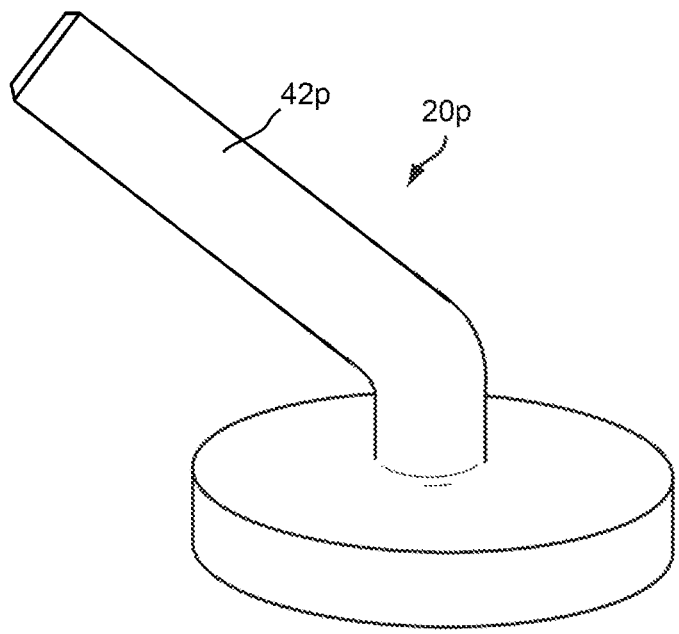
FIG. 15B shows another foot core having a flexible neck.

Further variations to impart flexibility to the implant neck is shown in FIGS. 15A and 15B. Here, the flexibility is imparted via a reduced cross section in at least a portion of the neck 42*n*, 42*p*. The configuration of FIG. 15A differs from that of FIG. 15B in that FIG. 15A has a reduced cross-sectional geometry in only a portion its extra-luminal portion, whereas the configuration of FIG. 15B has a constant narrow cross sectional geometry along its extra-luminal portion.

Figure 51D:
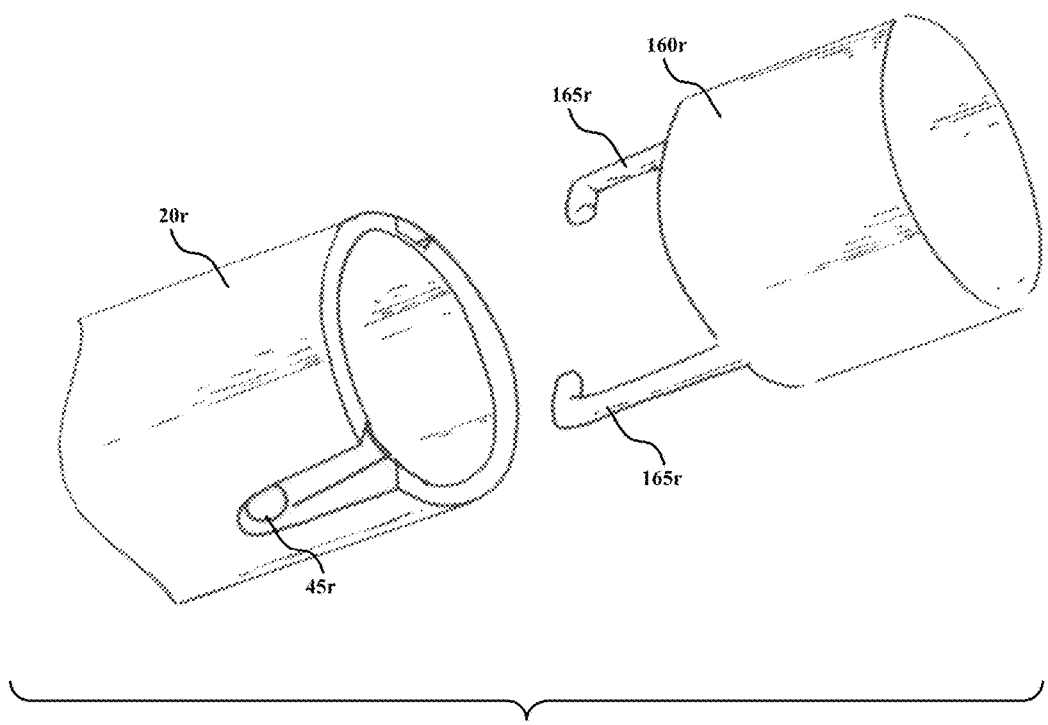
FIG. 51D shows another interlocking arrangement in a disengaged state.

FIG. 51D shows a variation on the attachment of the implant to the delivery device. In particular, the interlock projections 165*r* of the retaining sleeve 160*r* have hooked portions that extend laterally inwardly to engage recesses 45*r*.

Figure 16:
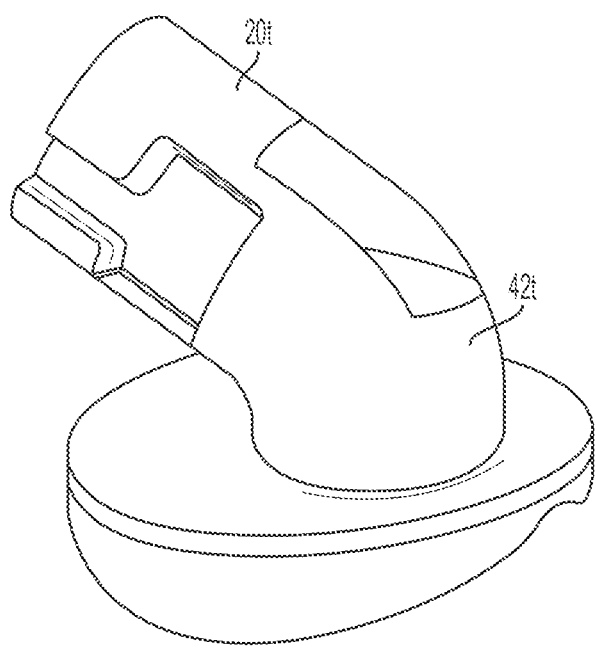
FIG. 16 shows a foot core that does not include a wing-receiving recess.

FIG. 16 shows a further embodiment of the foot core. This configuration differs in that the foot core 20*t* has no retaining feature to secure the flexible-wing to the foot core 20*t*. That is, the foot core 20*t* does not have a recess or any other particular mechanism configured to retain the wing 60 on the foot core 20*t*. In this example, the flexible wing 60 may be secured by an interference fit between the foot core's neck 42*t* and the central opening 65 within the flexible wing 60. This may facilitate the assembly of the flexible wing 60 onto the foot core 20*t*.

Referring to FIGS. 17A to 17C, a further variation of this concept is to assemble the flexible wing 60 onto the neck 42*u* of the foot-core 20*u* and then secure the wing 60 in place by the addition of a through pin or the further assembly of a collar 195*u* with an interference fit between the collar 195*u* and foot core's neck 42*u*. The collar 195*u* may further be secured by one or more projections configured to engage with corresponding one or more recesses in neck section 42*u*.

Figure 18:
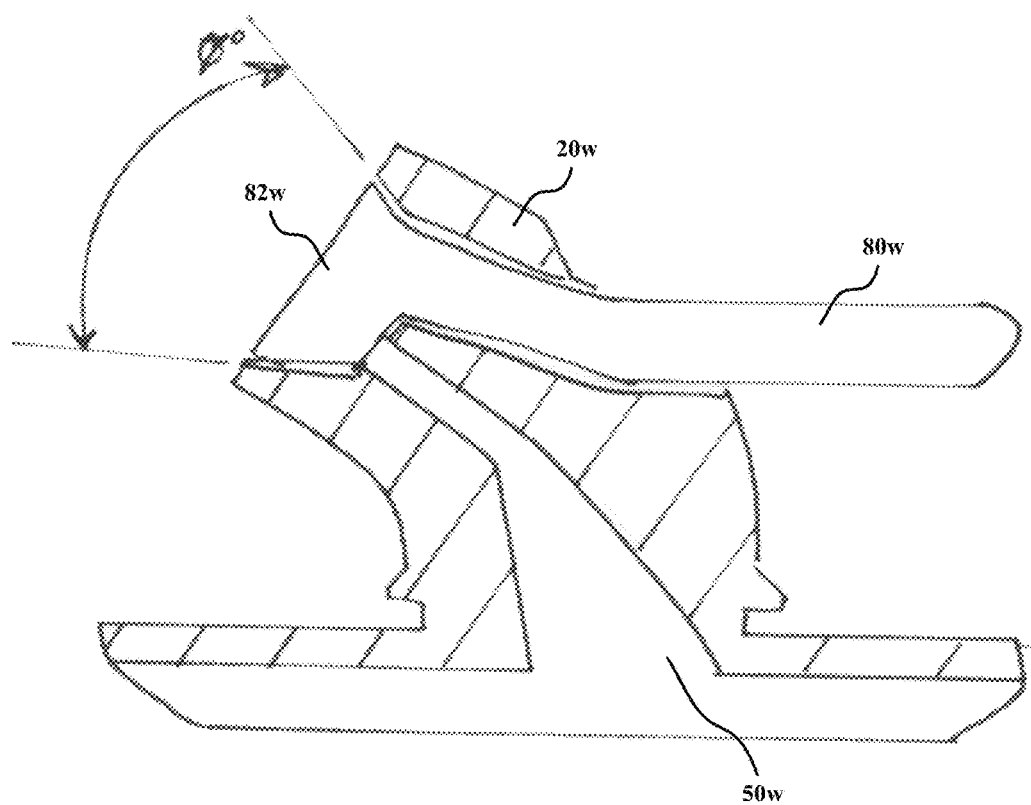
FIG. 18 is a sectional side view of a foot core and an intra-luminal pin.
Figure 19:
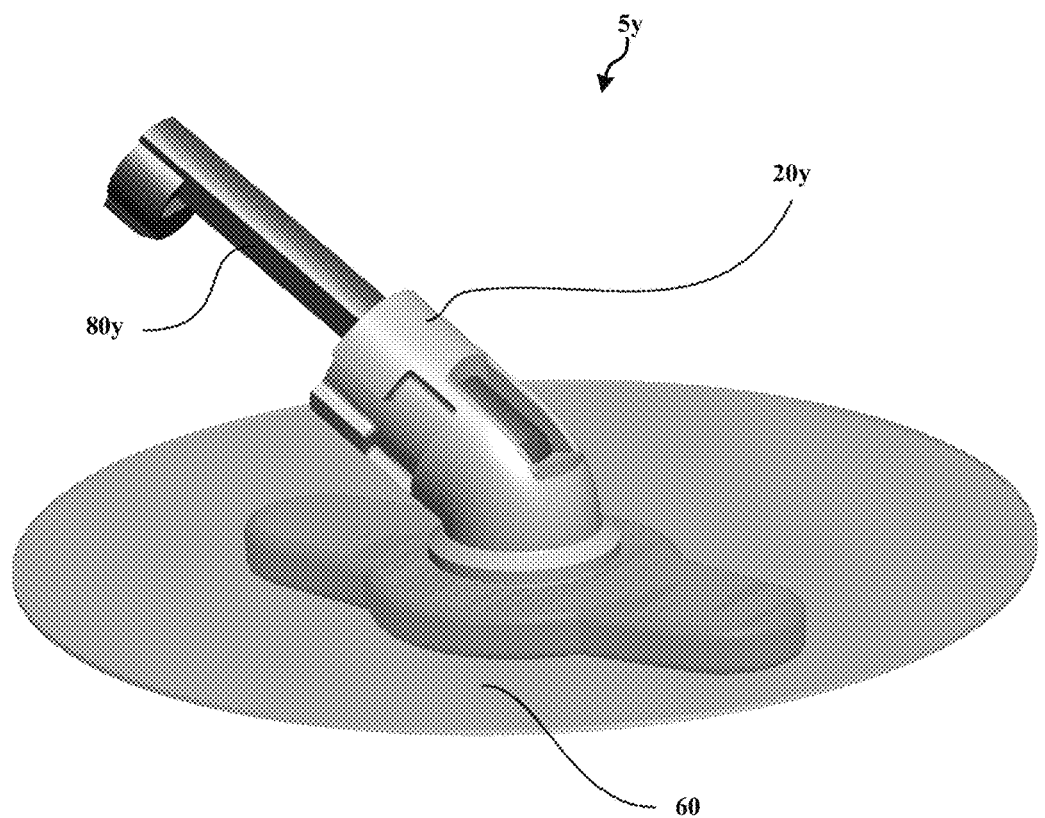
FIG. 19 shows an implant.
Figure 20:
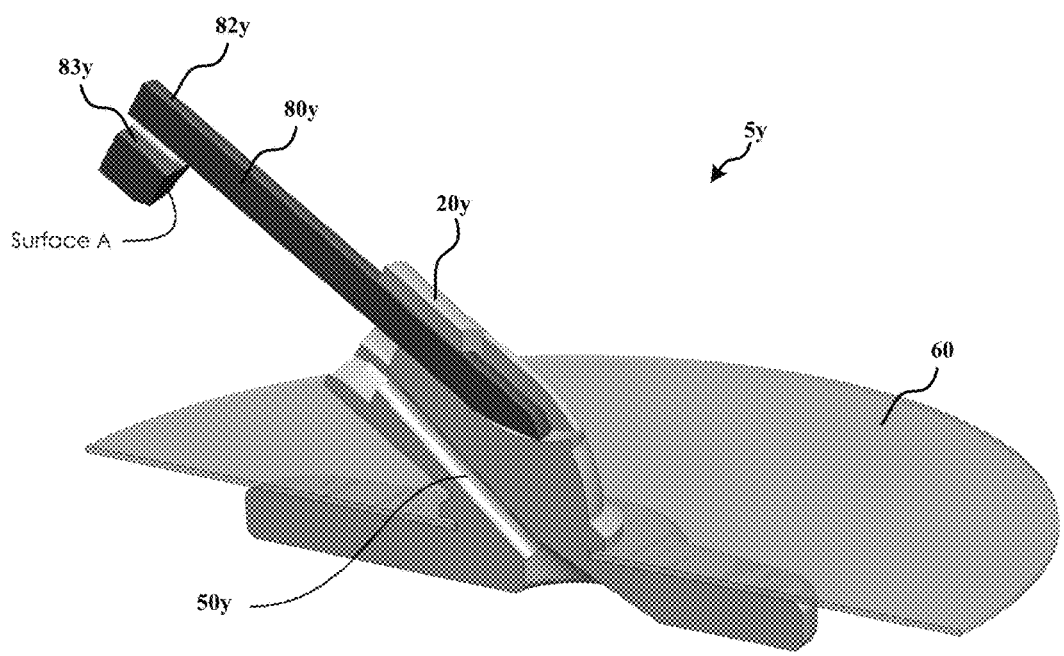
FIG. 20 is a perspective view of a cross-sectioned implant of FIG. 19.

FIG. 18 provides another extra-luminal pin 80*w*. In this example, an additional feature to secure the extra-luminal pin 80*w* within the foot core 20*w* is to incorporate a taper lock when the enlarged proximal or rear portion 82*w* of the extra-luminal pin 80*w* engages with the foot core 20*w*.

The conical taper lock between the extra-luminal pin 80*w* and the foot core 20*w* relies, in this example, on the foot core taper being at a lesser angle than the taper on the mating surfaces of the extra-luminal pin 80*w*. This taper-lock not only enhances the lock between the two components 80*w*, 20*w* once positioned relative to each other, but also improves the potential fluid seal between the two components with respect to sealing the guidewire channel 50*w*.

Referring to FIGS. 19 to 27, a further closure device or implant 5*y* includes all of the features of the other closure devices, e.g. closure device 5, except to the extent indicated otherwise.

Figure 3A:
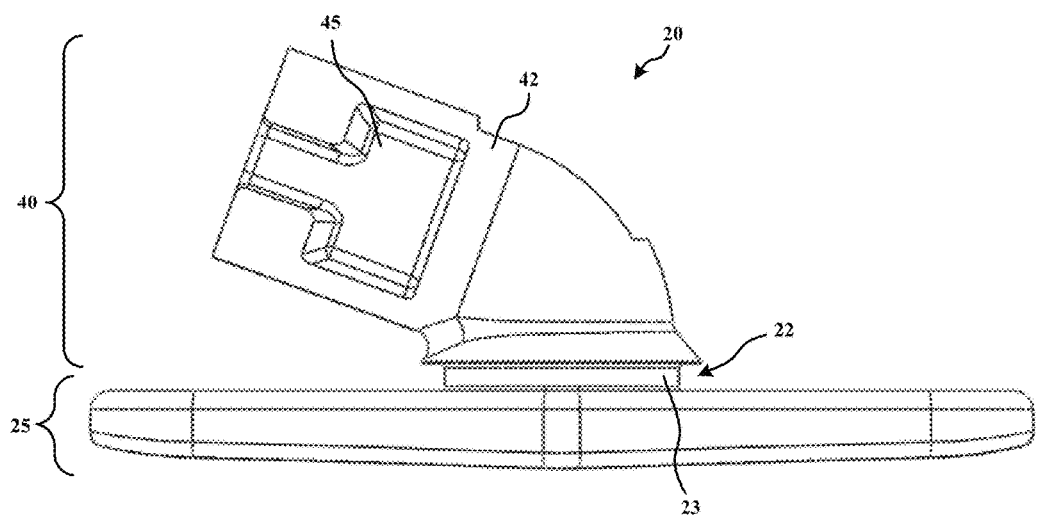
FIG. 3A shows a right side view of a foot core of the closure device shown in FIG. 1A.
Figure 3B:
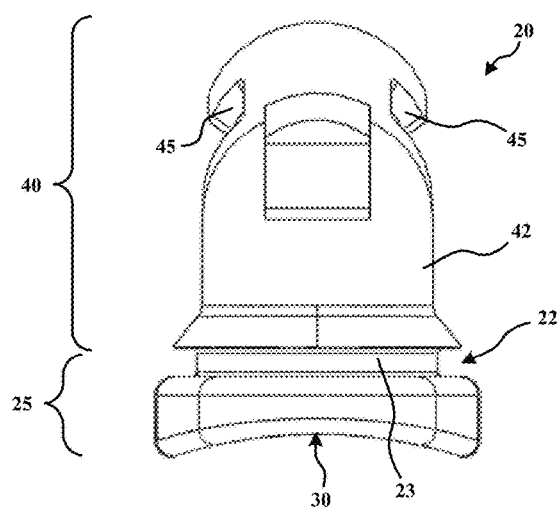
FIG. 3B shows a front view of the foot core shown in FIG. 3A.
Figure 3C:
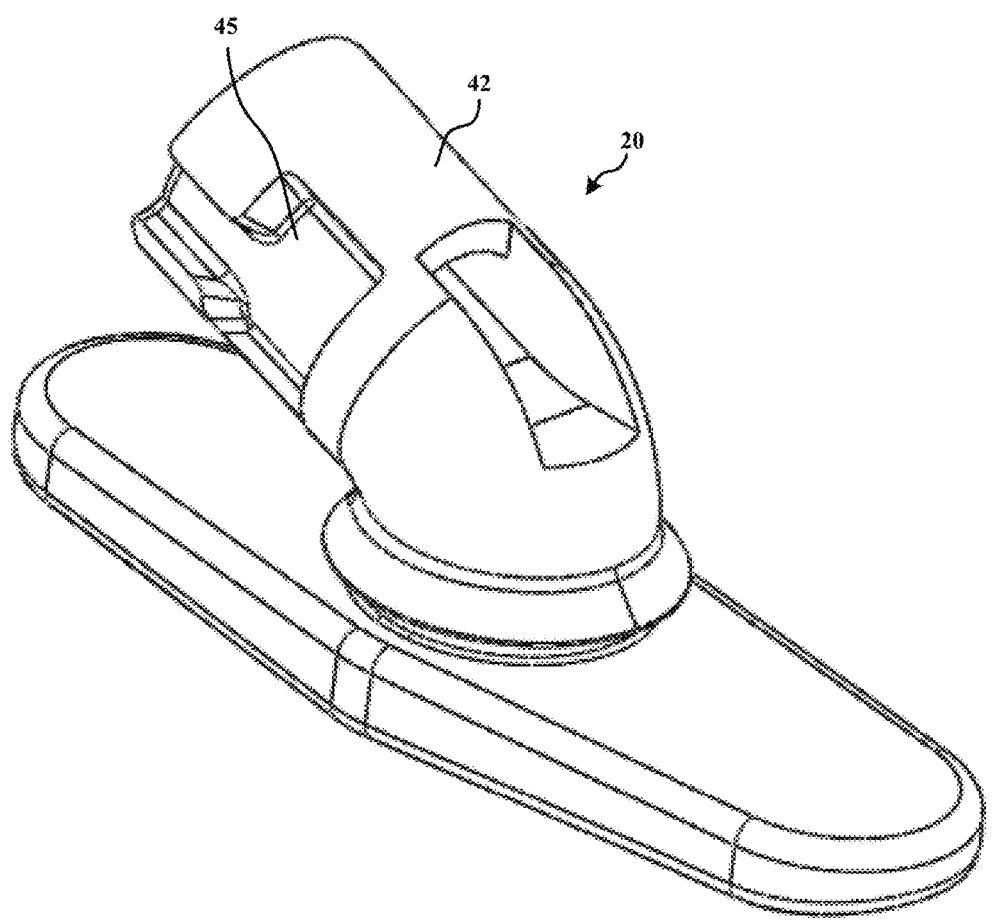
FIG. 3C shows a perspective view of the foot core shown in FIG. 3A.
Figure 3D:
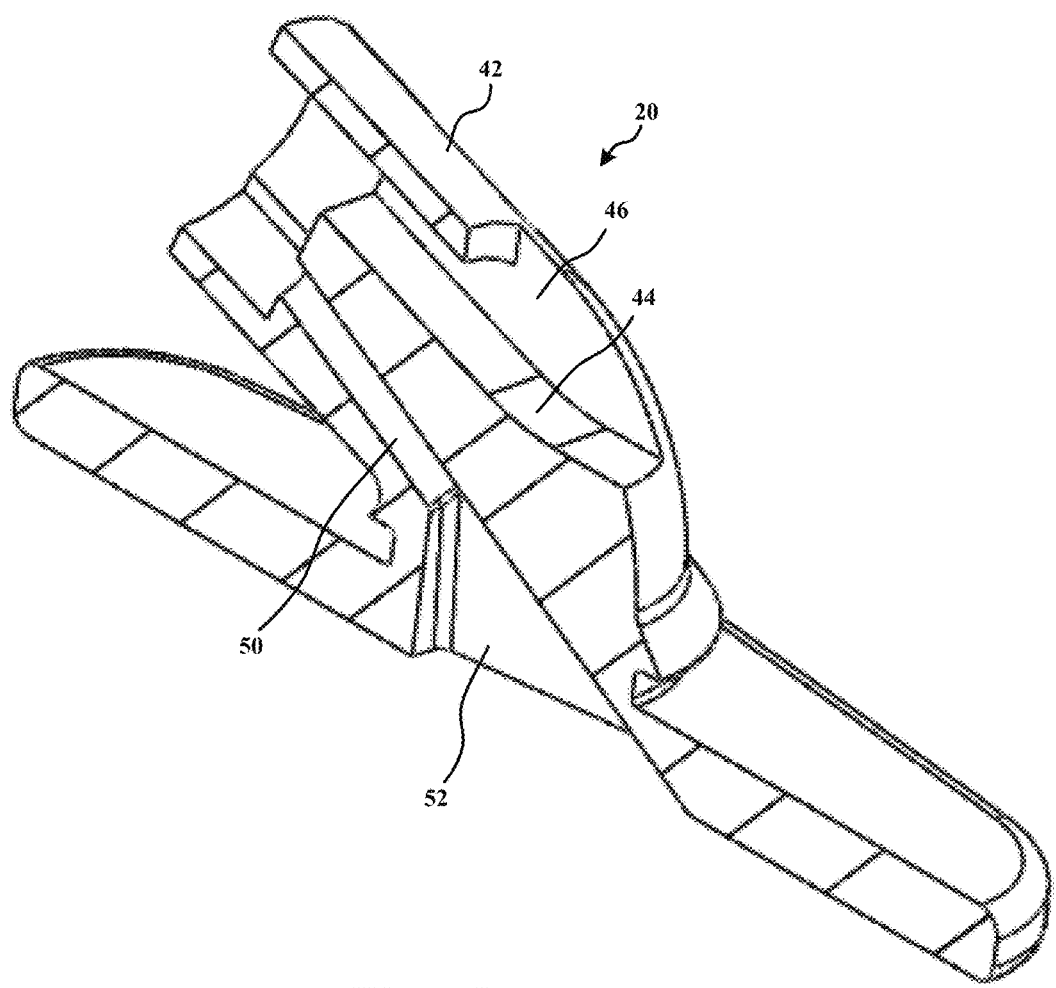
FIG. 3D shows a cross-sectional perspective view of the foot core shown in FIG. 3A.
Figure 4A:
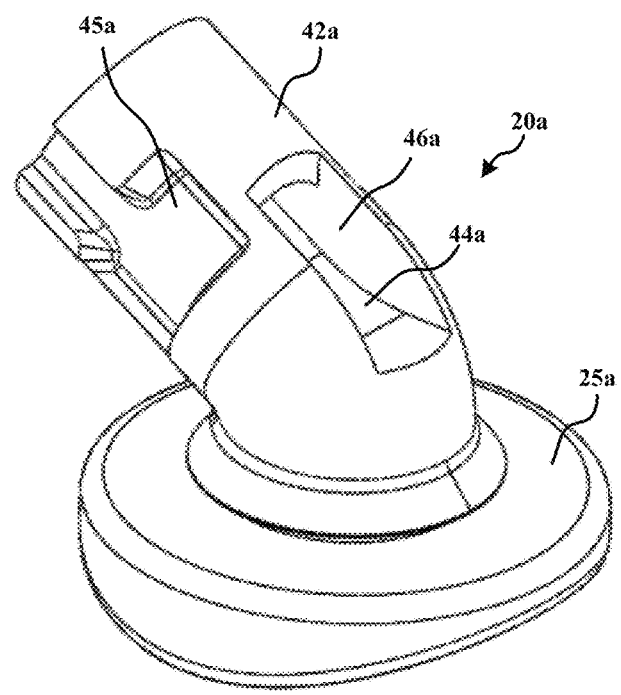
FIG. 4A shows a perspective view of another foot core.
Figure 4B:
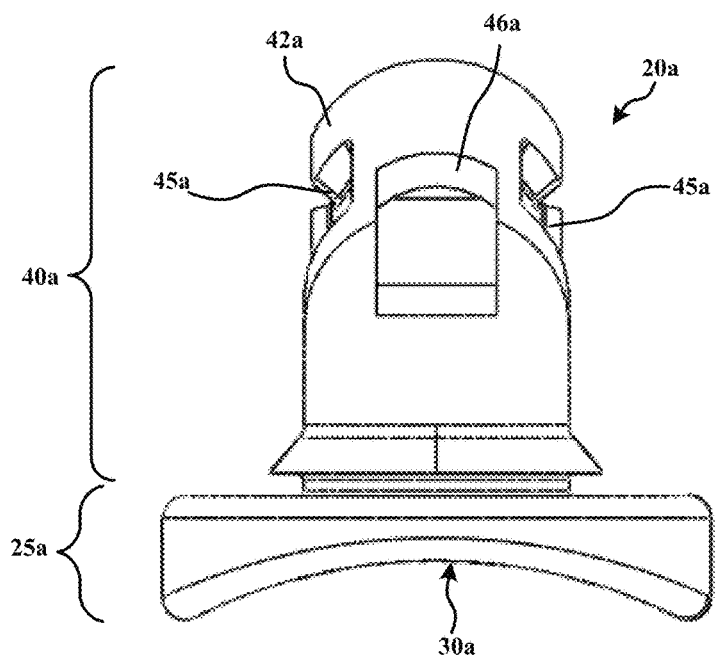
FIG. 4B shows a front view of the foot core shown in FIG. 4A.
Figure 4C:
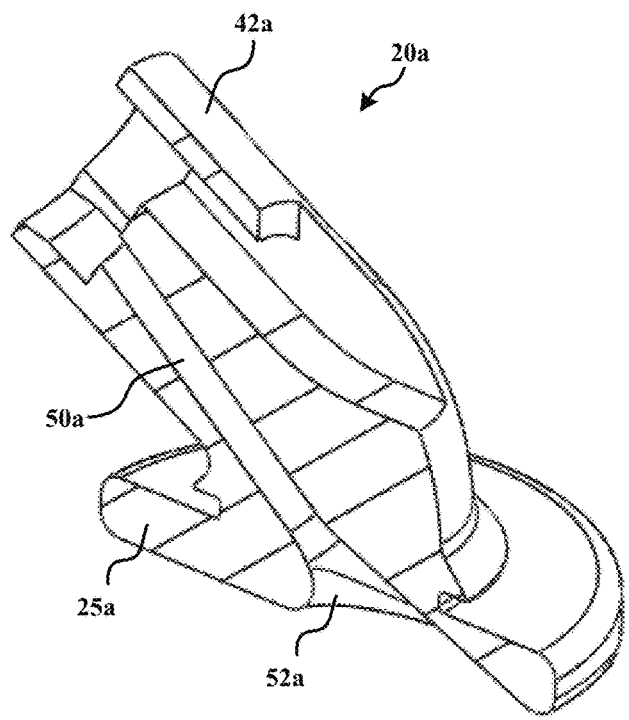
FIG. 4C shows a cross-sectional perspective view of the foot core shown in FIG. 4A.
Figure 4D:
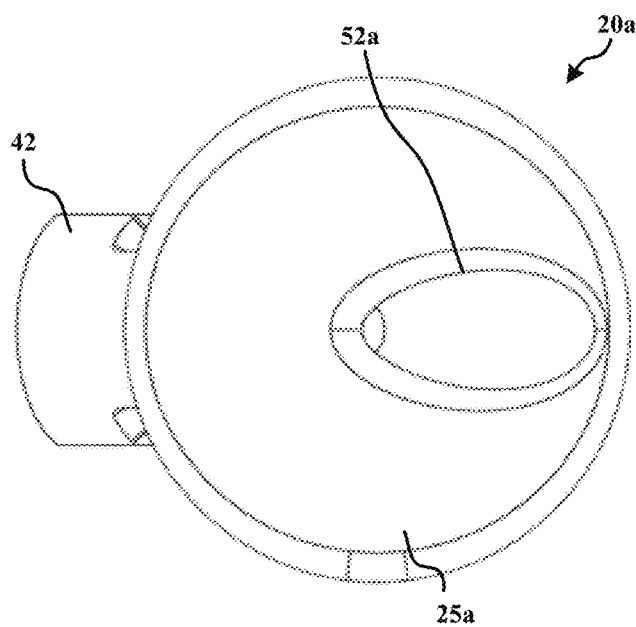
FIG. 4D shows a bottom view of the foot core shown in FIG. 4A.
Figure 4E:
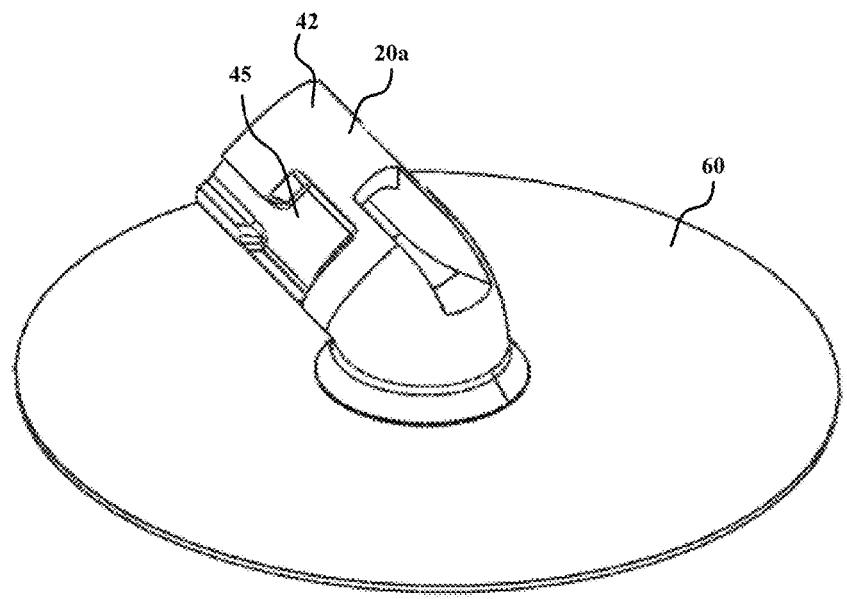
FIG. 4E shows a perspective view of the foot core shown in FIG. 4A and a wing element.
Figure 4F:
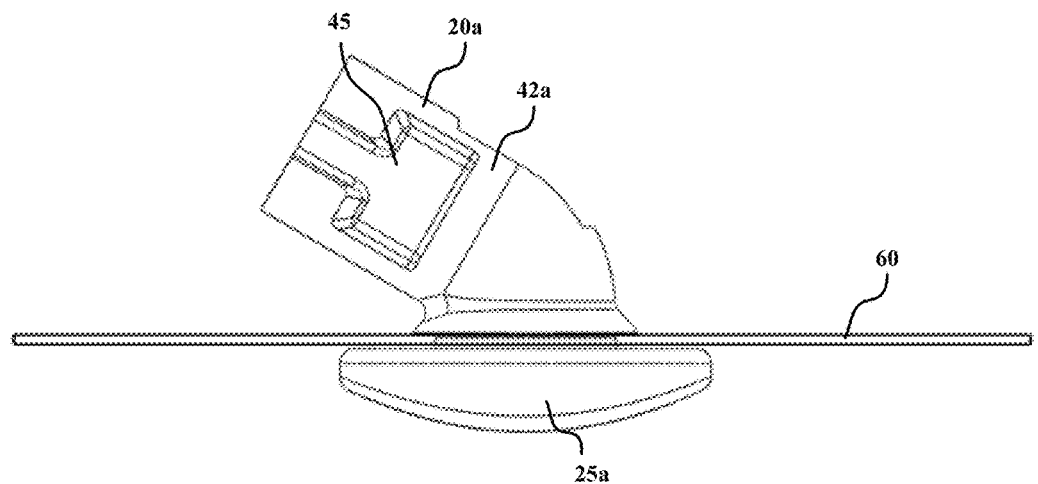
FIG. 4F shows a right side view of the foot core and wing element shown in FIG. 4E.
Figure 27:
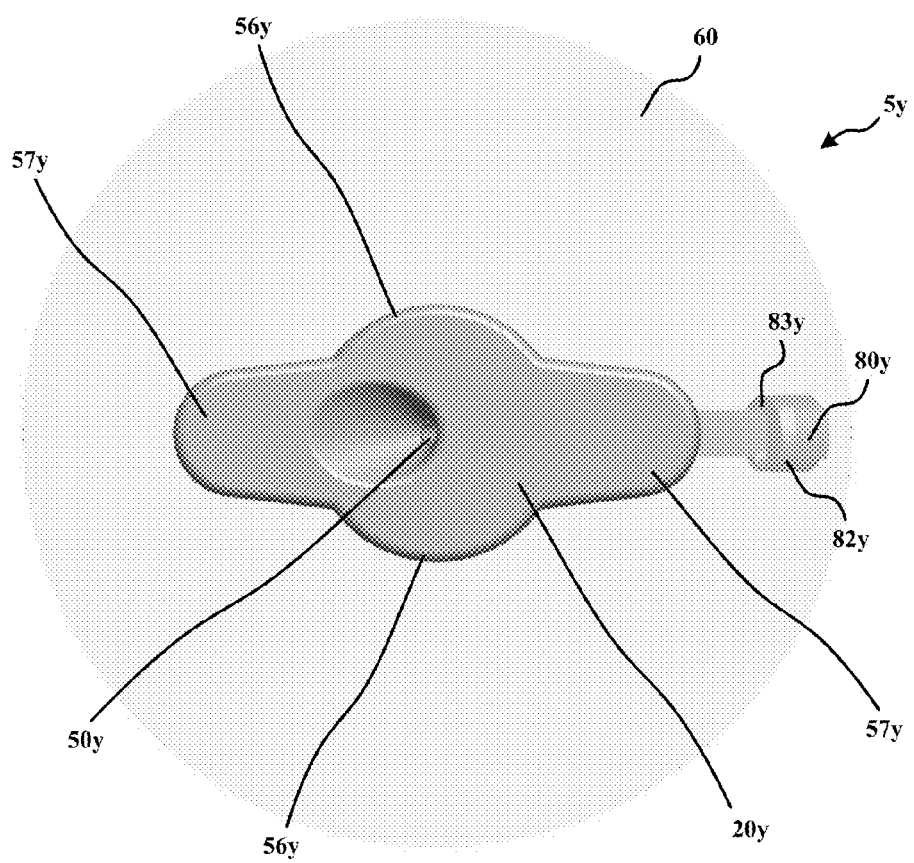
FIG. 27 is a bottom view of the implant of FIG. 19.

The closure device 5*y* includes a foot core 20*y* having a profile that is "hybrid" in that it shares geometric features with both a round foot core, such as, e.g. the foot core 20*a* shown in FIG. 4A, and an elongated foot core, such as, e.g. the elongated foot core 20 shown in FIG. 3C. Referring for example, to FIG. 27, the hybrid foot core 20*y* has rounded portions 56*y* and projecting portions 57*y*.

The rounded portions 56*y* extend around the portion of the foot core 20*y* that extends through the flexible wing 60 to provide increased lateral surface area of the foot core 20*y*, adjacent the opening in the wing 60 and the arteriotomy to be sealed. This region of increased lateral surface area provides for a greater sealing between, e.g. the foot core 20*y* and the wing 60.

The projecting portions 57*y* give the intra-luminal portion of the hybrid foot core 20*y* an elongated shape. This elongated shape further limits the ability of the foot core from being inadvertently pulled back through the arteriotomy when the operator is setting the closure device 5*y* in into its implanted position.

Thus, the hybrid foot core 20*y* may provide the sealing advantages of a wide or rounded foot core as well as the setting benefits of an elongated foot core.

The geometry of the hybrid foot core 20*y* provides support to the artery in both a longitudinal direction and transverse direction. Although the foot core 20*k* has a circular central region, it should be understood that any suitable widened geometry, e.g. oval, square, rectangular and/or polygonal, with rounded and/or sharp corners. This central region provides a flaring out of the profile of the intra-luminal portion of the foot core 20*k* in the region where the neck of the foot core 20*k* passes through the flexible wing 60.

Figure 21:
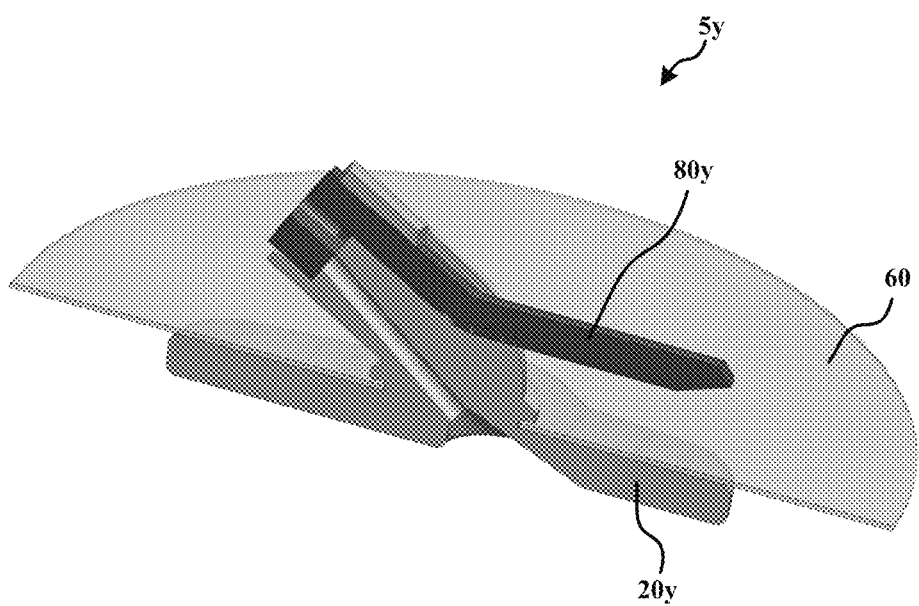
FIG. 21 is a perspective view of a cross-sectioned implant of FIG. 19 with an extra-luminal pin in a deployed position.
Figure 22A:
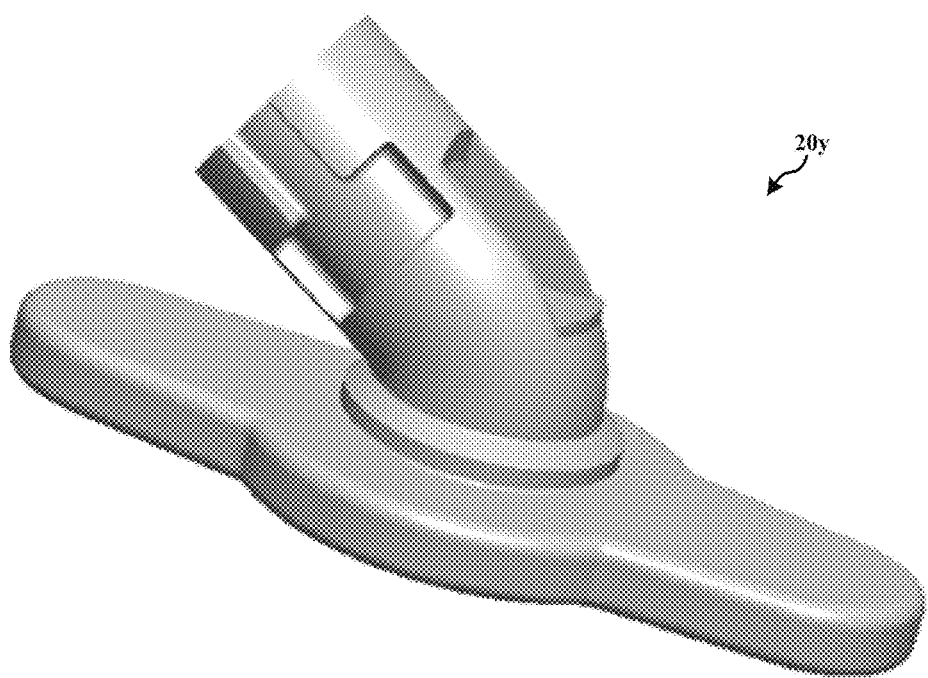
FIG. 22A shows a foot core of the implant of FIG. 19.
Figure 22B:
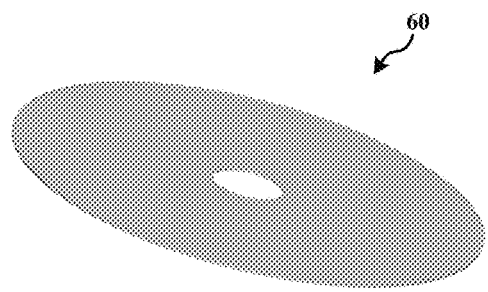
FIG. 22B shows a flexible wing of the implant of FIG. 19.
Figure 22C:
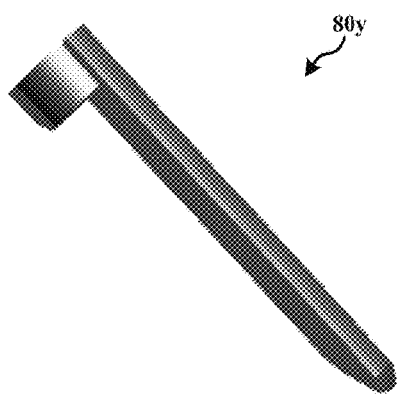
FIG. 22C shows an extra-luminal pin of the implant of FIG. 19.
Figure 23:
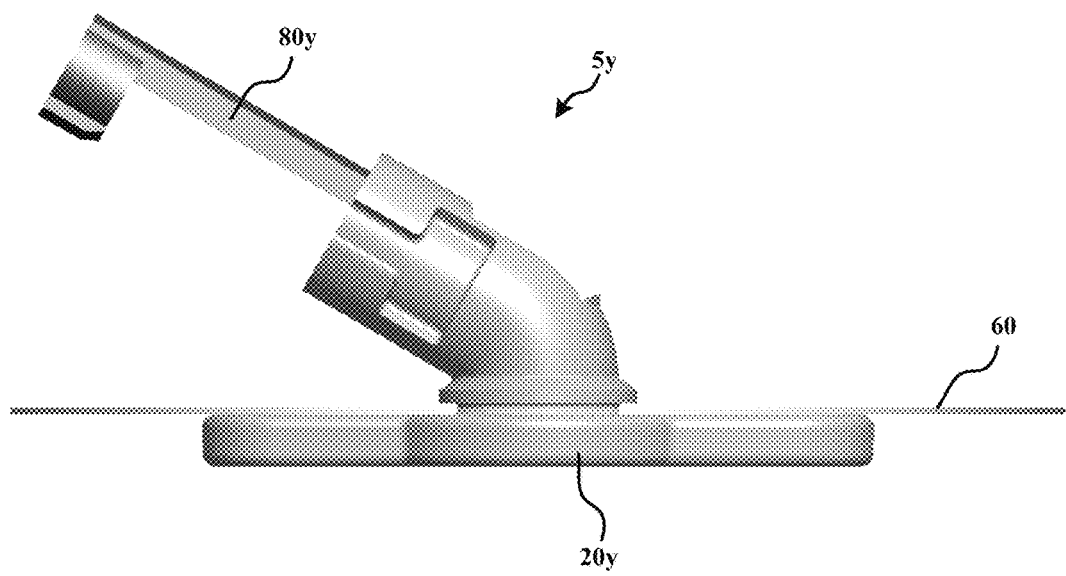
FIG. 23 is a side view of the implant of FIG. 19.
Figure 24:
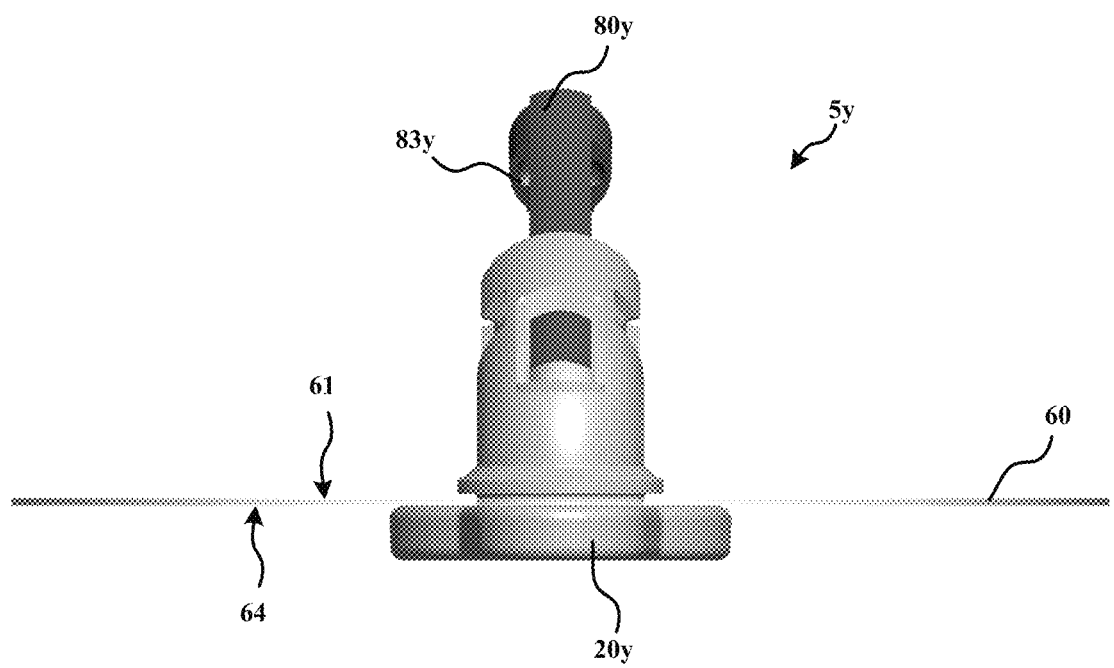
FIG. 24 is a front view of the implant of FIG. 19.

In a manner analogous to that of the device 5 illustrated, e.g. in FIGS. 7A and 7B, the pin 80*y* may be used to occlude the guidewire hole within the foot core 20*y* when deployed, e.g. in a configuration such as illustrated in FIG. 21. When deployed, as illustrated, e.g. in FIG. 21, an enlarged proximal portion 82*y* of the extra-luminal pin 80*y* blocks the guidewire port or channel 50*y*. In its proximal or retracted position, the pin 80*y* allows the guidewire to pass through channel 83*y* in the enlarged proximal portion 82*y*. When the pin 80*y* is moved into its distal or extended position, the channel 83*y* does not align with the channel 50*y* in the foot core 20*y*, thereby blocking the channel 50*y*. In the proximal or retracted position, the guidewire is able to pass through both channels 50y and 83y since the channels 50y and 83y are sufficiently axially spaced apart.

Figure 25:
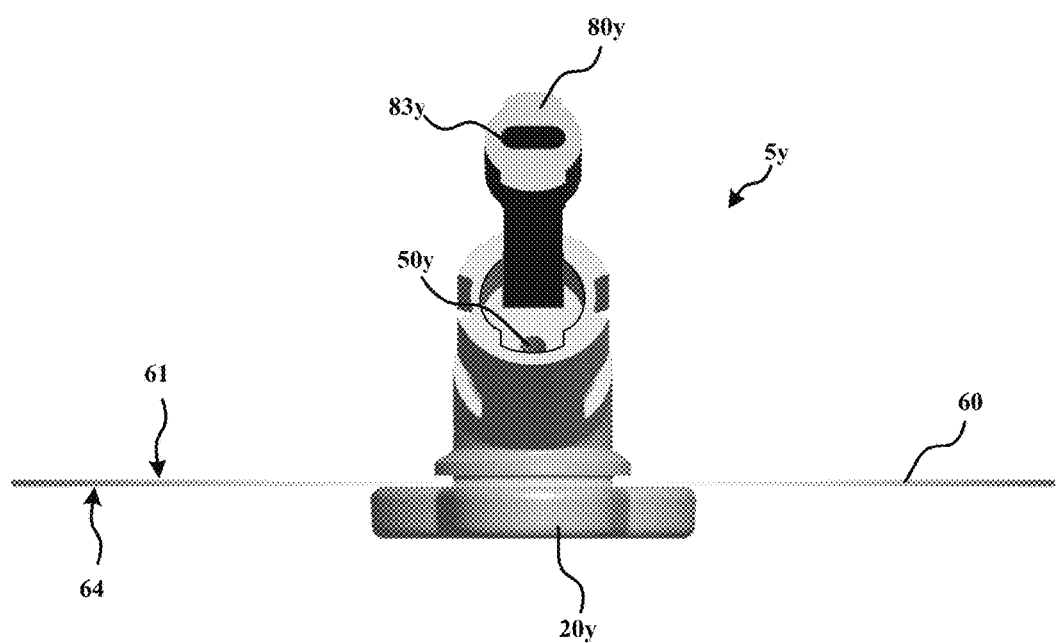
FIG. 25 is a back view of the implant of FIG. 19.
Figure 26:
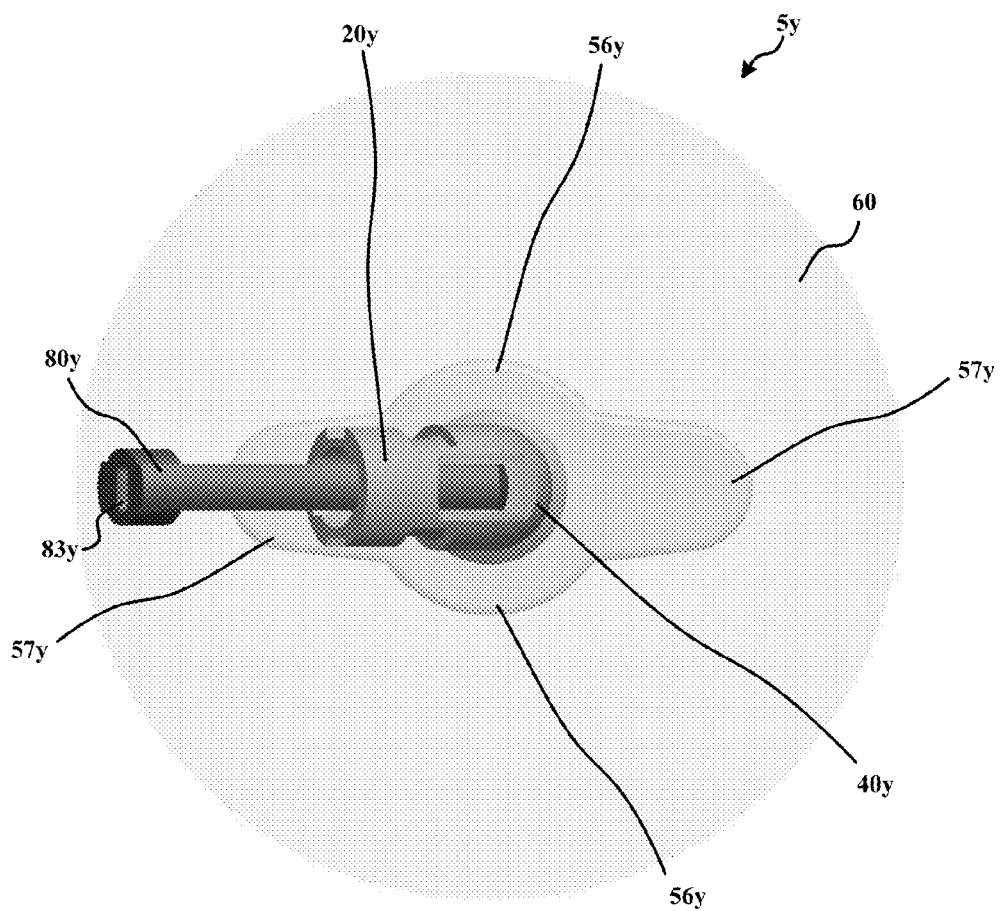
FIG. 26 is a top view of the implant of FIG. 19.

Referring, for example, to FIG. 25, the channel 83y in the pin 80y is elongated to allow for increased freedom of movement of the guidewire within the channel 83y.

Figure 28A:
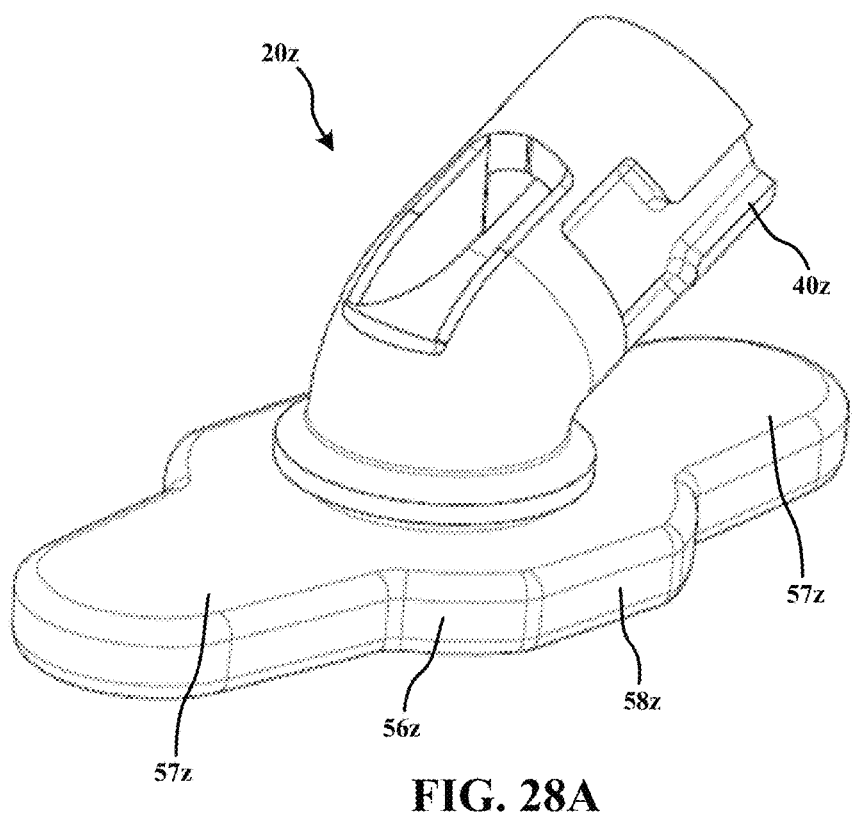
FIG. 28A shows a front perspective view of a foot core.
Figure 28B:
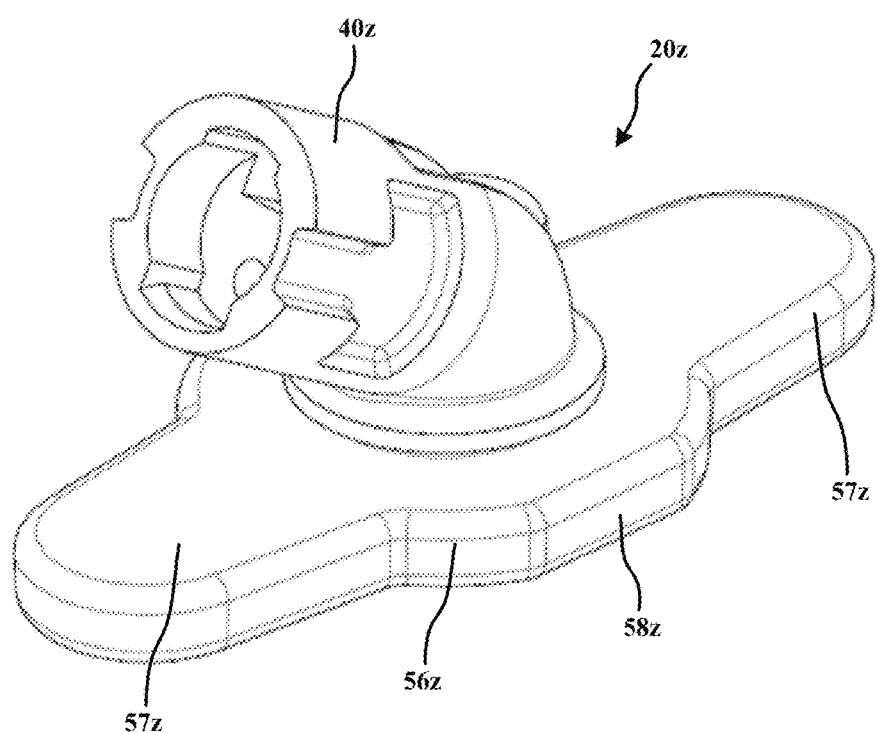
FIG. 28B shows a rear perspective view of the foot core of FIG. 28A.
Figure 28C:
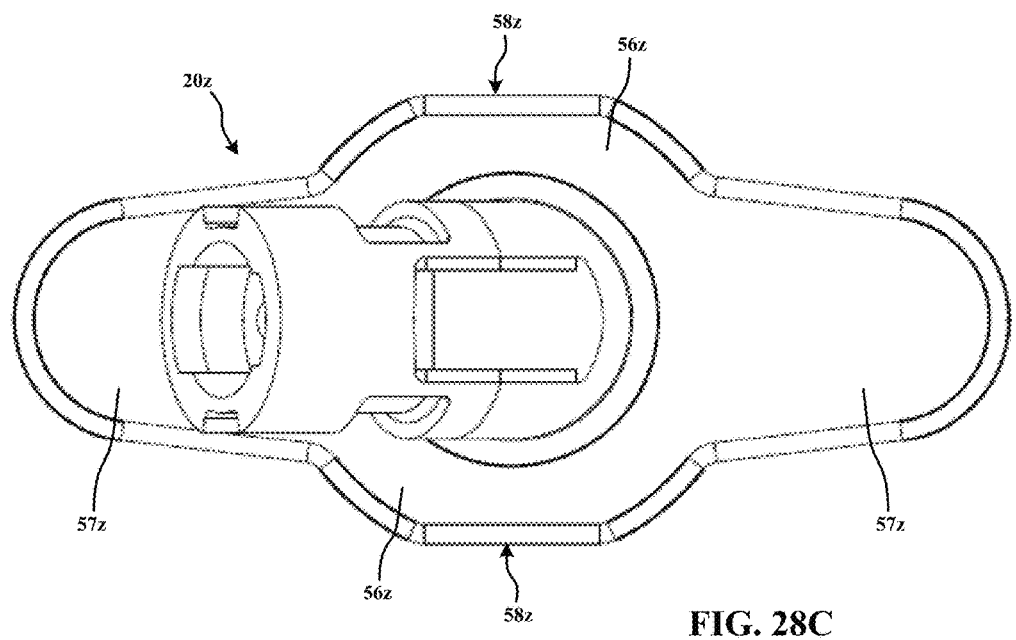
FIG. 28C shows a top view of the foot core of FIG. 28A.
Figure 28D:
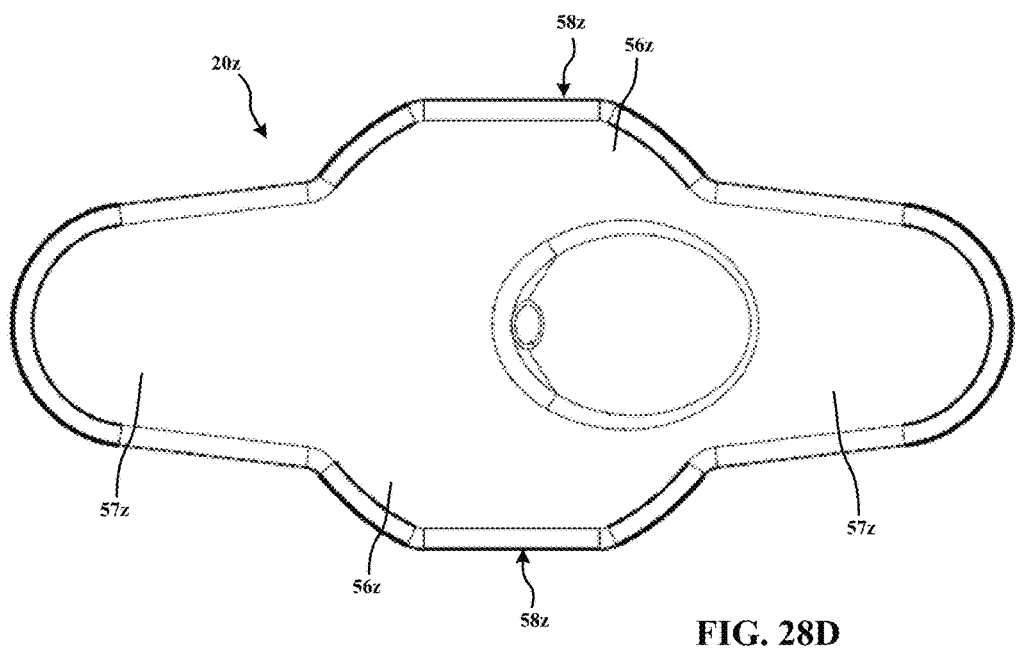
FIG. 28D shows a bottom view of the foot core of FIG. 28A.
Figure 28E:
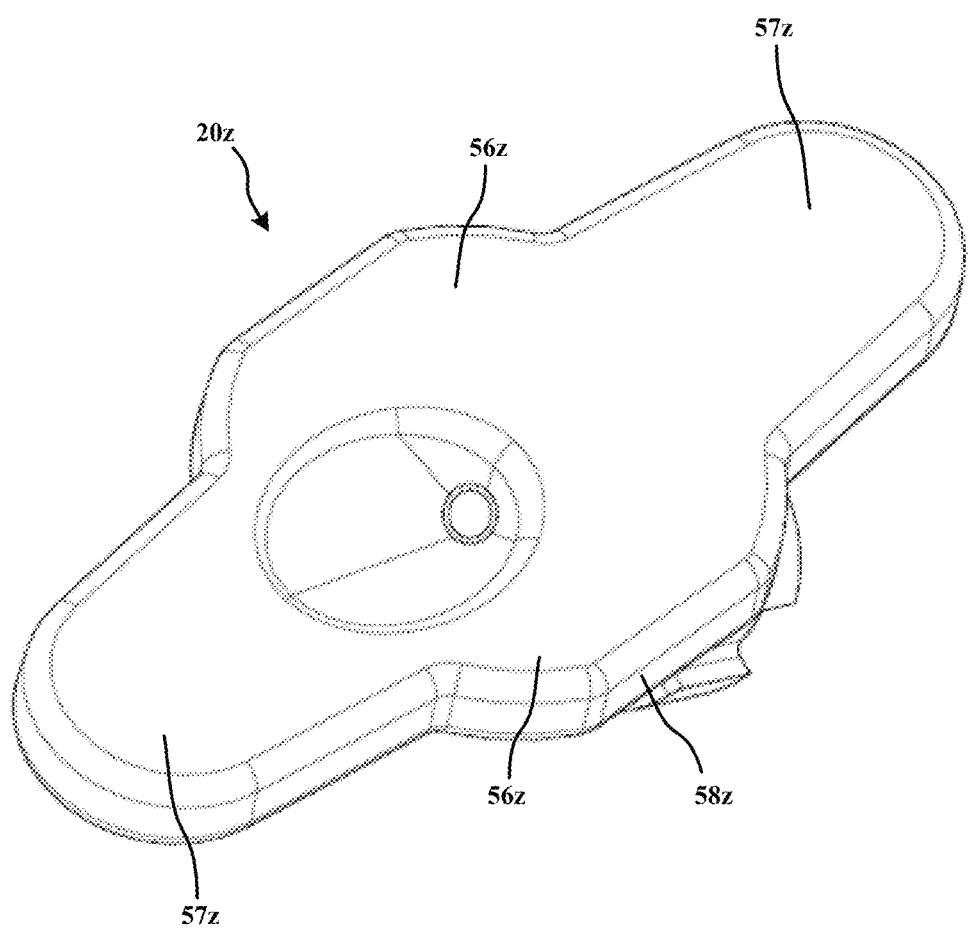
FIG. 28E shows a perspective view of the bottom of the foot core of FIG. 28A.

FIGS. 28A to 28B show a front perspective view of a foot core 20z that differs from the foot core 20y in that the lateral portions 56z are partially flattened to provide a reduced width. This flattening or facing results in two flat surfaces 58z. By reducing the width of the foot core 20z relative to the foot core 20y, greater clearance is provided between the foot core 20z and the loading funnel 396 or loading cannula 335 described in further detail herein. This allows a larger diameter or thicker flexible wing 60 to be loaded by facilitating more clearance and hence, a larger amount of the flexible wing 60 to overlap within the loading funnel and loading cannula thereby reducing the potential for premature and unfavorable interaction between the footcore and overlapping flexible wing.

Nevertheless, the foot core 20z may provide similar benefits to the rounded portions 56y due to the lateral projection of the portions 56z relative to the width of the lateral portions 56z relative to the width of the projecting portions 57z. As with the foot core 20y, this increased width is provided at a location adjacent the location where the extra-luminal portion 40z extends through the aperture in the flexible wing 60.

Thus, the foot core 20z reduces the width of the lateral projections, but only to an extent that does not substantially affect the sealing between, e.g. the foot core 20z and the wing 60.

As with the foot core 20y, the foot core 20z may provide the sealing advantages of a widened or rounded foot core as well as the setting benefits of an elongated foot core.

Figure 29:
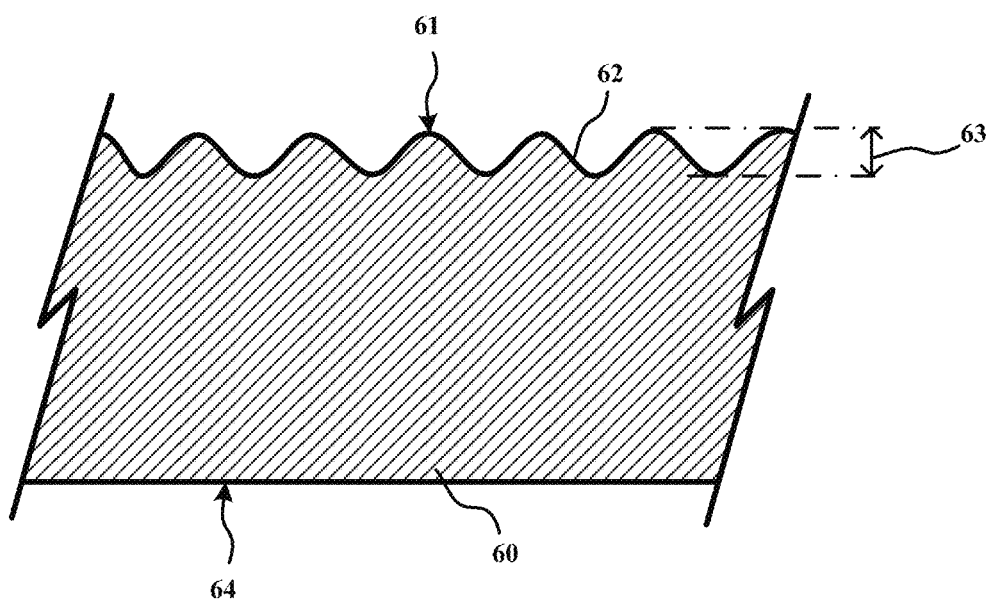
FIG. 29 is a partial sectional view the flexible wing of the implant of FIG. 19.

Referring to FIG. 29, which is not drawn to scale, the wing 60 includes an anterior surface 61, which contacts the luminal surface of the artery when implanted, and a posterior surface 64, which faces the lumen of the artery and the blood flow when implanted.

The anterior surface 61 and/or the posterior surface 64 is provided with an altered wettability, i.e., a change in surface energy from the native, e.g. smooth, surface finish. This change in wettability may be provided in the form of electrical charge, surface texture, protein attachment, mechanical scraping, chemical etching, laser etching and/or other etching, shot blasting (using various shot media), plasma discharge, manufacturing process that encourage functional end groups at the surface, and/or any other suitable form. This change in surface energy encourages cell (or thrombocyte) attachment or adhesion directly or via protein attachment, extracellular matrix and/or adhesion molecule to the luminal surface of the flexible-wing or, conversely, discourage cell or protein attachment. In the illustrated example, the wettability of the anterior surface 61 is increased in order to encourage attachment or adhesion. Cellular attachment or platelet aggregation on the luminal surface 61 of the flexible wing 60 aids and expedites sealing as well as anchoring the intra-arterial implant. This change in surface energy also encourages the adhesion, via a change to the surface tension of the modified material, to the surrounding soft tissue.

Referring to example embodiment of FIG. 29, the anterior surface 61 of the wing 60 is roughened, e.g. abraded, to created grooves or channels 62 having a depth 63 on the order of, for example, 1-100 μm. In some examples, the depth may be on the order of 7-10 μm. It should be understood, however, that the depth 63 may fall within a substantially larger, smaller, and/or different range. The area of abrasion may be continuous or provided in a patterned arrangement. These channels or grooves 62 facilitate cell attachment (e.g. leukocytes, erythrocytes and particularly thrombocytes) and aggregation. As indicated above, this aggregation of cells promotes thrombogenesis which also forms an attachment to the luminal wall of the artery above the wing 60. This cellular attachment to both the artery wall and anterior surface of the wing 60 may act as a secondary seal. The cellular attachment to the surface 61 of the wing 60 may occur, for example within seconds of the wing 60 being implanted.

The posterior surface 64 is relatively flat in the illustrated example. It should be understood, however, that the posterior surface 64 may be provided with a texture in some example embodiments. Further the posterior surface 64 may be provided with any other mechanism of altered wettability, either increased or decreased, as may be suitable.

Delivery System for Delivering the Closure Device

The closure device 5 is designed to be delivered into the artery 2, or other suitable location, via the procedural sheath 100 used in the interventional procedure over a guidewire 150 in the illustrated examples. Hence, the delivery sequence may start with the sheath 100 and guidewire 150 in situ within the vessel 2. The procedural sheath 100 of the illustrated example includes a hub 110 containing a valve and typically a side arm 120, as illustrated, e.g. in FIG. 30. In particular, FIG. 30, shows an 18 F introducer sheath 100 having hub 110 with valves and side-arm 120.

The side arm 120 may be used, for example, to inject contrast to confirm the position of the sheath 100 relative to the arteriotomy or pressured saline to prevent the sheath 100 from back filling with blood. The valve assembly within the hub 110 is provided to allow the introduction of devices of varying diameters into the sheath 100 and prevents blood loss through the rear of the sheath 100. The guidewire 150, which extends through the longitudinal lumen of the sheath 100, is provided as a safety feature which allows percutaneous re-access to the arterial lumen as a contingency if needed.

Figure 31A:
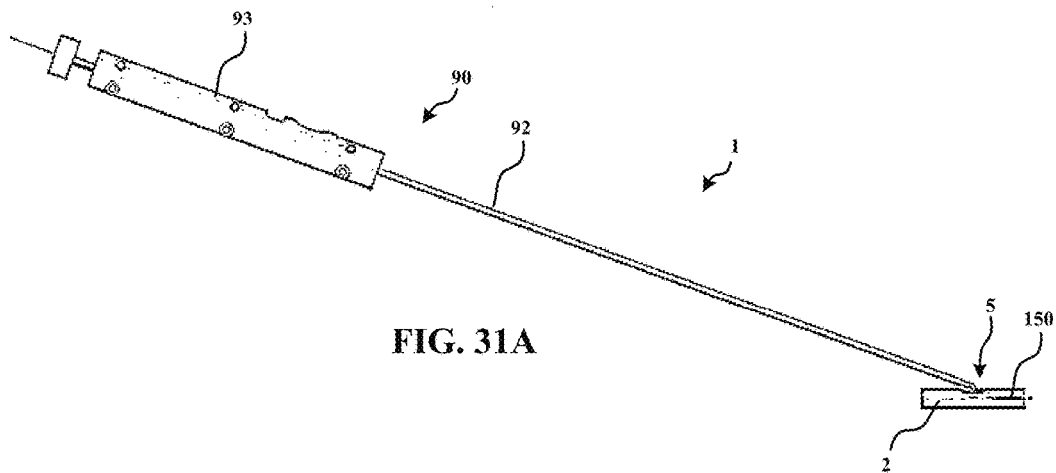
FIG. 31A shows a right side view of a delivery system for implanting the closure device of FIG. 1A.
Figure 31B:
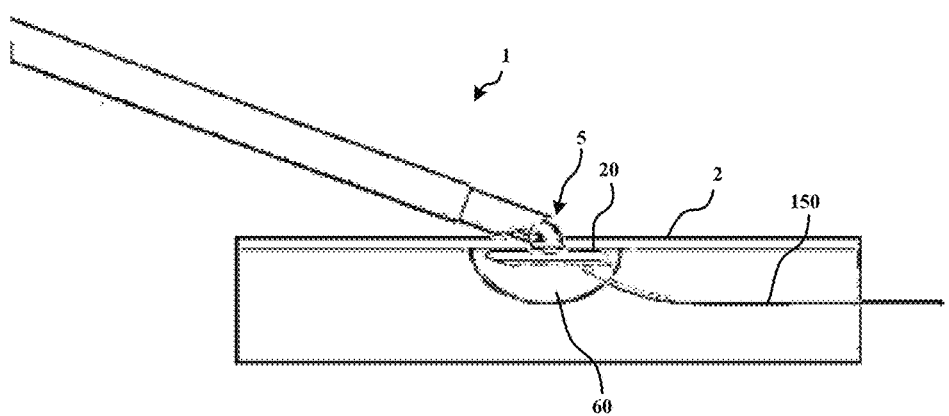
FIG. 31B is an enlarged view of section A of FIG. 31A.

Referring to FIGS. 31A and 31B, a delivery system 1 includes a delivery device 90. The delivery device 90 has a handle 93 at its proximal end and a flexible shaft 92, which attaches to the implant 5 at the distal end. FIGS. 31A and 31B show the implant attached at distal end of the delivery device and within artery 2.

Figure 33A:
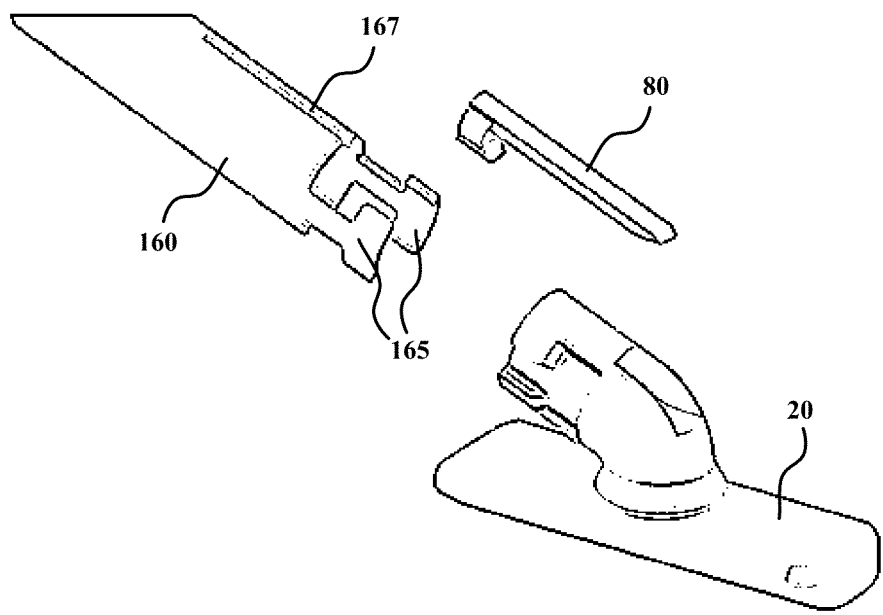
FIG. 33A is an exploded perspective view showing a retaining sleeve, foot core, and extra-luminal pin of the system of FIG. 31A.
Figure 33B:
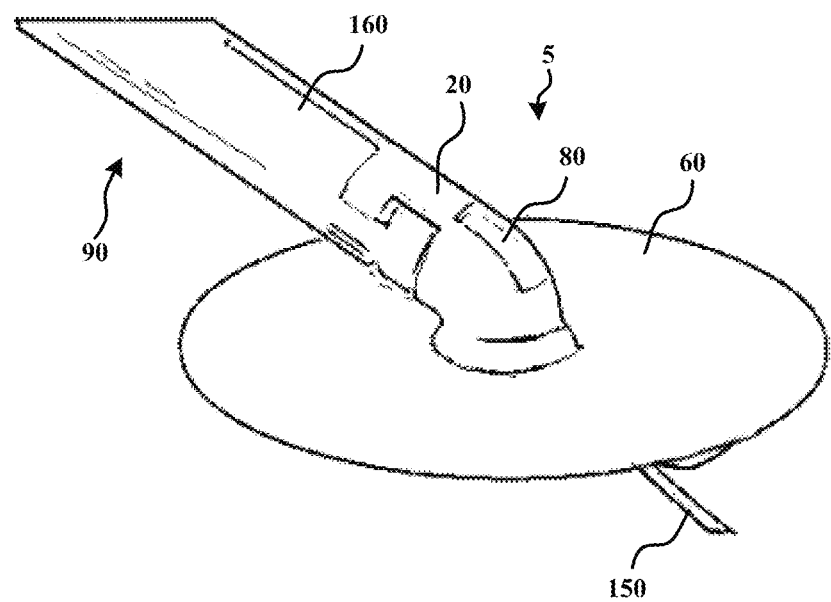
FIG. 33B shows a perspective view of the components shown in FIG. 33A in an assembled state with a wing and guidewire.
Figure 33C:
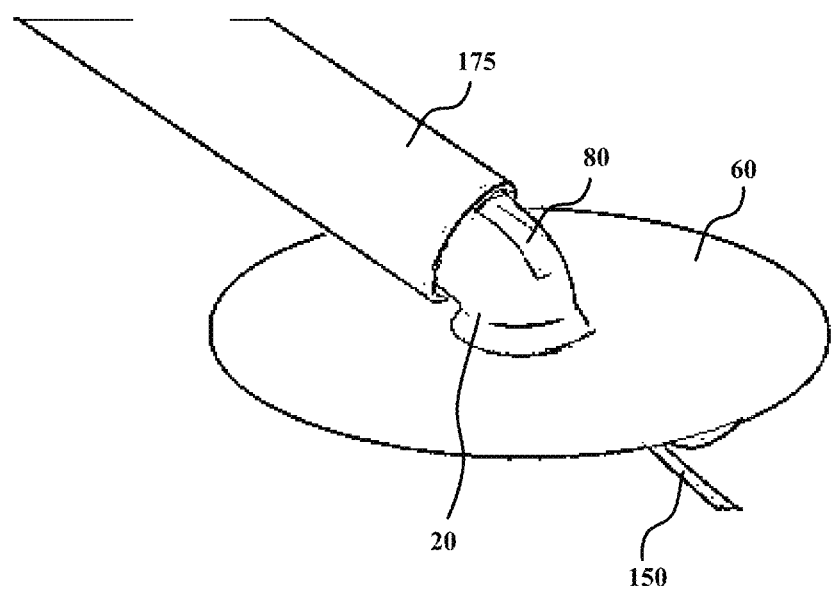
FIG. 33C shows the assembly of FIG. 33B together with a release sleeve.

The shaft 92 includes three flexible concentric slidable tubes 155, 160, 175. The inner tube (pusher-tube 155, illustrated in FIG. 7A) is configured to push the extra-luminal pin 80 from its proximal delivery position, as shown, e.g. in FIG. 2A, to its distal post deployment position, as shown, e.g. in FIG. 2B. The pusher-tube 155 has an internal diameter sized to accept the guidewire 150. The middle tube (retaining-sleeve 160) and outer tube (release-sleeve 175) in combination retain and release the implant which is attached to the distal end of the delivery system as shown in FIGS. 33A to 33C.

Figure 35:
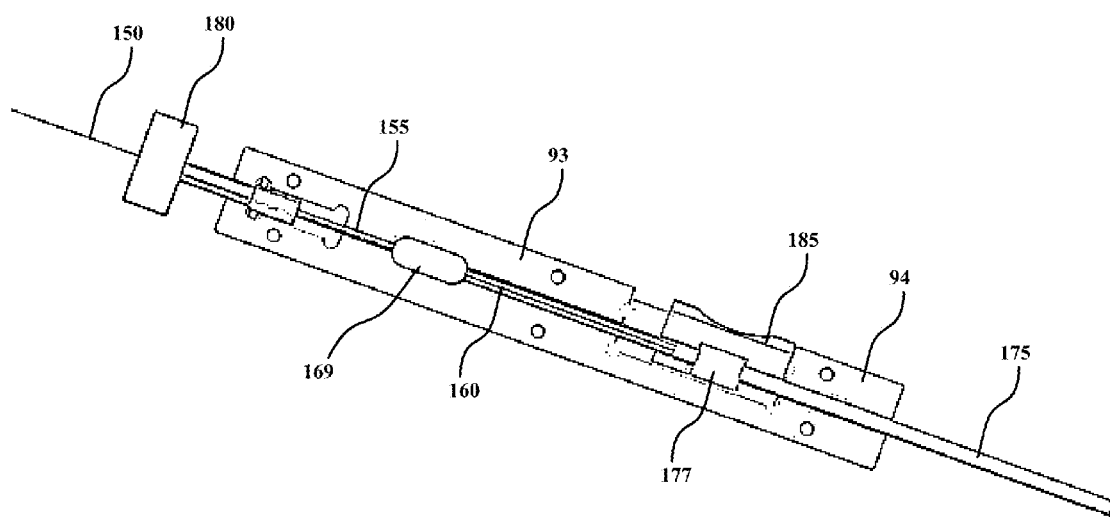
FIG. 35 shows a side view of interior components of the handle of the delivery system of FIG. 31A.

Referring to FIG. 35, the handle 93 is attached to the proximal end of the shaft 93 and is used to control the relative position of the implant 5, push the extra-luminal pin 80 and release the implant 5. As shown in FIG. 35, the handle 93 has its right-hand-side external cover removed from the mated left-hand-side cover 94 to expose the internal components of the handle 93.

Handle components: With reference to FIG. 35, the thumb button 180 activates the push-tube 155 to push forward the extra-luminal pin 80. The retaining-sleeve anchor 169 anchors the retaining-sleeve 160 to the handle 93 in a fixed position. The release-sleeve hub 177 connects the release sleeve 175 to a slide switch 185, which when slid proximally or backwards or backwards pulls the release sleeve 177 backwards or proximally relative to the retaining sleeve 160 to release the implant 5.

Figure 52:
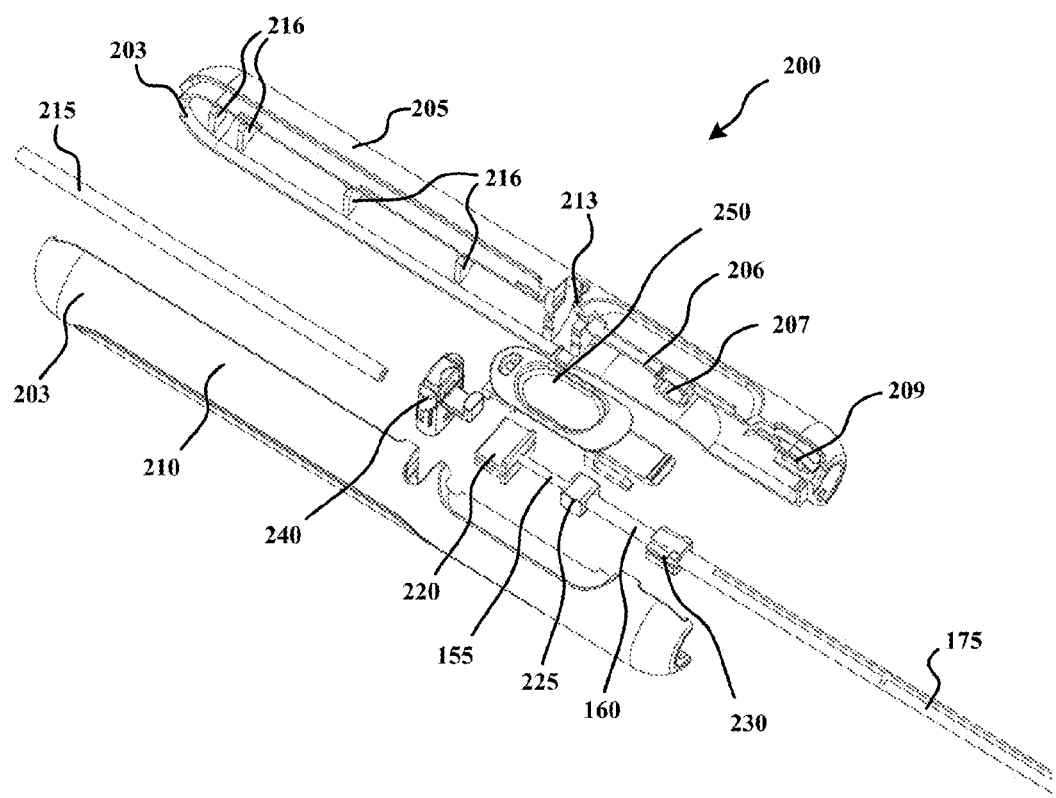
FIG. 52 shows an exploded view of a handle portion of a delivery system for implanting a closure device.

FIG. 52 shows another handle 200 configured to be mated to the shaft 92 in manner analogous to the handle 93. The handle 200 includes: a first housing portion 205, a second housing portion 210, a guidewire extension tube 215, a pusher tube hub 220, a retaining sleeve hub 225, a release sleeve hub 230, a lock member 240, and a thumb slider 250.

Figure 54A:
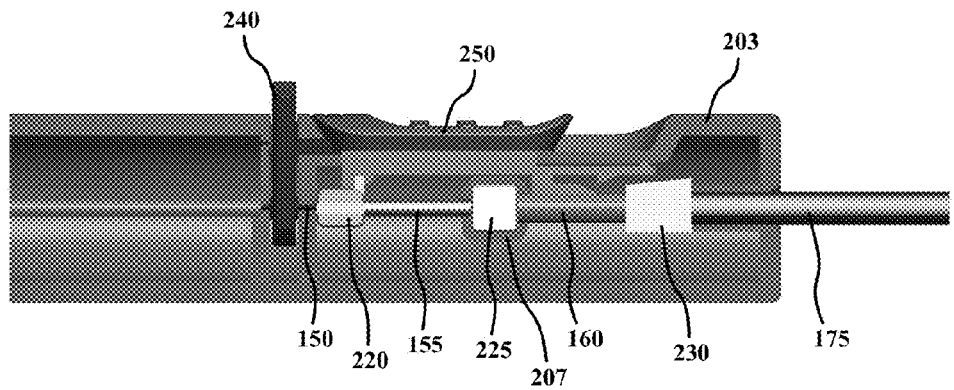
FIG. 54A shows a cross-sectional view of the handle portion of the delivery system of FIG. 52 in an initial state with a guidewire in place.
Figure 54B:
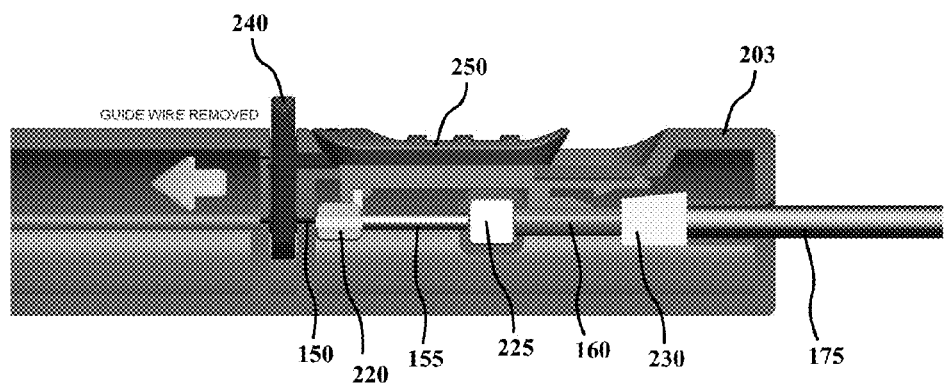
FIG. 54B shows a cross-sectional view of the handle portion of the delivery system of FIG. 52 with the guidewire being removed.
Figure 54C:
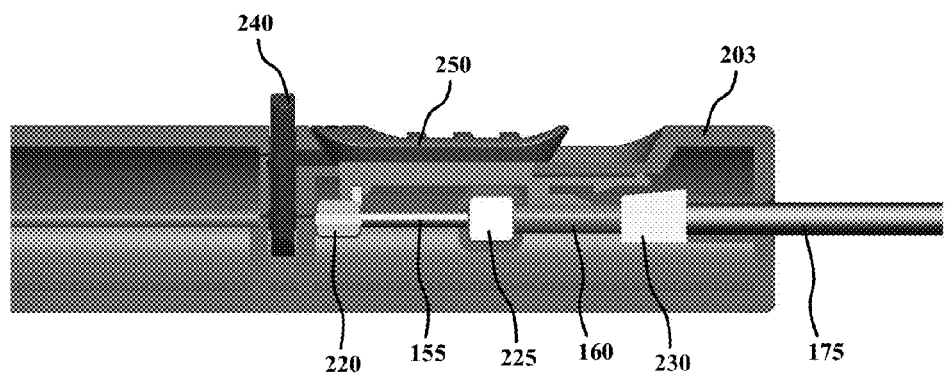
FIG. 54C shows a cross-sectional view of the handle portion of the delivery system of FIG. 52 after removal of the guidewire.
Figure 54D:
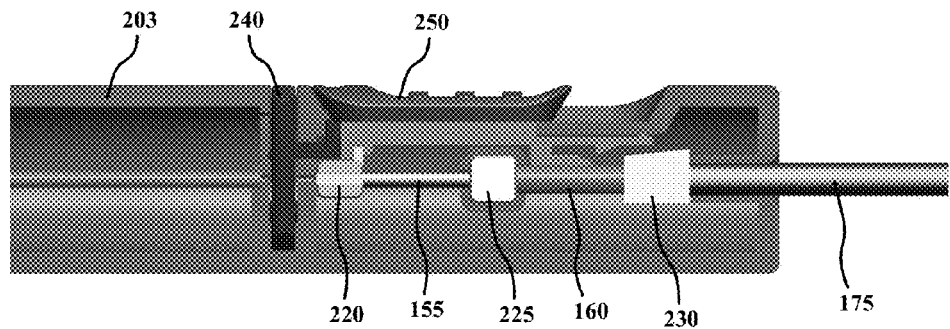
FIG. 54D shows a cross-sectional view of the handle portion of the delivery system of FIG. 52 after removal of the guidewire and depression of a lock member.

The thumb slider 250 is configured to move along a linear guideway formed by housing 203, which includes the first and second housing portions 205 and 210. In particular, the thumb slider 250 is configured to move, due to, e.g. manual actuation by the thumb of a human operator, between a first position and a second position. The first position is shown, for example, in FIGS. 54A to 54F, and the second position is shown, for example, in FIGS. 55A to 55C.

The guidewire 150 runs through the pusher tube 155 and through the handle, including through the guidewire extension tube 215 and out the proximal or rear end of the handle 200. The guidewire extension tube 215 is supported by support ribs 216 of the housing 203.

The handle 200 is configured such that movement of the thumb slider 250 from the first position to the second position causes the extra-luminal pin 80 of the implant 5 to move from its proximal delivery position as shown, e.g. in FIG. 2A to its distal post deployment position as shown, e.g. in FIG. 2B.

The lock member 240 is configured to prevent the deployment of the extra-luminal pin 80 prior to removal of the guidewire 150 from the delivery device. The lock member 240 is configured to be pressed transversely into the housing 203 from a first position illustrated, for example, in FIG. 54B, to a depressed second position illustrated, for example, in FIG. 54D when the user wishes to unlock the thumb slider 250.

Figure 53:
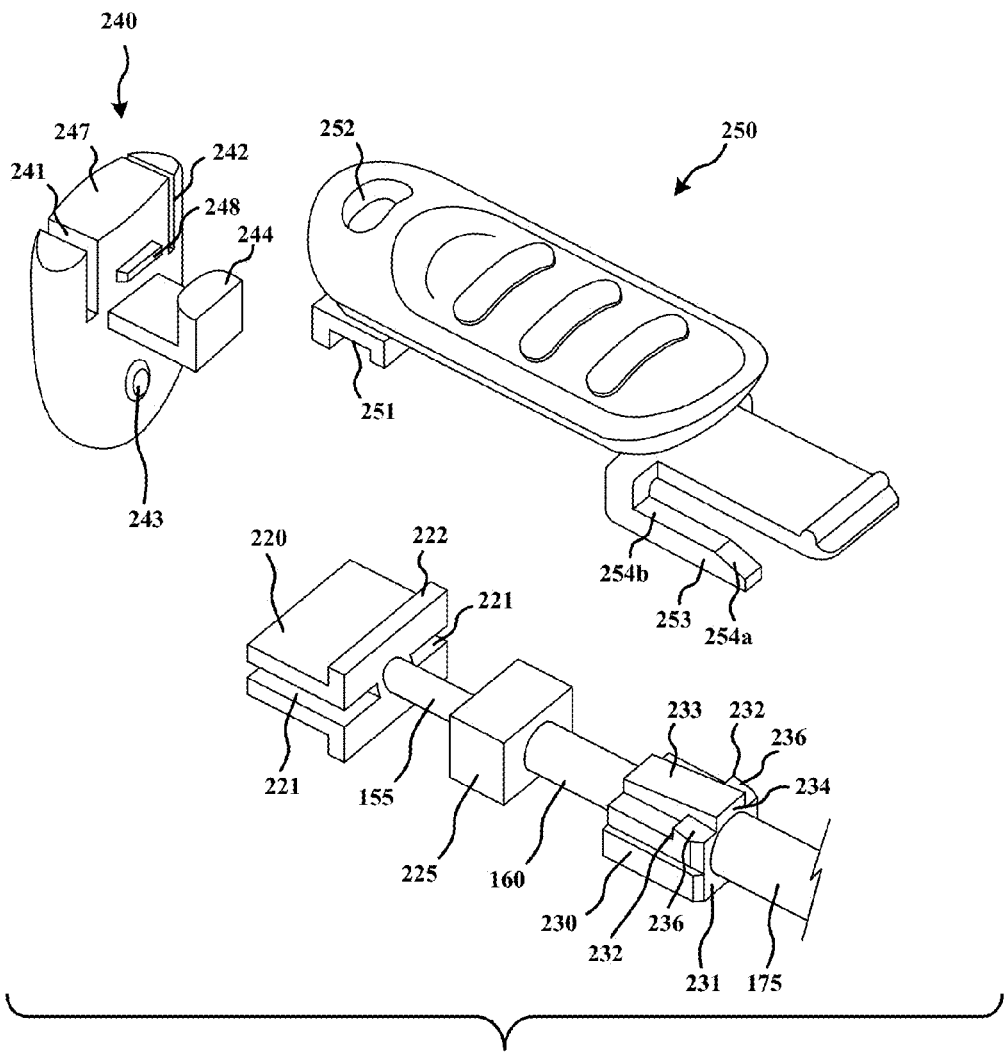
FIG. 53 shows components of the handle portion of the delivery system of FIG. 52.

Referring to FIG. 53, the lock member 240 includes a projection 248 that is received in a corresponding recess 213, illustrated in FIG. 52, of the housing 203. When the projection 248 is received in the recess 213, the lock member 240 is prevented from being depressed. In order to depress the lock member 240, the projection 248 must be moved out of engagement with the recess 213. This mechanism prevents, or at least reduces the likelihood of, inadvertent depression of the lock member 240 prior to insertion of the guidewire—for example, when the device is removed from its packaging, which is described in additional detail below.

In order for the operator to move the projection 248 out of engagement with the recess 213, the user applies a proximally directed force to the lock member 240. The lock member 240 includes a pair of slots 241 and 242 that allow a portion 247 between the slots 241 to bend or flex with respect to the remainder of the lock member 240 when the operator applies the proximally directed force. Since the projection 248 is disposed on the portion 247, this bending of the portion 247 causes the projection 248 to move out of engagement with the recess 213, thereby allowing the lock member 240 to be depressed.

When the lock member 240 is in the non-depressed first position, a locking tab 244 extends into a space in the thumb slider 250 adjacent a locking surface 252, such that the interface between the locking tab 244 of the lock member 240 and the locking surface of the thumb slider 250 forms a positive stop to prevent the thumb slider 250 from moving axially away from the lock member 240. Since the lock member 250 is constrained to the housing 203 in a fixed axial position, the positive stop between the lock member 240 and the thumb slider 250 prevents the thumb slider 250 from being slid forward to its distal position, thus preventing the corresponding actuation of the extra-luminal pin 80 into its deployed position.

Figure 54E:
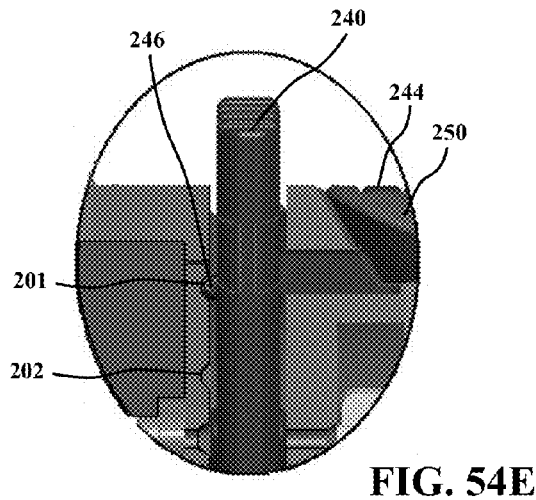
FIG. 54E shows an enlarged partial cross-sectional view of a lock member of the handle portion of the delivery system of FIG. 52 with the lock portion in a locked position.

In order to unlock the thumb slider 250 to allow deployment of the extra-luminal pin 80, the user depresses the lock member 240 to move the lock member from its first position to its depressed second position, illustrated, for example, in FIG. 54E. In the depressed position, the locking tab 244 moves out of engagement with the thumb slider 250, such that the locking surface 252 of the thumb slider 250 does not contact the locking tab 244 of the lock member 240 as the thumb slider 250 is pressed and moved forward or distally to thereby deploy the extra-luminal pin 80.

To prevent the lock member 240 from being depressed prior to removal of the guidewire 150, the lock member 240 is provided with a through hole 243 through which the guidewire 150 passes during positioning of the implant 5. When the guidewire 150 extends through the through hole 243, as illustrated in FIGS. 54A and 54B, the lock member 240 is prevented from being depressed, since the guidewire 150 engages the through hole 243 to block the lock member 240 from moving laterally with respect to the guidewire and into the depressed position.

Although the lock member 240 is provided with a through hole in the illustrated example, it should be understood that any suitable geometry, e.g. a slot, notch, and/or flat surface, may be provided to engage the guidewire 150 and thereby block movement of the lock member 240.

FIG. 54B shows the guidewire 150 being removed from the device in the direction of the arrow superimposed on the housing 203, until the guidewire 150 is fully withdrawn as illustrated in FIG. 54C. After the guidewire 150 is withdrawn, the guidewire 150 no longer extends through the through hole 243, as illustrated, e.g. in FIG. 54C. Thus, the lock member 240 is no longer prevented from being depressed.

Referring to FIG. 54E, the lock member 240 includes a projection 246 that engages a first recess 201 when the lock member 240 is in the first position and that engages a second recess 202 when the lock member 240 is in the depressed second position. This engagement allows the lock member 240 to be retained in the respective first and second positions, but allows movement upon application of a force sufficient to overcome the engagement. Thus, the projection 246 and the recesses 201 and 202 function as detent mechanisms.

Figure 54F:
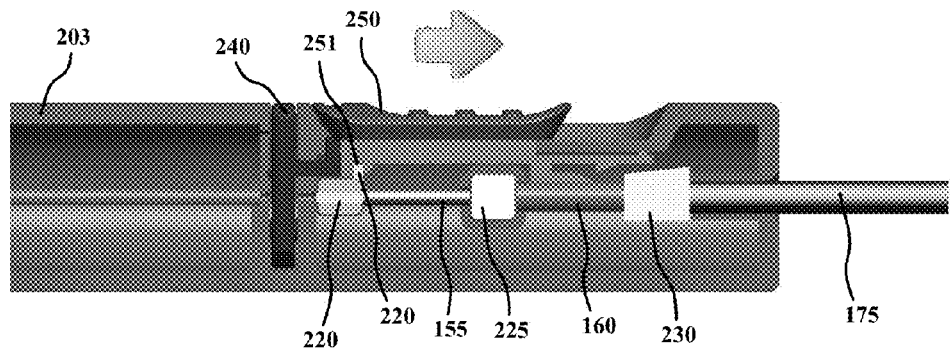
FIG. 54F shows a cross-sectional view of the handle portion of the delivery system of FIG. 52 at the onset of distal actuation of a thumb slider.
Figure 55A:
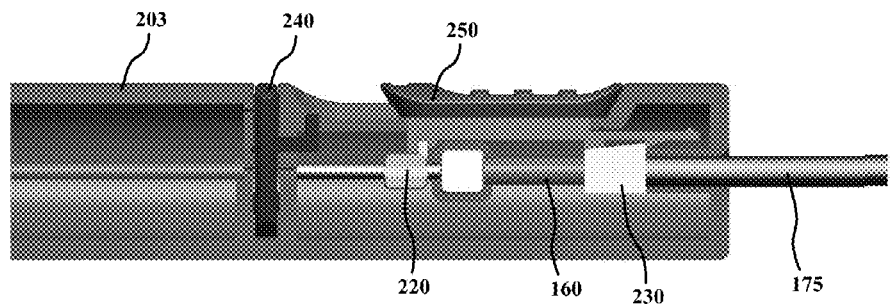
Figure 55B:
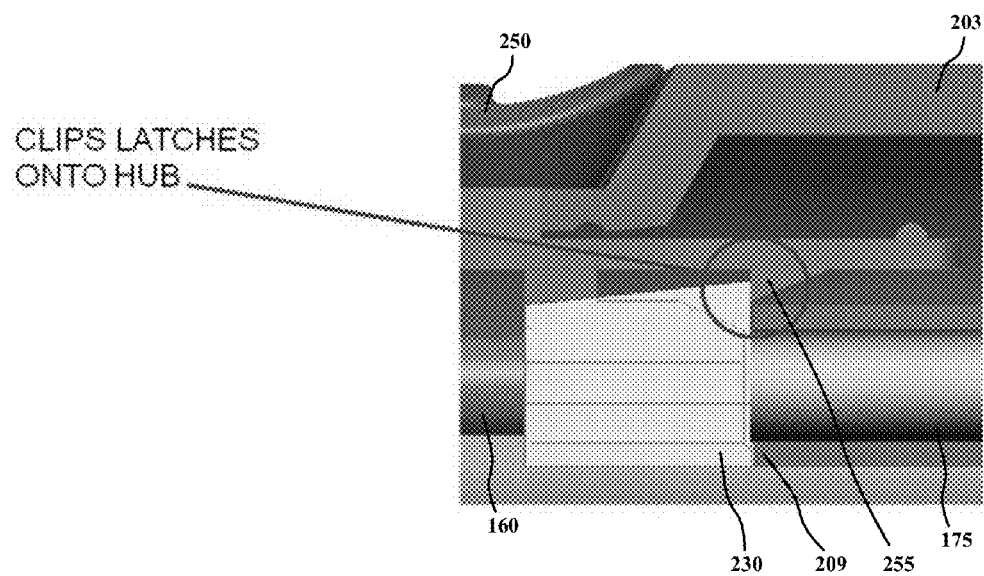

After the lock member 240 is depressed to disengage the lock member 244 from the thumb slider 250, as illustrated, e.g. in FIG. 54D, the user may slide the thumb slider 250 distally, in the direction illustrated by the arrow in FIG. 54F, until the slider reaches its distal second position, as illustrated, for example, in FIG. 55A.

This distal movement of the thumb slider 250 results in deployment of the extra-luminal pin 80. As with the handle 93, the handle 200 achieves the actuation of the extra-luminal pin 80 from its delivery position to its deployed position by distally pushing the pusher tube 155. In particular, the proximal end of the pusher tube 155 is attached to the pusher tube hub 220, which is in turn coupled to the thumb slider 250. Thus, as the thumb slider 250 moves distally or forward, the pusher tube hub 220 is also moved distally or forward, thereby also moving the pusher tube 155 forward to push the extra-luminal pin 80 from its proximal position to its extended deployed position.

Referring to FIGS. 52 and 53, the pusher tube hub 220 includes grooves 221 that receive respective corresponding linear guide ribs or projections 206 in the housing 203 to function as a linear slide. One of the guide ribs 206 is illustrated as part of the first housing portion 205, the second housing portion 210 being essentially identical, but mirrored, with respect to the first housing portion 205. The pusher tube hub 220 also includes a projection 222 that is received in a corresponding recess or groove 251 of the thumb slider 250 to constrain the projection 222 and thereby transfer proximal and distal motion of the thumb slider 250 to the pusher tube hub 220.

As the thumb slider 250 and the pusher tube are pushed distally relative to the housing 203, the retaining sleeve 160 and the release sleeve 175 remain stationary with relative to the housing. Thus, the pusher tube 155 is pushed relative to the retaining sleeve 160 and the release sleeve 175, and therefore also relative to the implant 5 supported by the retaining sleeve 160 and the release sleeve 175.

The retaining sleeve 160 is maintained in its stationary position relative to the housing 203 by being mounted in a retainer hub compartment 207 of the housing 203, as illustrated, for example, in FIGS. 52 and 54A. In the illustrated example, the retaining sleeve is maintained in a stationary position relative to the housing 203 during all stages of operation of the surgical system. It should be understood however, that the retaining sleeve may be configured to move relative to the housing during one or more stages of operation of the system.

The release sleeve 175 is maintained in its stationary position relative to the housing 203 during the forward movement of the thumb slider 250 by distal and proximal stops of the housing 203 that engage the release sleeve hub 230 to constrain distal and proximal movement, respectively. The distal stop is formed by a projection or wall 209 of the housing 203, as illustrated, e.g. in FIG. 55B, while the proximal stop is formed by a hub lock 208 of the housing 203, as illustrated, e.g. in FIGS. 56A and 56B.

Referring to FIG. 53, a front face 231 of the release sleeve hub 230 contacts the distal stop and projections 232 contact the proximal stop. In the illustrated example, two projections 232 engage a pair of respective hub locks 208; however, it should be understood than any number of projections 232, including a single projection 232 may be provided to engage any number of hub locks 208, including a single hub lock 208.

After deployment of the intra-luminal pin 80, the next procedural step is to release the implant 5 from the delivery device. In order to do so in the illustrated example, the user needs to move the release sleeve 175 proximally relative to the retaining sleeve 160. The mechanism for releasing the implant 5 upon the relative motion between the release sleeve 175 and the retaining sleeve 160 is described in further detail elsewhere in the present description.

In order to move the release sleeve 175 proximally relative to the retaining sleeve 160, which remains stationary relative to the housing 203, (a) the proximal lock, which is the hub lock 208 in the illustrated example, must be disengaged from the release sleeve hub and (b) the thumb slider 250 engages the release sleeve hub 230 such that proximal movement of thumb slider 250 relative to the housing 203 causes corresponding movement of the release sleeve hub 230, and therefore also the release sleeve 175, relative to the housing 203 and the retaining sleeve 160.

Figure 56A:
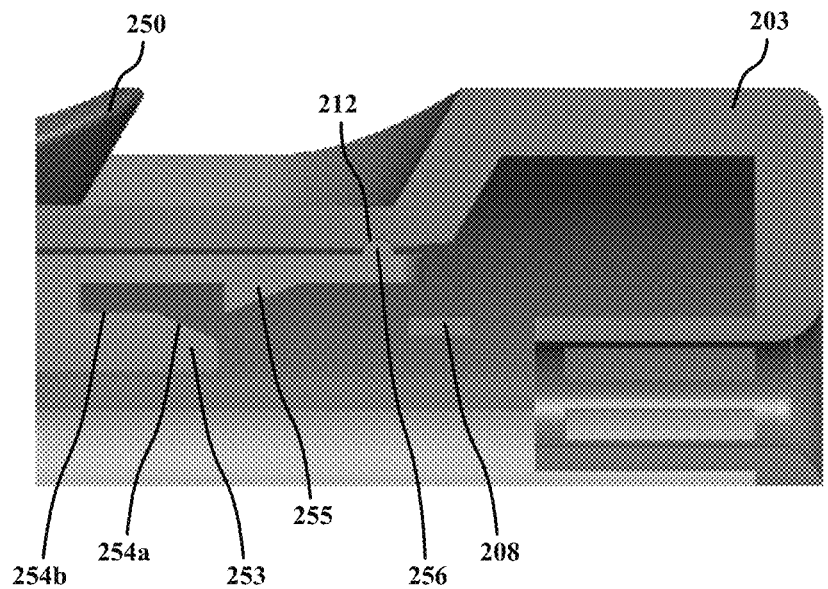
Figure 56B:
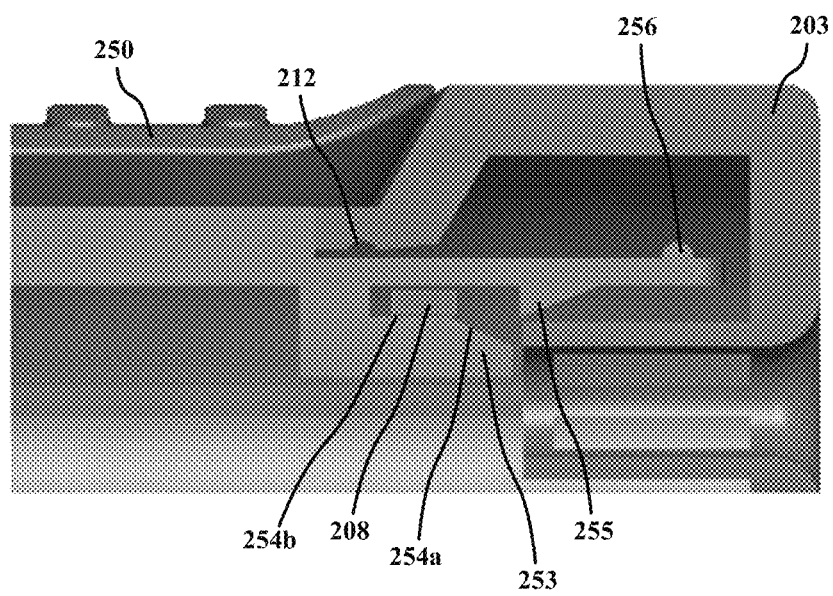

Referring to FIGS. 53, 56A, and 56B, the thumb slider 250 includes a pair of cam sliders 253 that engage the respective hub locks 208 as the thumb slider 250 approaches its distal second position. In particular, the distal advancement of the ramped or sloped surfaces 254a of the cam sliders 253 causes the hub locks 208 to move laterally and clear of the projections 232 of the release sleeve hub 230. Continued distal advancement of the thumb slider 250 causes the hub locks 208 to slide along flat surfaces 254b of the respective cam sliders 253 to maintain the hub locks 208 in their disengaged positions.

The hub locks 208 may be configured as cantilevered projections from the housing 203 that flex in the lateral direction in the manner of a leaf spring, while maintaining sufficient rigidity in the axial direction to resist proximal movement of the release sleeve hub 230 when engaged therewith. Moreover, any other suitable proximal locking mechanism may be provided.

After the hub locks 208 are moved out of alignment with the projections 232 of the release sleeve hub 230, a clip member 255, which slides over a ramped or sloped surface 233 of the release sleeve hub 230, latches with the release sleeve hub 230 by engaging with distally facing latch surface 234 of the release sleeve hub 230.

Figure 57A:
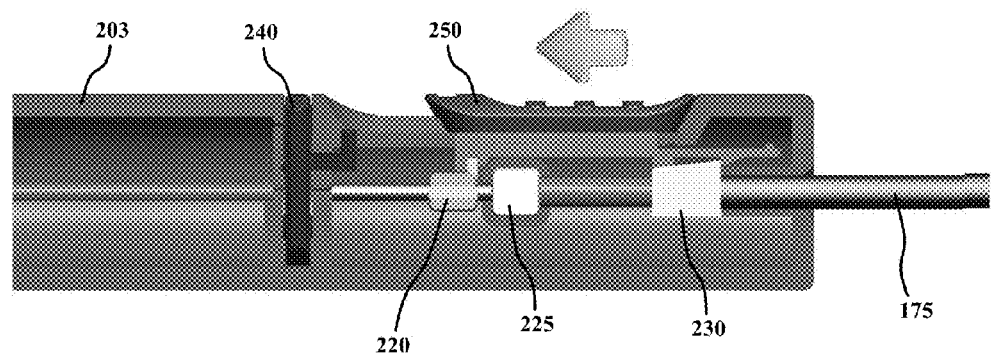
Figure 57B:
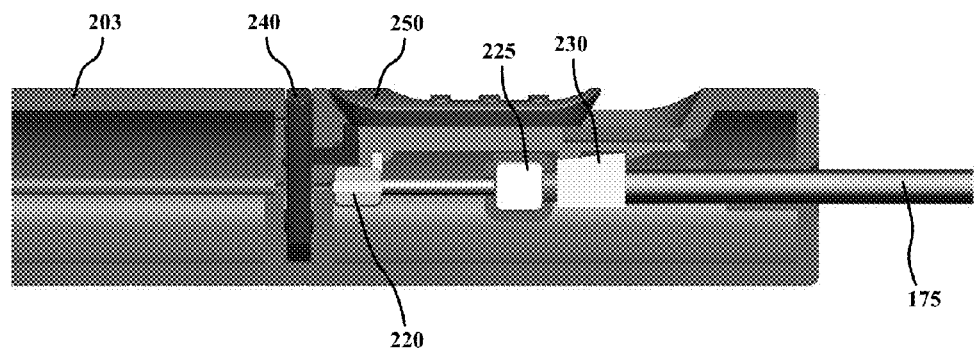

After latching of the thumb slider 250 to the release sleeve hub 230, the operator moves the thumb slider 250 proximally to a proximal third position in the direction of the arrow shown in FIG. 57A, to retract the release sleeve hub 230 and the release sleeve 175 to the position shown in FIG. 57B. Although in the illustrated example, the proximal third position of the thumb slider corresponds to the proximal first position of the thumb slider, it should be understood that the first and third positions may be different.

The cam surfaces 254a and 254b are of sufficient length in the illustrated example to maintain the disengaged position of the hub locks 208 until the proximally directed faces of the projections 232 of the release sleeve hub 230 have proximally cleared the distally facing stop surfaces of the hub locks 208.

When the device is in the state illustrated in FIG. 57B, the implant 5 is released from the end of the delivery device via the proximal movement of the release sleeve 175 relative to the retaining sleeve 60.

The thumb slider 250 further includes a projection 256 that engages a corresponding recess 212 in the housing 203 when the thumb slider 250 is in the proximal position. This engagement allows the lock member 240 to be retained in the respective first and second positions, but allows movement upon application of a force sufficient to overcome the engagement. Thus, the projection 256 and the recess 212 function as a detent mechanism.

Figure 57C:
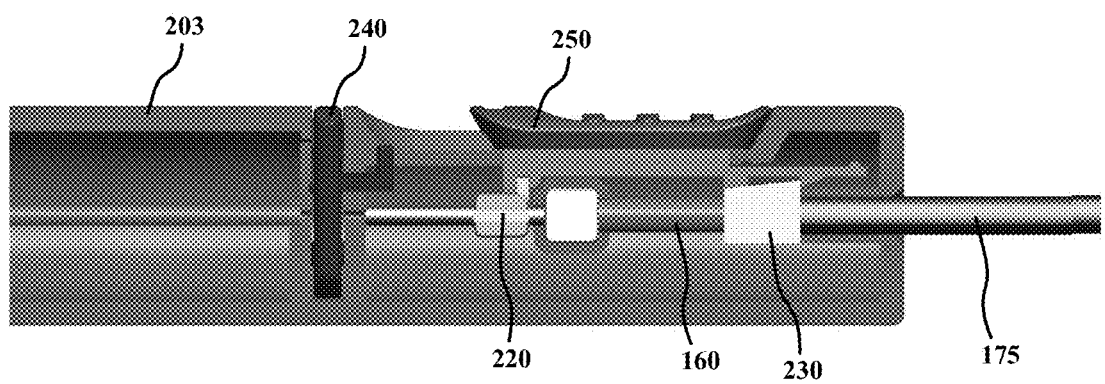

Prior to withdrawal of the distal end of the delivery device, the thumb slider 250 may be again moved distally, to a fourth position, as illustrated in FIG. 57C. Moving the thumb slider 250 to the distal fourth position causes the release sleeve 175 to move distally with respect to the retaining sleeve 160, which causes the distal end of the release sleeve 175 to at least partially cover the interlocking projections 165 of the retaining sleeve 160, which are illustrated, for example, in FIG. 33A. Re-covering or resheating these projections 165 may be advantageous to reduce the risk of trauma to the surrounding tissue as the delivery device is withdrawn from the percutaneous tissue tract.

Although in the illustrated example, the distal fourth position of the thumb slider corresponds to the distal second position of the thumb slider, it should be understood that the first and third positions may be different.

To facilitate passage of the release sleeve hub 230 distally past the hub locks 208, the release sleeve hub 230 may be provided with ramped or sloped chamfer surfaces 236, which are illustrated in FIG. 53. These surfaces 236, which slope downwardly as they extend distally along the release sleeve hub 230, engage the hub locks 208 as the release sleeve hub 230 is moved distally in order to move raise the hub locks 208 to prevent the hub locks 208 from axially blocking the projections 232 of the release sleeve hub 230.

The shaft 92 is designed to push the implant 5 down the procedural sheath 100 into the artery 2 and allow control of the implant's relative position by the user from the handle 93.

Implant retention and release: Referring, e.g. to FIGS. 33A to 33C, to secure the implant 5 on the distal tip of the delivery device 90, two profiled interlock projections 165 which extend from the retaining sleeve 160 engage into the implant's matching interlock recesses 45 in the neck 42 of the foot core 20. To ensure the profiled projections 165 remain engaged with the foot core 20, a release-sleeve 175 is positioned in a distal or forward location, as illustrated in FIG. 33C, to prevent the projections 165 from moving laterally outwardly.

Figure 34A:
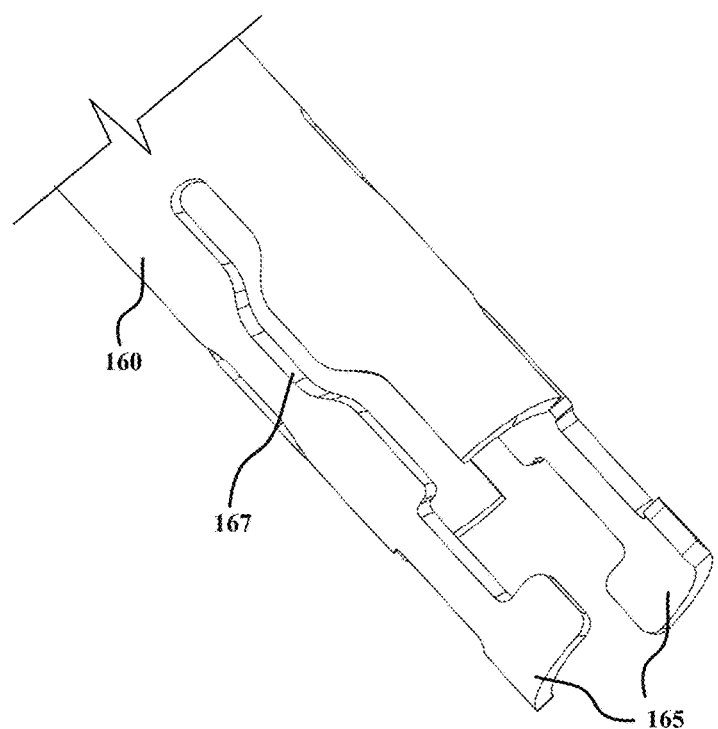
FIG. 34A shows a perspective view of the retaining sleeve of the system of FIG. 31A
Figure 34B:
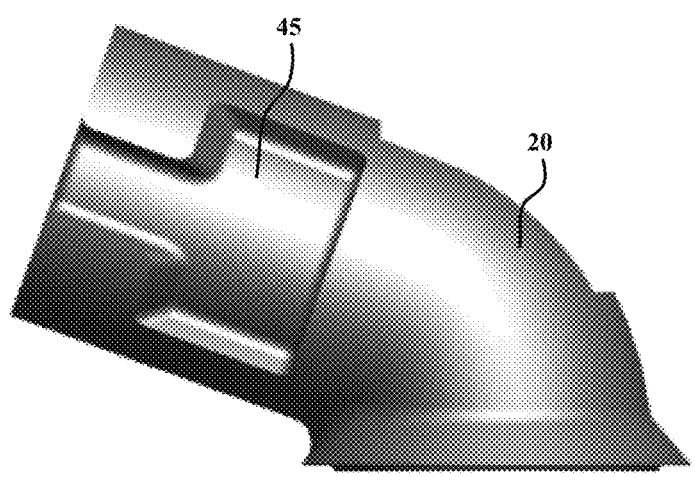
FIG. 34B shows a partial side view of the foot core of the closure device of FIG. 1A, corresponding to the extra-luminal section of the foot core.
Figure 34C:
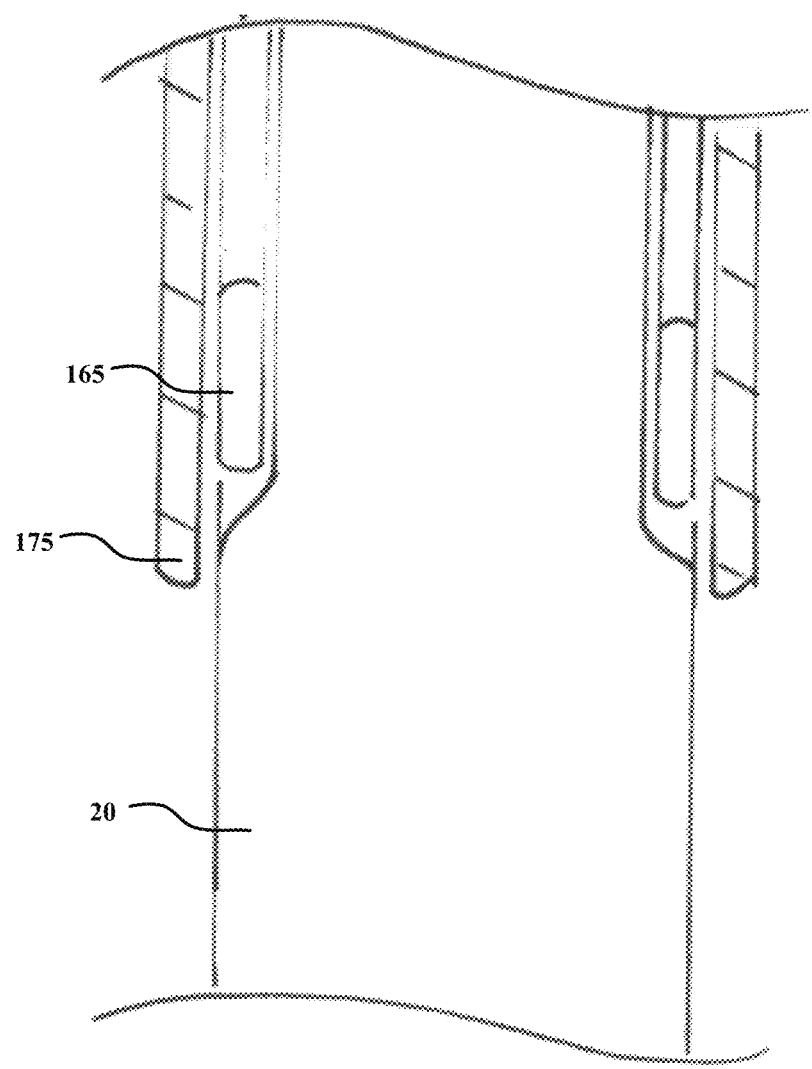
FIG. 34C shows a cross-sectional side view of an interlocking connection between the retaining sleeve, foot core, and release sleeve of the system of FIG. 31A.

To release the implant 5 from the distal tip of the delivery device 90, the release-sleeve 175 is slid back to expose the interlock projections 165 on the retaining-sleeve 160. The tip of the retaining-sleeve 160 is split longitudinally, via longitudinal splits or notches 167, to allow lateral movement of the interlocking projections 165, and the rear shoulders of interlocking recesses 45 on the foot core 20 may be ramped, as illustrated, e.g. in FIGS. 34A to 34B, to facilitate release of the implant 5 by pulling the delivery device 90 away from the implant 5. It should be understood, however, that any suitable geometry may be provided, e.g. a perpendicular edge, under-cut, etc, to mate with appropriate geometries of the interlocking projections 165.

Further, mating surfaces of the interlock projections 165 and the interlocking recesses 45 may be provided with one or more radial protrusions that engage with one or more corresponding radial recesses. For example, an interlocking projection 165 may include a plurality of radial protrusions that engage a corresponding plurality of radial recesses of a mated interlocking recess 45, or the interlocking recess 45 could be provided with the radial protrusions that mate with corresponding radial recesses of the interlocking projection 165. Further, the interlocking recess 45 could have at least one recess and at least one protrusion, the at least one recess and the at least one protrusion respectively mating with corresponding at least one protrusion and at least one recess of the interlocking recess 45. These various surface recess/protrusion configurations may provide a high level of securement (e.g. in the axial direction) between the interlocking projections 165 and the interlocking recesses 45. Moreover, these various surface recess/protrusion configurations may be provided alone or in combination with other interlocking mechanisms between the interlocking projections 165 and the interlocking recesses 45.

Although the interlocking projections 165 extend straight along the length of the retaining sleeve 160, it should be appreciated that the projections 165 may be flared outwardly, such that retraction of the release sleeve 175 allows the interlock projections 165 to spring outwardly away from their interlocking engagement with the interlock recesses 45.

Figure 36:
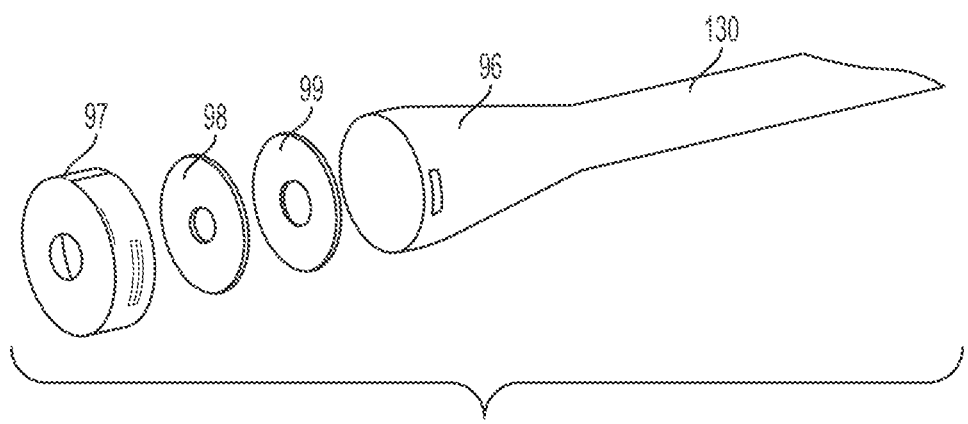
FIG. 36 shows a perspective view of a loading funnel.

Referring to FIG. 36, the loading funnel 95 is used to compress the flexible wing 60 of the implant into a cylindrical shape to allow it to fit within the procedural sheath 100 for delivery. The loading funnel 95 is also used to insert the compressed implant and delivery system into the procedural sheath 100 through the sheath's valve, as shown in FIG. 30. The loading funnel 95, in accordance with some exemplary embodiments, is used immediately prior to delivery to avoid storage of the flexible wing 60 in the compressed state and potentially taking a memory set shape in the compressed form.

The loading funnel in the illustrated example includes four components namely, the funnel or funnel body 96, cap 97, seal 98, and seal-retainer 99 shown in FIG. 36. It should be understood however that the loading funnel may have more or fewer components.

Figure 37:
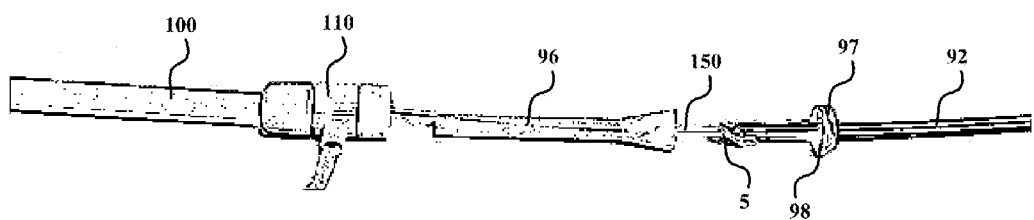
FIG. 37 shows the funnel of FIG. 36, the closure device of FIG. 1A, and a shaft of the delivery system of FIG. 31A.

The cap 97 and seal 98 are pre-loaded on the shaft 92 of the delivery device 90 proximal to the implant 5. The funnel 96 is advanced over the implant 5, large opening end first, to compress the wing 60 into a cylindrical shape as the tapered section of the funnel 96 is advanced over the implant 5. The funnel 96 is advanced until the implant 5 is resident in the cylindrical section 130 of the funnel 96. FIG. 37 shows the relative positions of the funnel body 96, cap 97, and seal 98 to the implant 5 and shaft 92 of the delivery device 90 during advancement of the funnel 96 relative to the implant 5.

Once the implant 5 is disposed in the cylindrical section 130 of the funnel 96, the cap 97 is now attached to the funnel 96, which forms a seal with the delivery device's shaft 92.

Figure 38:
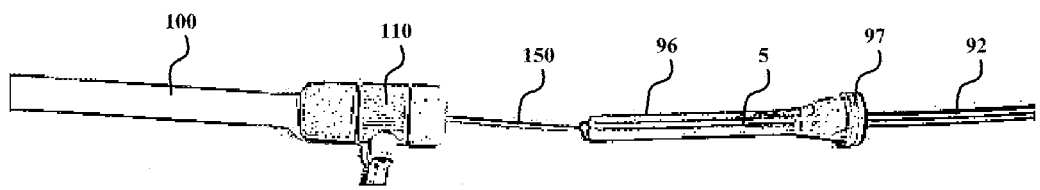
FIG. 38 shows the components shown in FIG. 37 with the closure device disposed within the funnel.

FIG. 38 shows the relative position of the implant 5 within the funnel 96 after being loaded therein.

Figure 39A:
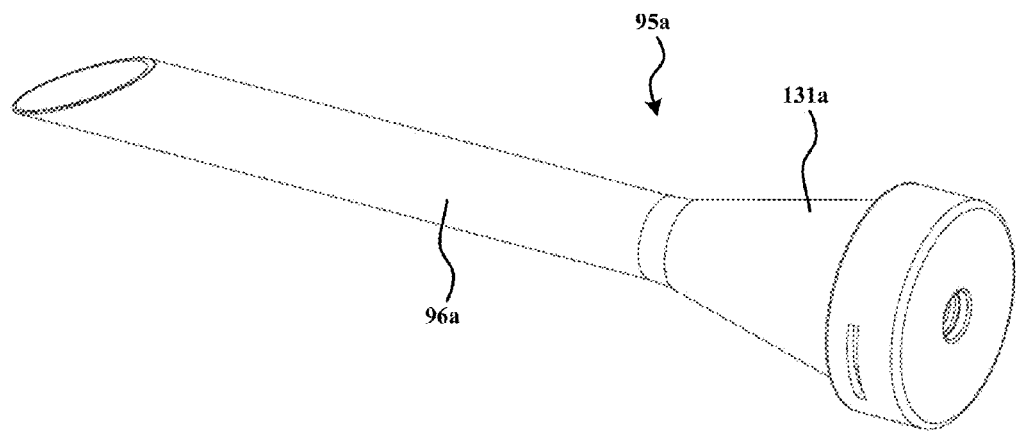
FIG. 39A shows a perspective view of another loading funnel.
Figure 39B:
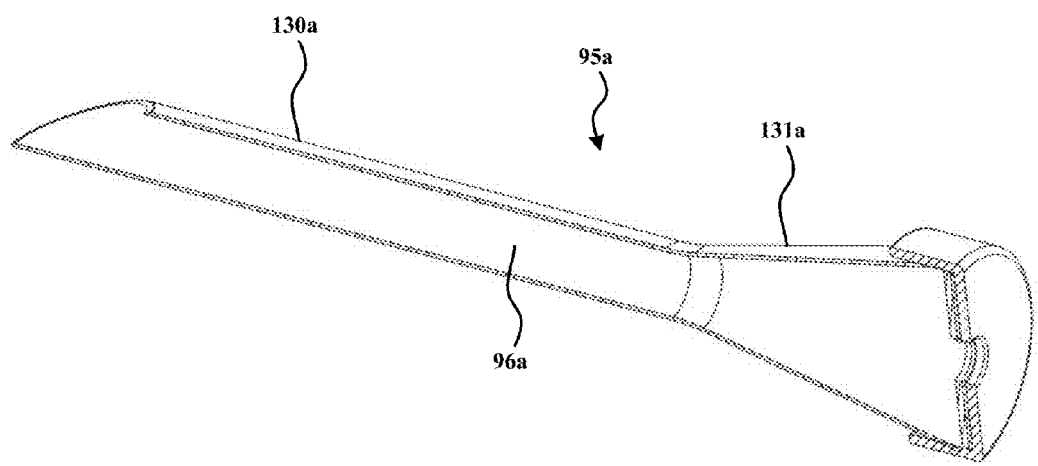
FIG. 39B shows a cross-sectional perspective view of the loading funnel of FIG. 39A.
Figure 39C:
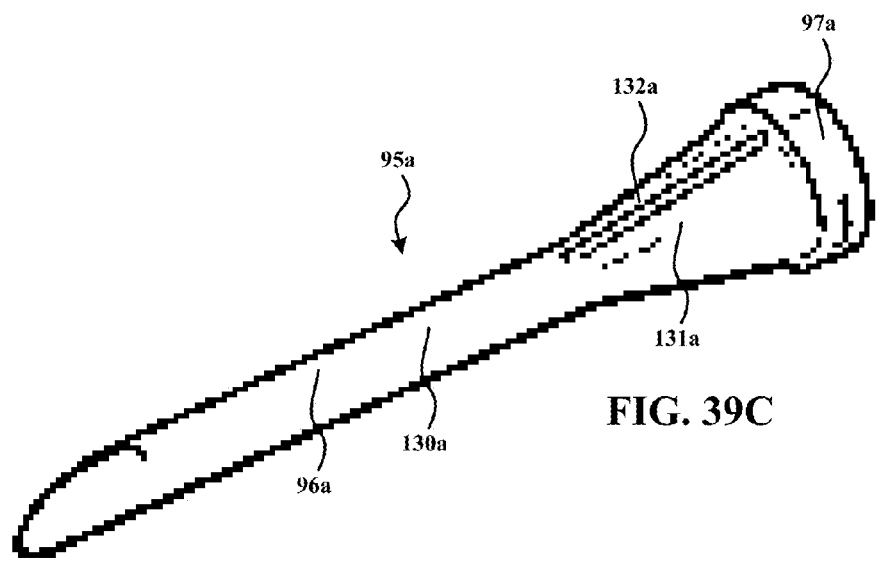
FIG. 39C shows a perspective view of the loading funnel of FIG. 39A.

Loading funnel configurations: The loading funnel 95 in a very simple form may be a tapered funnel. However, to encourage the flexible wing 60 to fold when loaded into the funnel body 96, an alternative option is to provide a funnel body 96a that includes a protrusion 132a along the tapered section 131a which extends into the cylindrical section 130a, as shown in FIGS. 39A to 39C. With this option, the loading funnel 95a is positioned relative to the flexible wing 60 to encourage one side of the wing 60 to be lifted above the opposite leaflet of the wing 60 during insertion.

Figure 40A:
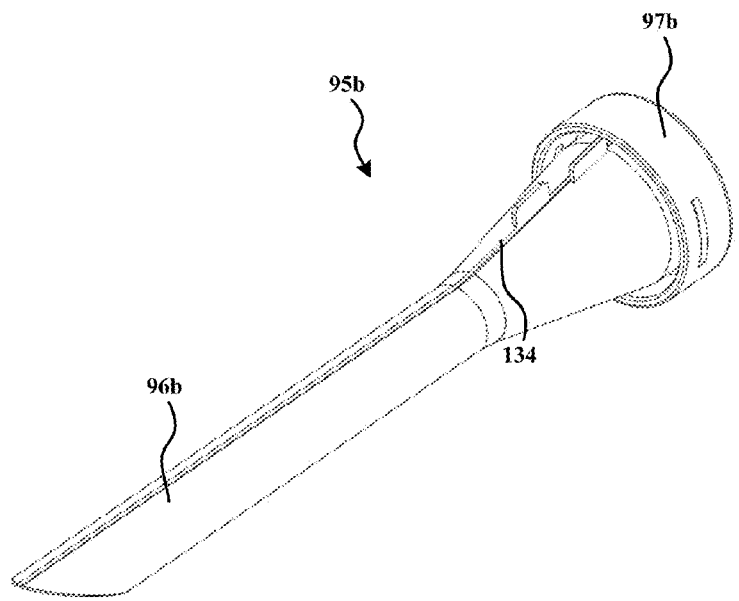
FIG. 40A shows a perspective view of another loading funnel.
Figure 40B:
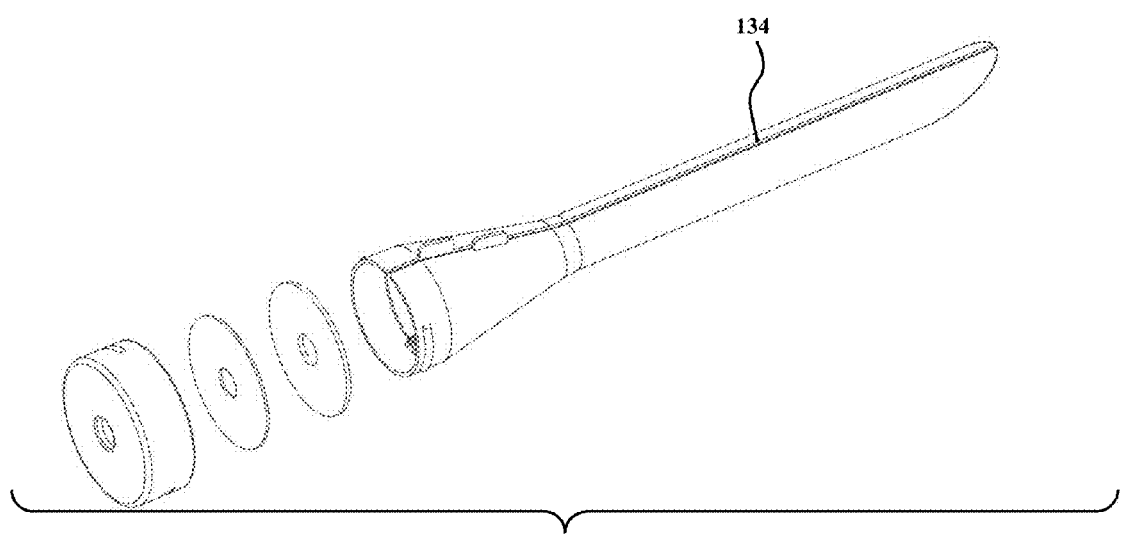
FIG. 40B shows an exploded view of the loading funnel of FIG. 40A.

Referring to FIGS. 40A and 40B, a third option is to have a splittable funnel 96b for removal from the shaft 92 of the delivery device 90 once the implant 5 is delivered through the procedural sheath hub 110 and valve. Once the implant 5 is within the procedural sheath 100, the funnel 95b may be withdrawn from the sheath valve, its cap 97b then removed, and the funnel body or section 96b may then be opened, via separation of two subparts connected at split line 134 to remove the funnel body 96b from the shaft 92 of the delivery device 90.

Figure 41A:
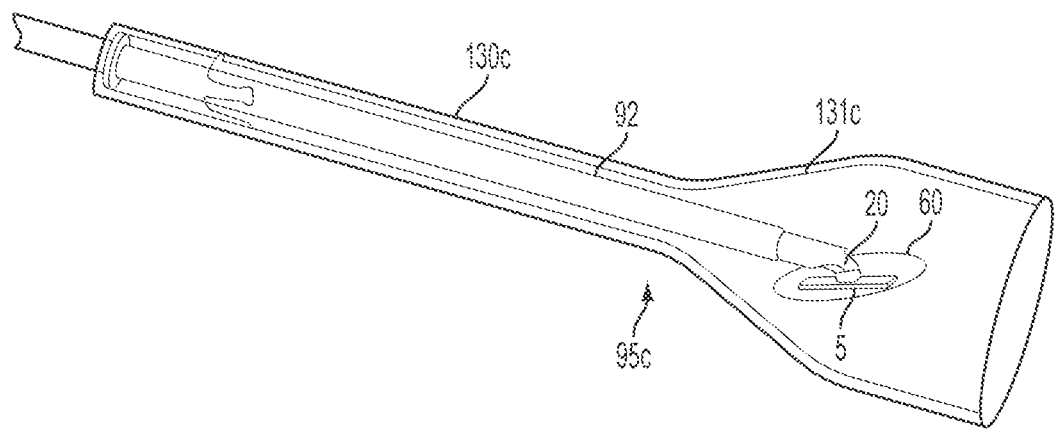
FIG. 41A shows a perspective view of another loading funnel.
Figure 41B:
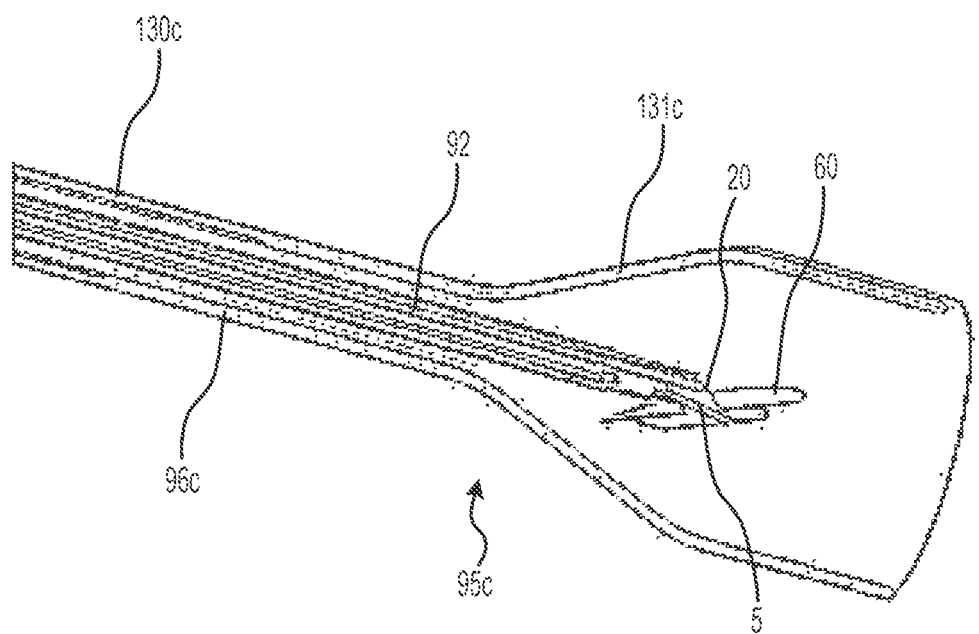
FIG. 41B shows a cross-sectional partial perspective view of the loading funnel of FIG. 41A.
Figure 42A:
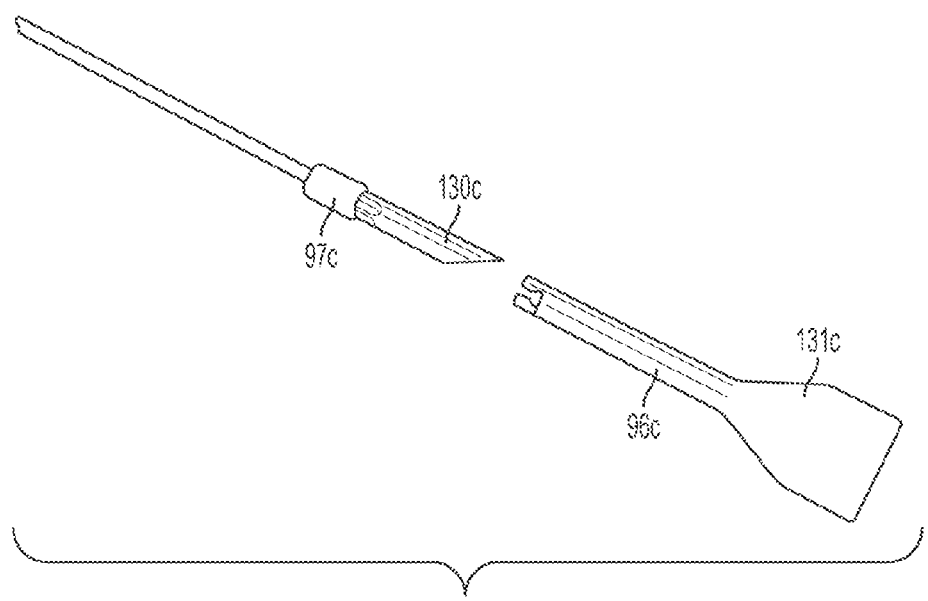
FIG. 42A shows an exploded perspective view of the loading funnel of FIG. 41A.

The above-described loading funnel concepts require the cap 97, 97a, 97b to be pre-loaded onto the shaft 92 of the device 1 proximal to the implant 5 and the funnel 96, 96a, 96b to be advance over the implant 5 and shaft 92. Referring to FIGS. 41A and 41B, a fourth concept is to have the funnel 95c pre-loaded onto the shaft 92, proximal to the implant 5, and advance the funnel 95c distally over the implant 5 to compress the flexible wing 60 into the cylindrical section 130c and into the cannula section 135c of the loading funnel 95c. The tapered section 131c and cylindrical section 130c of the funnel body 96c is completely removable from the cannula 135c, as illustrated in FIG. 42A. The loading cannula 130a is cylindrical in shape and is used to insert the implant 5 and device 90 through the procedural sheath valve and into the procedural sheath 100 for delivery into the artery 2. The delivery cannula 130, 130a and 135c may be chamfered at it distal end to assist in penetrating the valve at the rear of the procedural sheath 100. As illustrated in FIG. 42A the funnel body 96c has been removed after loading the implant 5 into loading cannula 135c.

Figure 42B:
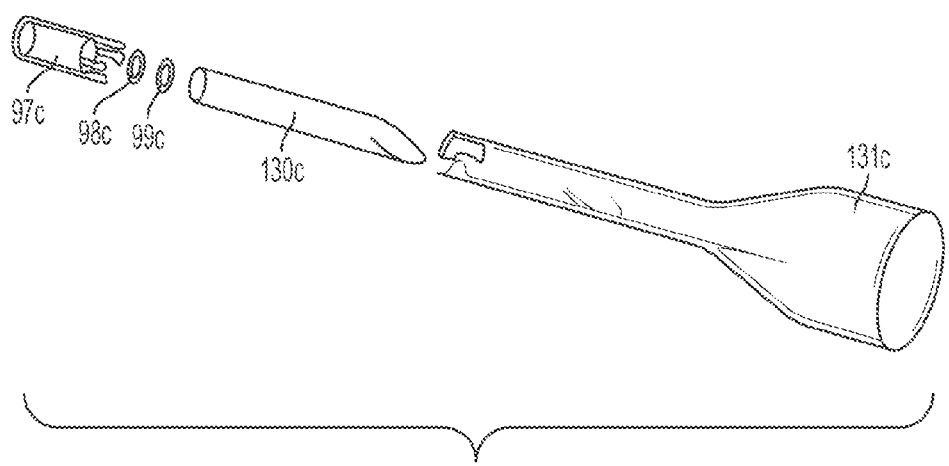
FIG. 42B shows a further exploded perspective view of the loading funnel of FIG. 41A.

FIG. 42B shows the components of the loading funnel 95c, including loading cannula 135c, detachable funnel 96c, end cap 97c, seal 98c, and seal retainer 99c. The loading cannula 135c and detachable funnel 96c form the funnel body 95c in this example. The proximal end of the delivery cannula 135c is adapted to form a seal around the shaft 92 of the device 90 but allow the shaft 92 to axially slide relative to the cannula 135c. This configuration of loading funnel 95c also has the advantage of protecting the implant 5 during storage and handling of the device 90.

FIGS. 43A to 43M show alternative funnel bodies 96d, 96e, 96f, 96g, and 96h. These funnel bodies 96d, 96e, 96f, 96g, and 96h may be used in connection with, for example, the preloaded loading funnel 95c shown in FIG. 41A, in place of funnel body 96c, or in place of any of the other funnel bodies recited herein.

Figure 43A:
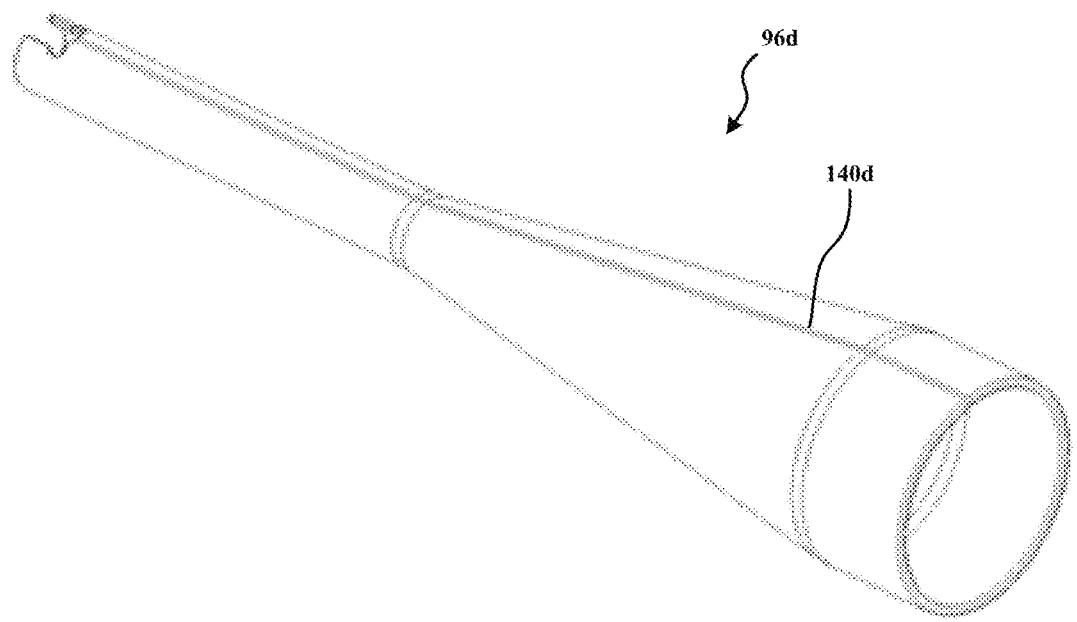
FIG. 43A shows a perspective view of a split funnel body.

Referring to FIG. 43A, the detachable funnel section or body 96d includes a longitudinal split 140d to facilitate removal of the funnel section from the guidewire 150. This split 140d may be a discontinuation of the component to provide a gap, or allow a gap to be formed (e.g. via flexing of the funnel body 96d) for the guidewire 150 to pass there through during removal. This split may also be formed by physical removal of a strip of material from the funnel wall, for example as a peelable strip.

Referring to FIGS. 43B to 43D, the funnel body 96e includes a weakened or notched section 145e that allows the funnel wall, in this example, to have a continuous integral internal surface which can easily be split along the weakened or notched section 145e. In the illustrated example, the weakened section is provided as a longitudinally extending groove or channel that weakens the structure of the funnel wall. The weakened or notched section 145e may be split, for example, by manual exertion of force by an operator.

The open split arrangement of FIG. 43A and the weakened wall arrangement of FIGS. 43B to 43D may, in some examples, be notched at the beginning of the splits or pre-split weakened portions to allow ease of locating the guidewire into the split, e.g. to facilitate relative movement of the guidewire from the inner lumen of the funnel body to the exterior of the funnel body via the split.

For example, referring to FIGS. 43E TO 43G, a split funnel body 96f, which includes features analogous to the split funnel body 140d of FIG. 43A, further includes a notch 142f, which is continuous with the split 140f.

It should be appreciated that a split or splittable funnel body concept is applicable to any funnel arrangement in the context of the present invention. Further, although the splits or split lines of the illustrated examples are coplanar with the longitudinal axes of the respective funnel bodies, it should be appreciated that the split or split line may be non-coplanar and/or have an irregular path.

Moreover, although the illustrated examples include a single split or split line, it should be appreciated that multiple splits or split lines or any combination of splits and split lines may be provided. Further, a respective split line may be split at one or more locations along the length of the split line and weakened so as to be splittable at one or more other locations along the split.

Other mechanisms for removing the funnel body may include, for example, cutting or tearing the funnel body, e.g. with a cutting tool, in the presence or absence of predetermined split lines such as the split lines described above.

Figure 43H:
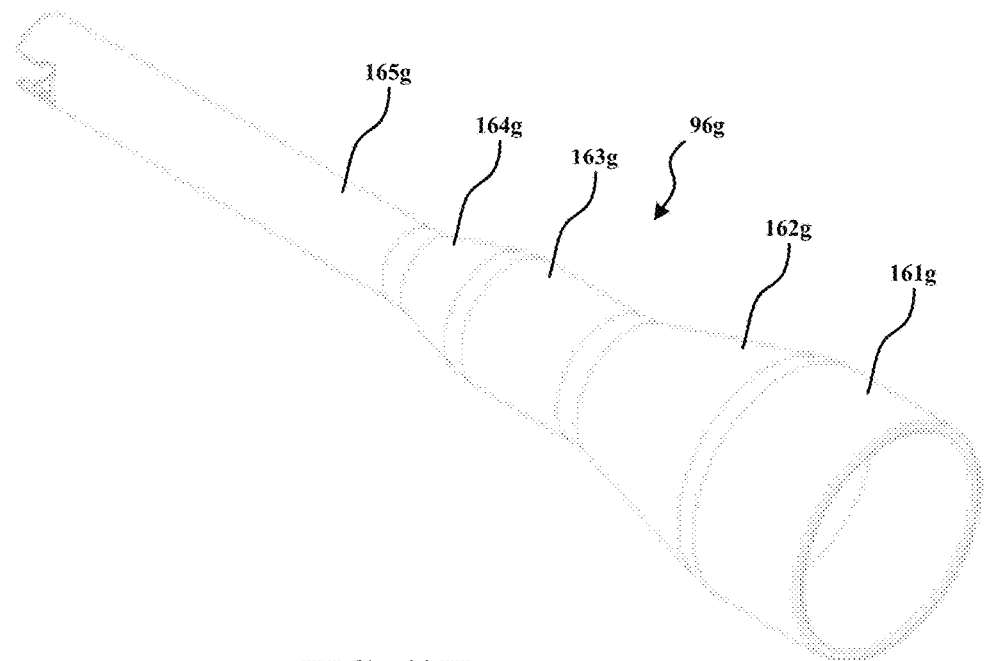
FIG. 43H shows a perspective view of a staged funnel body.
Figure 43I:
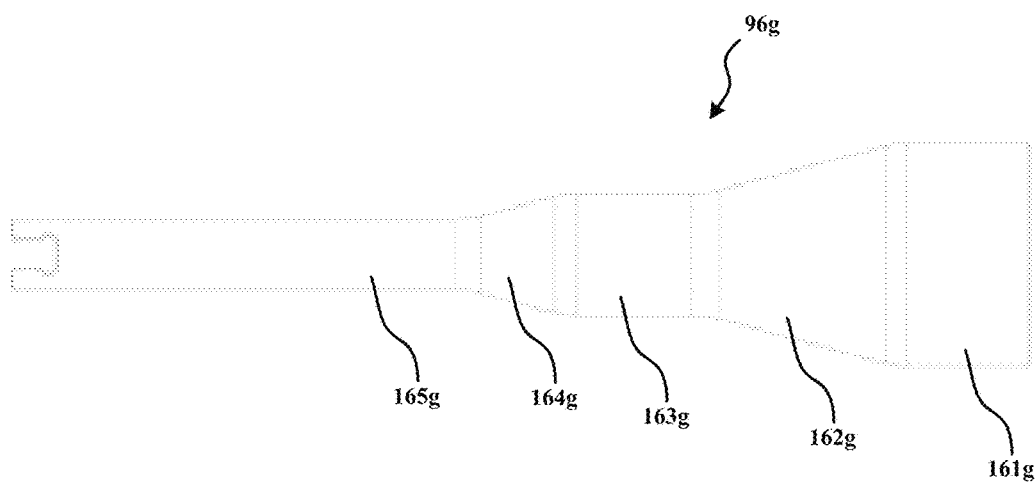
FIG. 43I shows a side view of the staged funnel body of FIG. 43H.

FIG. 43H shows a perspective view of a staged funnel body 96h that may be used in connection with, e.g. any of the funnel arrangements described herein. As shown, the staged funnel body 96h includes two distinct tapered or funnel-shaped portions 162g and 164g separated axially by a constant-diameter (in this example, cylindrical) portion 163g. Sections 161g and 130g are at opposed axial ends of the funnel body 96h and are, in this example, cylindrical. The staged funnel body 96 provides a progressive folding of the implant in two distinct sections.

FIGS. 43J to 43M show an offset funnel body 96h, which may be used in connection with, e.g. any of the loading funnel arrangements described herein. In this arrangement, the overall central axis A of the funnel body 96h is nonlinear, such that the central axis along the enlarged introduction portion 171h is offset with regard to central axis along the narrowed cylindrical portion 172h, with a transition provided along tapered or funnel-shaped portion 173h. In this embodiment, the off-set funnel body 96h biases the shaft of the delivery device and hence the flexible-wing to the side of the funnel as illustrated. It may be advantageous for the funnel body 96h to be at a particular orientation relative to the implant 5 during loading.

Although the tapered geometry of the various funnel bodies described herein may in some examples be illustrated as being conical or of a constant taper angle, it should be understood that curved and/or irregular tapers may be provided in addition, or as an alternative, to the illustrated funnel bodies.

FIGS. 44 to 50 show a delivery sequence in accordance with exemplary embodiments of the present invention.

The delivery of the implant 5 starts with the procedural sheath 100 and guidewire 150 percutaneously positioned in situ.

The delivery sequence depends on which variant of loading funnel is used. For example, if any of the loading funnel shown in FIGS. 36 to 40B are used, then the first step may be to load the loading funnel onto the guidewire 150. If, for example, the loading funnel shown in FIGS. 41A to 42B is used then this step may be omitted. For simplicity the following sequence describes an exemplary delivery method using the loading funnel 95 shown in FIGS. 36 to 38.

Figure 44:
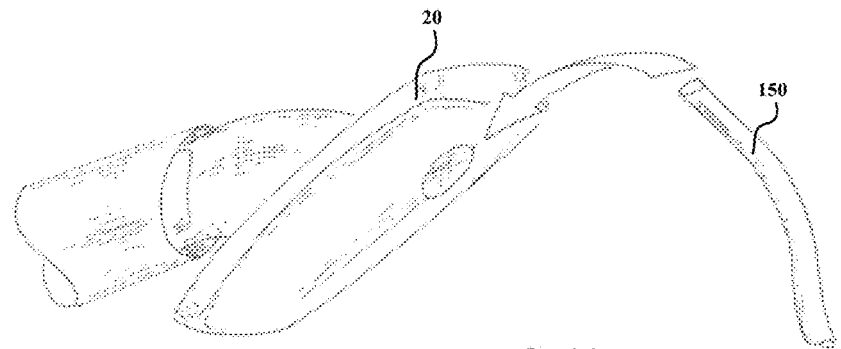
FIG. 44 shows a guidewire being back-loaded to the foot core of the closure device of FIG. 1A.

Step 1: Back load the guidewire 150 into the foot core 20 and the shaft 92 and handle 93 of the device 90. This step is generally illustrated in FIG. 44.

Figure 45A:
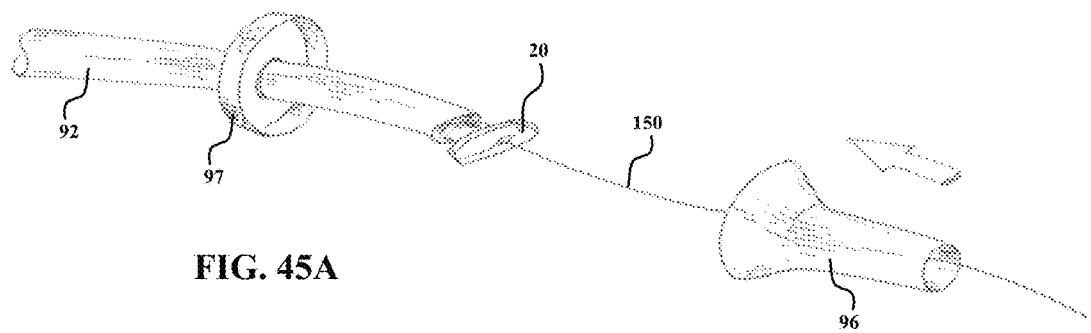
FIG. 45A shows insertion of the closure device of FIG. 1A being inserted into a loading funnel.
Figure 45B:
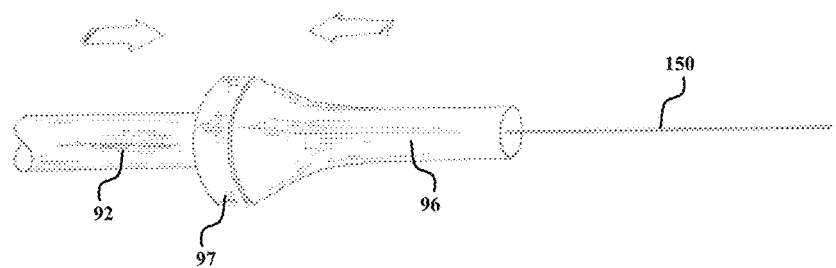
FIG. 45B shows a cap and seal snapped to a funnel body of the loading funnel of FIG. 45A.

Step 2: Insert the implant 5 into the funnel 96 to compress the flexible wing 60, and place the cap 97 and seal 98 (as well as retainer 99) onto the rear of loading funnel 96. This step is generally illustrated in FIGS. 45A and 45B.

Figure 46A:
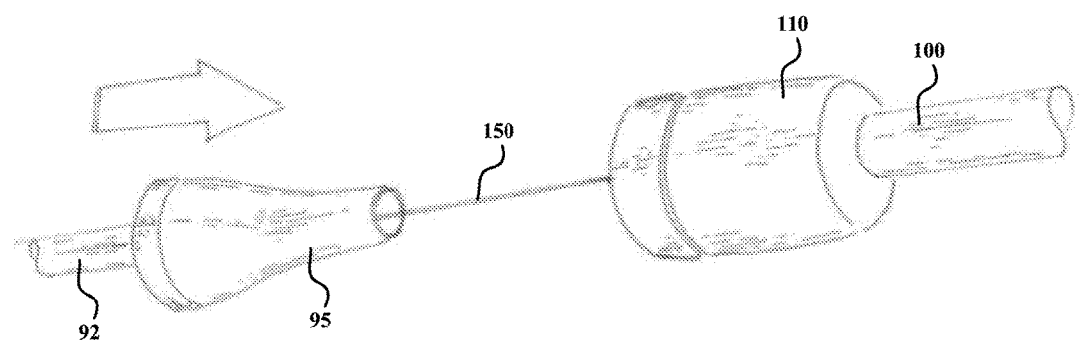
FIG. 46A shows a perspective view of the loading funnel of FIG. 45B, containing the closure device of FIG. 1A being inserted into a hub of the procedural sheath of FIG. 30.
Figure 46B:
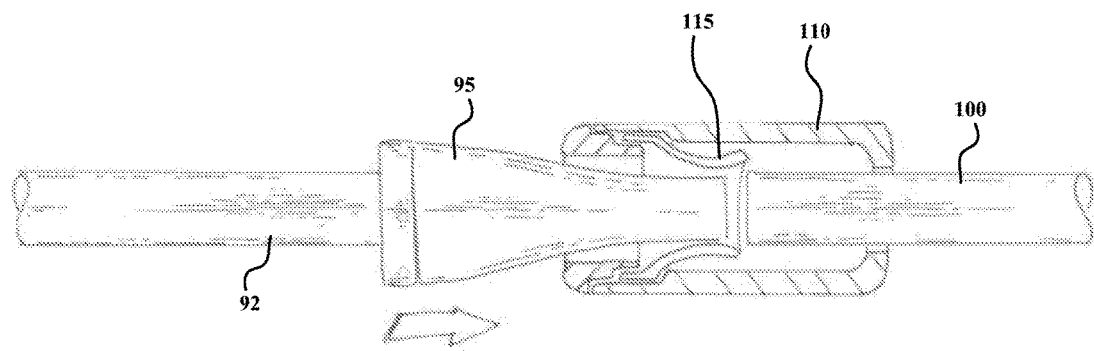
FIG. 46B shows a cross-sectional side view of the loading funnel of FIG. 45B, containing the closure device of FIG. 1A, inserted into the hub of the procedural sheath of FIG. 30.

Step 3: Insert the loading funnel 95 (and the other components of the device 90), which houses the implant 5, into the hub 110 and valve 115 at the rear of the procedural sheath 100. This step is generally illustrated in FIGS. 46A and 46B.

Figure 47A:
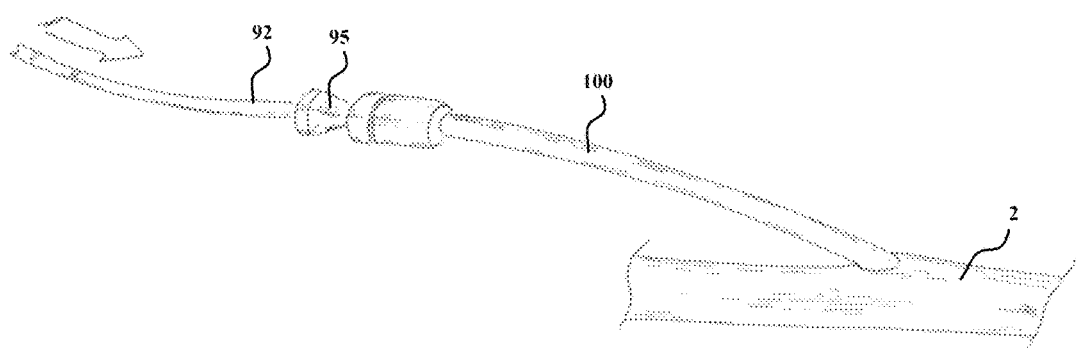
FIG. 47A shows advancement of the delivery system of FIG. 31A and the closure device of FIG. 1A down the procedural sheath of FIG. 30.
Figure 47B:
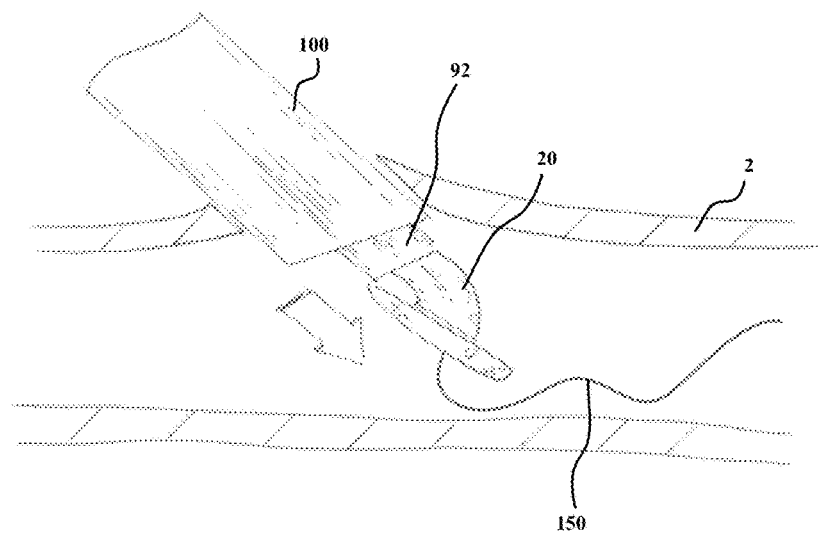
FIG. 47B shows advancement of the closure device of FIG. 1A and the distal portion of the delivery system of FIG. 31A into an arterial lumen.

Step 4: As illustrated in FIGS. 47A and 47B, the delivery device 90 and implant 5 are advanced down the procedural sheath 100 into the artery 2 to deliver the implant 5 into the arterial lumen (just distal to the procedural sheath tip) of the artery 2. Alternatively, the implant may be delivered into the arterial lumen by being advanced down the procedural sheath 100 into the artery 2 to deliver the implant 5 just proximal to the procedural sheath tip, then holding the delivery device 90 stationary (once the implant is positioned at the sheath tip) and withdrawing the sheath 100 over the delivery device 90 the required amount to expose the implant 5. This avoids pushing the exposed implant 5 upstream within the artery 2.

Figure 48:
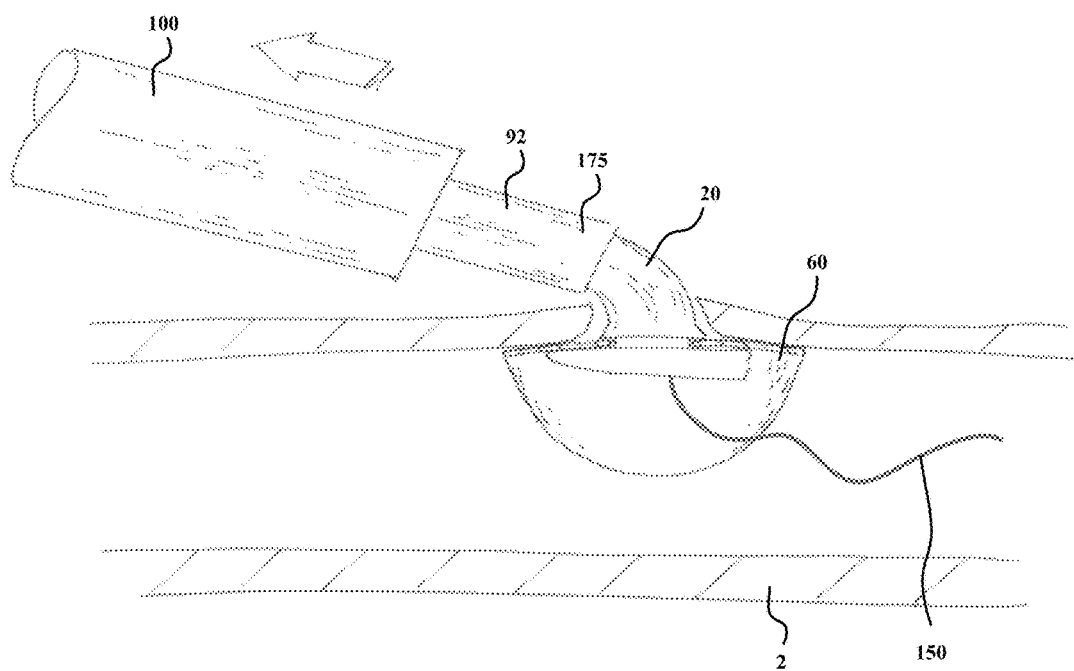
FIG. 48 shows the procedural sheath of FIG. 30 being withdrawn from the artery, with the artery shown in sectional side view.

Step 5: Withdraw the procedural sheath 100 from the artery 2 and position the implant 5 in juxtaposition to the arteriotomy. The implant 5 is now controlling the bleeding from the arteriotomy. This step is generally illustrated in FIG. 48.

Figure 49A:
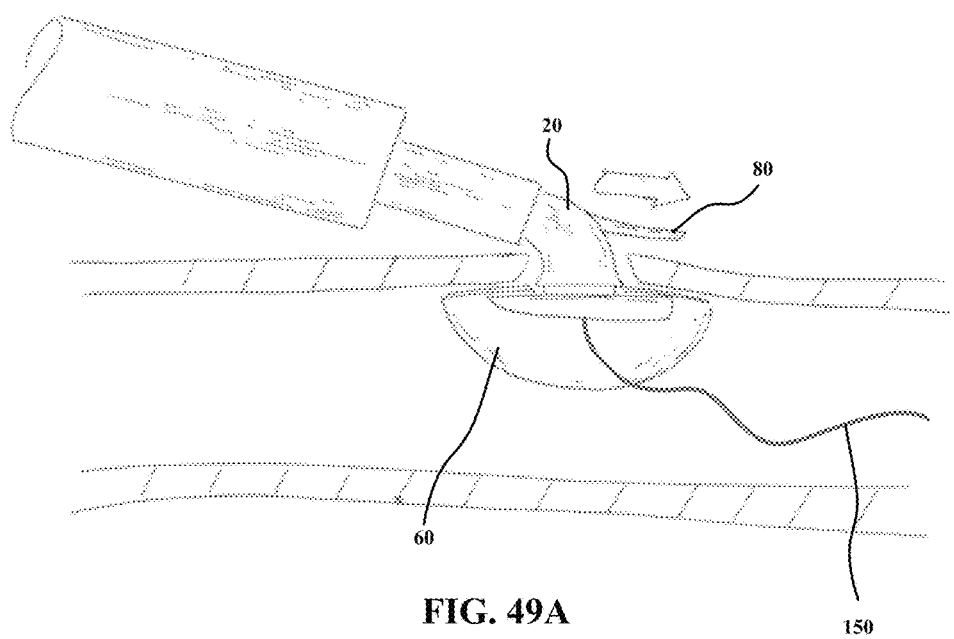
FIG. 49A shows the arrangement of FIG. 48 with deployment of the extra-luminal pin of the closure device.
Figure 49B:
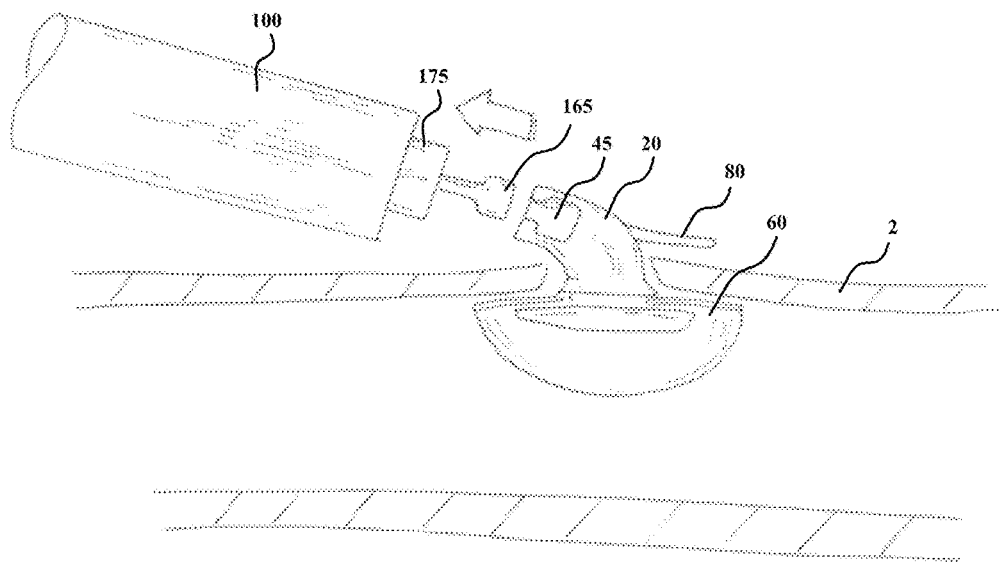
FIG. 49B shows the arrangement of FIG. 49A with the closure device released from the delivery system.

Step 6: Once confirmed that the implant 5 is correctly positioned and effecting a seal, the guidewire 150 is withdrawn, the extra-luminal pin 80 is deployed, and the implant is released. This step is generally illustrated in FIGS. 49A and 49B.

Figure 50:
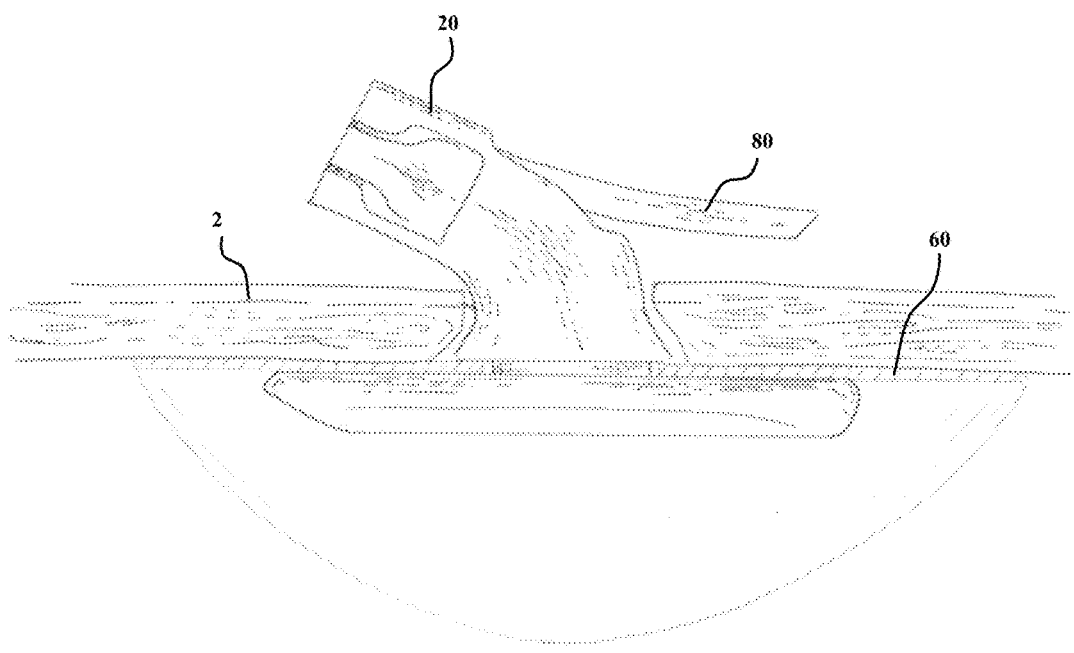
FIG. 50 shows the arrangement of FIG. 49B after withdrawal of the procedural sheath and delivery system from the tissue tract.

Step 7: Withdraw the procedural sheath 100 and delivery device 90 from the tissue tract to leave the implant (foot core 20, flexible wing 60, and extra-luminal pin 80) implanted to complete the delivery of the implant 5 and sealing of the arteriotomy. This step is generally illustrated in FIG. 50.

The above delivery sequence steps outline a method of implant deployment, there are many possible variants on this sequence to suit clinical requirements or preferences. For example, it may be advantageous to leave the guidewire 150 in situ through the implant after implant release, to maintain arterial percutaneous access, and remove the guidewire 150 when judged clinically appropriate. In this regard, it is noted that, as indicated above, in some embodiments, e.g. the version having extra-luminal pin 80a, the guide wire may remain in place even after deployment of the pin.

Figure 43J:
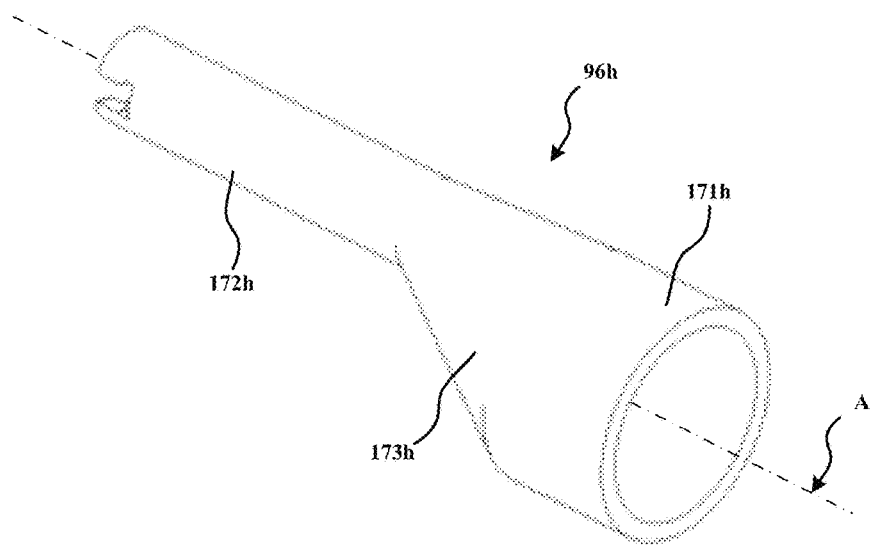
FIG. 43J shows a perspective view of an offset funnel body.
Figure 43K:
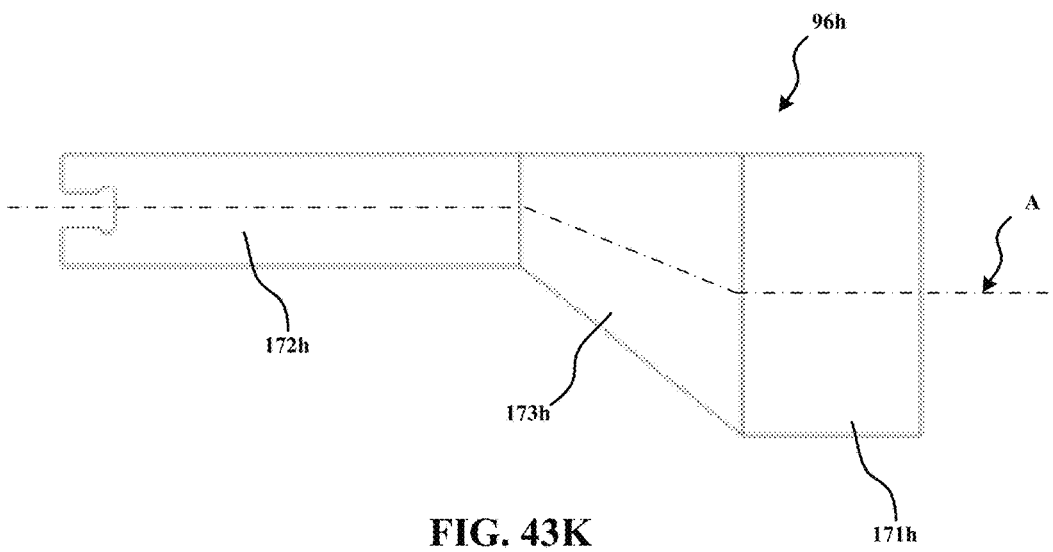
FIG. 43K shows a side view of the offset funnel body of FIG. 43J.
Figure 43L:
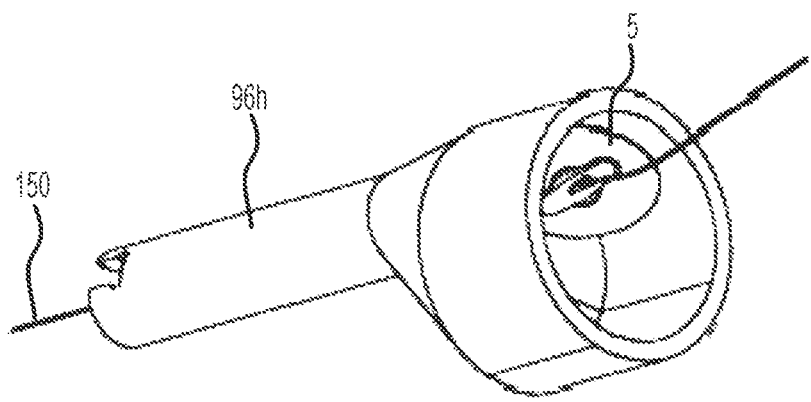
FIG. 43L shows a perspective view of the offset funnel body of FIG. 43J showing the relative position of an implant prior to loading along a guidewire
Figure 43M:
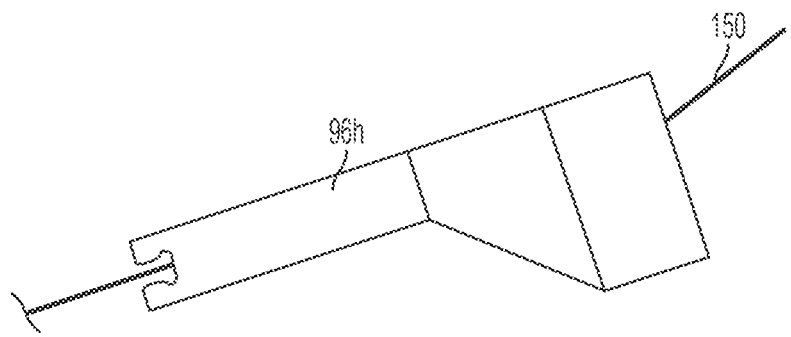
FIG. 43M shows a side view of the arrangement of FIG. 43L.
Figure 59:
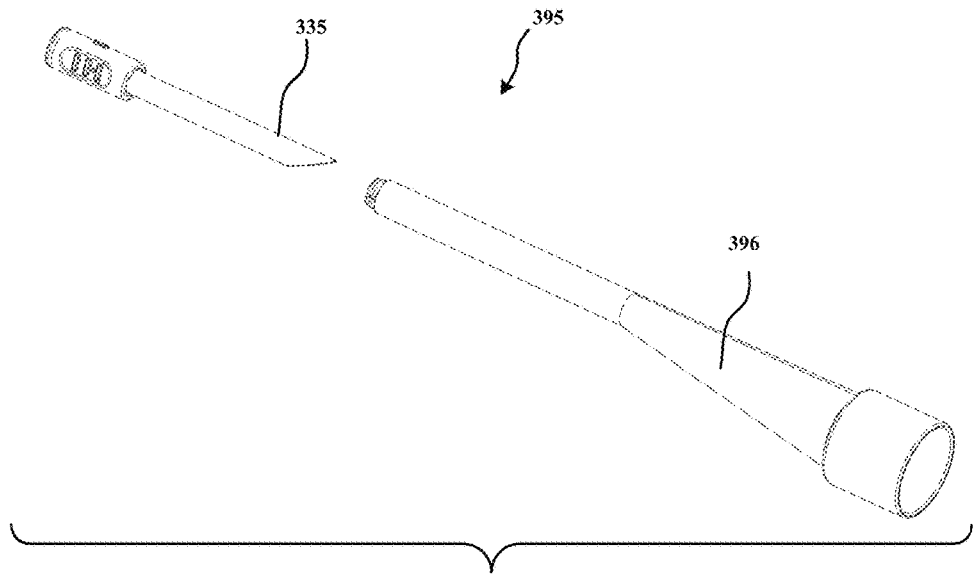
Figure 60:
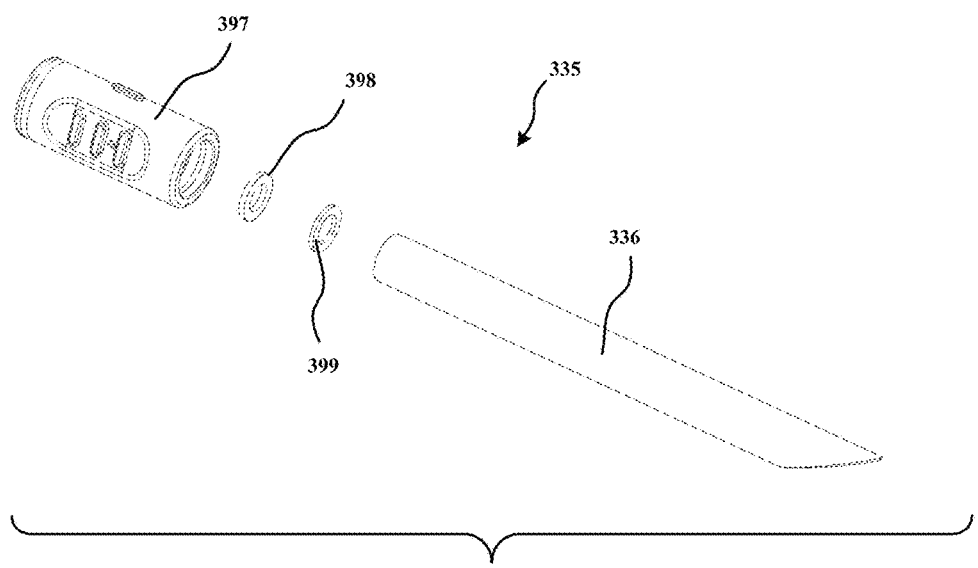

Referring to FIGS. 59 and 60, the loading funnel/cannula assembly 395 includes a loading cannula 335 and an offset loading funnel 396 analogous to the loading funnel 96h shown, for example, in FIG. 43J. Referring to the exploded view of FIG. 60, the cannula 335 includes a cannula tube 336, a cannula cap 397, a cannula seal 398, and a cannula seal retainer 399 that function in a manner analogous to other like components described herein, e.g. the components of the assembly illustrated, e.g. in FIG. 42B.

Closure Product and Packing

Figure 58:
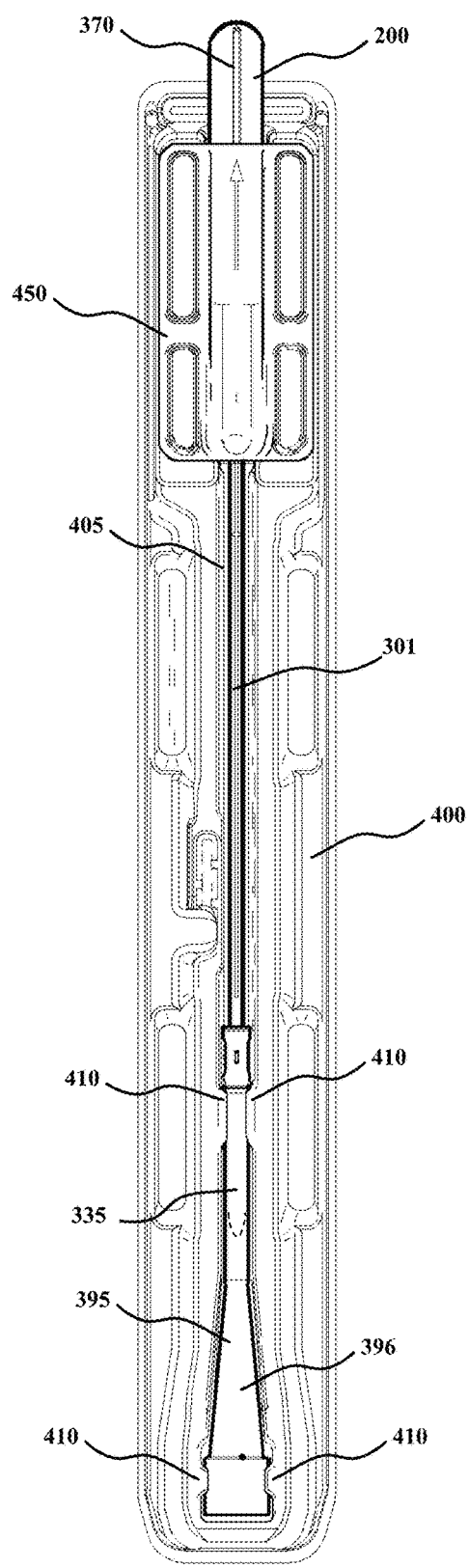

FIG. 58 shows a packaged product 300, that includes a surgical device 301 packaged in a protective tray 400. The surgical device 301 includes the same features of the other analogous example devices described herein, except to the extent indicated otherwise.

The surgical device 301 includes, inter alia, the handle 200 as described in additional detail herein, and a loading funnel/cannula assembly 395, which is analogous to other loading funnel/cannula arrangements described herein.

As illustrated in FIG. 58, the surgical device 301 is held in a recess 405 shaped to closely match the geometry of the surgical device 301 by tabs or projections 410.

The product 300 is configured such that the device 301 is removable from the tray 400 by proximally pulling the device 301 from the tray 400. In this example, the offset loading funnel 396 is retained in the tray as the remainder of the device 301 is withdrawn proximally from the tray.

To remove the device from the tray, the operator grips handle 200 protruding from the proximal end of the tray 400, e.g. between the thumb and fingers. While holding the tray 400 in the opposite hand or supporting the tray on a suitable surface for stability, the user may withdraw the device 301 proximally in a straight smooth continuous motion until the device 301 is completely free of the tray. Since the funnel 396 is retained in the tray 400 as the remainder of the device 301 is withdrawn, the implant 2 held by the device 301 moves proximally along the loading funnel/cannula assembly 395 such that the flexible wing of the implant 5 is folded by the funnel as the implant progresses toward the loading cannula 335. Upon further pulling the device 301, the implant 5 moves into the tube 336 of cannula 335, which maintains the folded configuration of the implant 5 until the implant 5 is deployed along the guidewire as described in further detail herein with regard to other examples.

Upon further retraction of the device 301, a positive stop engages between the loading cannula 335 and the shaft of the device 301, such that the cannula 335 is pulled away from and breaks free of the loading funnel 396. Upon further retraction of the device 301, the device 301 is freed from the tray, with the loading funnel 396 retained in the tray.

Figure 61:
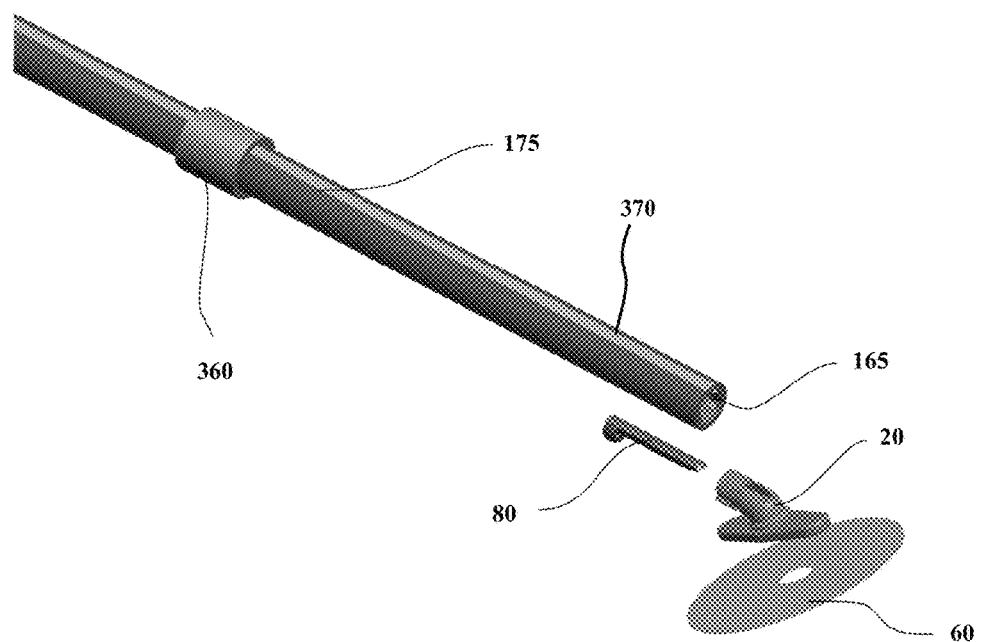

Referring to FIG. 61, the positive stop that engages between the cannula 335 and the shaft of the device 300 is formed between a loading cannula retaining ring 360 and the cap 397 of the cannula 335.

The device 300 includes an alignment mark 175 that extends longitudinally along the device 300 to provide a visual indication that the device 301 is properly rotated with respect to the tray 400 and the offset loading funnel 396 to ensure that the wing of the implant 5 is properly folded by the funnel 396. Geometric engagement of the device 301 with the tray 400 also facilitates this alignment. The alignment of the offset funnel 396 is facilitated by the geometry of the tray 400, the recess 405 of which is shaped to match the offset of the funnel 396 to thereby resist rotation of the funnel 396.

The tray 400 also includes a cover 450 that prevents inadvertent actuation of the lock member 240, thumb slider 250 or any other operable mechanism of the handle 300 while the device 301 is in the tray 400.

The tray 400 may provide a specific and defined atmosphere for storage of the implant pre- and post-sterilization, which may further add to increasing the post-sterilization shelf-life stability of the polymer from which the exemplary implant 5 is formed. One such mechanism is the use of a controlled atmosphere, specifically one where excessive moisture is reduced by means of use of a vacuum or low moisture containing dried gases such as nitrogen, argon, etc. Furthermore, the use of packaging materials with a low moisture vapor transmission rate, for example orientated polypropylene (OPP), Polyethylene terephthalate (PET), Linear low-density polyethylene (LLDPE), polyethylene (PE), foil-based packaging materials (e.g. aluminium), or combinations thereof, in combination with a low moisture environment can further aid in enhancing the stability of the polymeric material post-sterilization.

Figure 62:
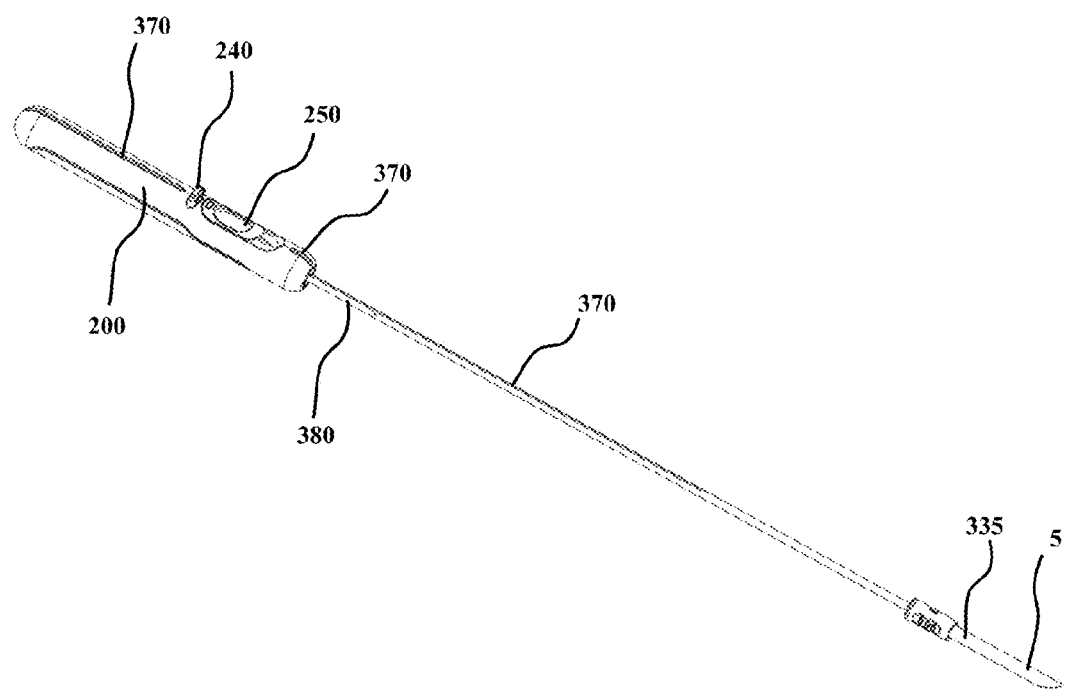

FIG. 62 shows the components of the device 301 once removed from the tray 400, with the implant 5 being folded and loaded into the loading cannula 335. The device 301 further includes an insertion mark 380 that provides the operator with a visual indication of how deep to insert the device 301 into the procedural sheath 100.

Although some example embodiments have been described herein in the context of vascular closure applications, it should be understood that the various mechanisms and concepts described herein are not limited to vascular applications and are applicable to any suitable applications that require closure of an aperture in a tissue.

Although the present invention has been described with reference to particular examples and exemplary embodiments, it should be understood that the foregoing description is in no manner limiting. Moreover, the features described herein may be used in any combination.

What is claimed is:

1. A device for sealing an aperture in a tissue, the device comprising:
    a foot including a distal portion configured to be disposed distally beyond a distal surface of the tissue when the device is in a sealing position, and a proximal portion having a longitudinal axis and configured to extend proximally through the aperture and proximally beyond a proximal surface of the tissue when the device is in the sealing position;

a thin flexible wing having at least one surface and a longitudinal plane, the thin flexible wing positionable against the distal surface of the tissue adjacent the aperture such that the thin flexible wing is disposed between the anterior distal portion of the foot and the distal surface of the tissue when the device is in the sealing position, wherein the at least one surface has a wettability that is increased from a base state of a material from which the thin flexible wing is formed; and an elongated retention member comprising a first portion and a second portion supported and housed by the proximal portion of the foot, the elongated retention member slideably moveable with respect to the proximal portion of the foot from a first position to a second position, wherein the elongated retention member, when in the first position is substantially straight with the first portion and the second portion aligned and extended substantially parallel to the longitudinal axis of the proximal portion of the foot, and wherein the elongated retention member, when in the second position is curved with the first portion substantially parallel to the longitudinal axis of the proximal portion of the foot and the second portion substantially parallel to the longitudinal plane of the thin flexible wing and positioned against the proximal surface of the tissue adjacent the aperture.

2. The device according to claim 1, wherein the device is configured to seal a surgical perforation in a cavity such as a gastrointestinal tract, heart, peritoneal cavity, esophagus, vagina, rectum, trachea, bronchi, or a blood vessel.

3. The device according to claim 1, wherein the device is configured to seal a surgical perforation in an artery, and the thin flexible wing is positionable against an internal luminal surface of the artery adjacent to the surgical perforation.

4. The device according to claim 1, wherein the foot is configured to provide support to the tissue in regions of the distal surface that surround the aperture.

5. The device according to claim 1, wherein the distal portion of the foot has an elongated shape.

6. The device according to claim 5, wherein the device is configured to seal a surgical perforation having a diameter that is less than a length of the distal portion of the foot.

7. The device according to claim 5, wherein the distal portion of the foot has two opposed lateral projections that extend outwardly from the longitudinal axis of the elongated shape.

8. The device according to claim 7, wherein the lateral projections are rounded.

9. The device according to claim 7, wherein the foot has a transverse width measured from an outer edge of one of the lateral projections to an outer edge of the other lateral projection that is constant along at least a portion of the lateral projections.

10. The device according to claim 1, wherein the distal portion of the foot is rectangular.

11. The device according to claim 1, wherein the distal portion of the foot is circular.

12. The device according to claim 1, wherein the device is comprises a recessed surface disposed in the distal portion of the foot and into which the thin flexible wing is received and crimped to provide an effective fluid seal between the wing and the distal portion of the foot.

13. The device according to claim 12, wherein the crimping of the thin flexible wing is achieved using at least one of (a) mechanical crimping, (b) chemical crimping, and (c) thermal crimping.

14. The device according to claim 1, further comprising a passageway extending through at least one of the foot and the thin flexible wing and configured to receive a guidewire therethrough, such that the entire device is freely movable along the guidewire.

15. The device according to claim 14, wherein the elongated retention member further comprises a closure member configured to move from the first position to the second position after complete removal of the guidewire, the movement of the closure member from the first position to the second position causing the passageway to be sealed.

16. The device according to claim 15, wherein the passageway includes an enlarged portion configured to maintain a seal via coagulation.

17. The device according to claim 16, wherein the enlarged portion is tapered.

18. The device according to claim 1, wherein at least one of the foot, the thin flexible wing, and the elongated retention member is formed at least in part of a material having an inherent viscosity in a range from 0.5 to 7.0 dl/g.

19. The device according to claim 1, wherein the longitudinal axis of the proximal portion of the foot is flexible with respect to a longitudinal axis of the distal portion of the foot.

20. The device according to claim 1, wherein the longitudinal axis of the proximal portion of the foot forms an angle in a range from 10 to 70 degrees with respect to a longitudinal axis of the distal portion of the foot.

21. The device according to claim 1, wherein the longitudinal axis of the proximal portion of the foot forms an angle of 30 degrees with respect to a proximal surface of the distal portion of the foot.

22. The device according to claim 1, wherein the distal portion of the foot has a length this is greater than a diameter of the aperture.

23. The device according to claim 1, wherein the proximal portion is flexible relative to the distal portion of the foot.

24. The device according to claim 1, wherein the distal portion of the foot is configured to reinforce the thin flexible wing to facilitate sealing of the aperture.

25. The device according to claim 1, wherein the elongated retention member is configured to provide a safety mechanism against the foot being fully pushed or pulled distally through the aperture.

26. The device according to claim 1, further comprising a guide channel configured to receive a guide wire.

27. The device according to claim 26, wherein the elonngated retention member is configured to block the guide channel when the elongated retention member is in the second position.

28. The device according to claim 26, wherein the elongated retention member is configured to leave the guide channel open when the elongated retention member is the first position.

29. A device for sealing an aperture in a tissue, the device comprising:

a foot including a distal portion configured to be disposed distally beyond a distal surface of the tissue when the device is in a sealing position, and a proximal portion having a longitudinal axis and configured to extend proximally through the aperture and proximally beyond a proximal surface of the tissue when the device is in the sealing position;

a thin flexible wing having at least one surface and a longitudinal plane, the thin flexible wing positionable against the distal surface of the tissue adjacent the aperture such that the thin flexible wing is disposed between the anterior distal portion of the foot and the distal surface of the tissue when the device is in the sealing position, wherein the at least one surface has a wettability that is increased from a base state of a material from which the thin flexible wing is formed; and an elongated retention member comprising a first portion and a second portion supported and housed by the proximal portion of the foot, the elongated retention member slideably moveable with respect to the proximal portion of the foot from a first position to a second position, wherein the elongated retention member, when in the first position is substantially straight with the first portion and the second portion aligned and extended substantially parallel to the longitudinal axis of the proximal portion of the foot, wherein the elongated retention member, when in the second position is curved with the first portion substantially parallel to the longitudinal axis of the proximal portion of the foot and the second portion substantially parallel to the longitudinal plane of the thin flexible wing and positioned against the proximal surface of the tissue adjacent the aperture, and wherein the device is formed of a polymer adapted to remain shelf stable and functional for sealing after terminal sterilization.

30. The device according to claim 29, wherein the polymer is adapted to remain shelf stable and functional for sealing after terminal sterilization using at least one of (a) ethylene oxide, (b) electron-beam, (c) gamma irradiation, and (d) nitrous oxide.

31. A device for sealing an aperture in a tissue, the device comprising:
a foot including a distal portion configured to be disposed distally beyond a distal surface of the tissue when the device is in a sealing position, and a proximal portion having a longitudinal axis and configured to extend proximally through the aperture and proximally beyond a proximal surface of the tissue when the device is in the sealing position;

a thin flexible wing having at least one surface and a longitudinal plane, the thin flexible wing positionable against the distal surface of the tissue adjacent the aperture such that the thin flexible wing is disposed between the anterior distal portion of the foot and the distal surface of the tissue when the device is in the sealing position, wherein the at least one surface has a wettability that is increased from a base state of a material from which the thin flexible wing is formed; and an elongated retention member comprising a first portion and a second portion supported and housed by the proximal portion of the foot, the elongated retention member slideably moveable with respect to the proximal portion of the foot from a first position to a second position, wherein the elongated retention member, when in the first position is substantially straight with the first portion and the second portion aligned and extended substantially parallel to the longitudinal axis of the proximal portion of the foot, wherein the elongated retention member, when in the second position is curved with the first portion substantially parallel to the longitudinal axis of the proximal portion of the foot and the second portion substantially parallel to the longitudinal plane of the thin flexible wing and positioned against the proximal surface of the tissue adjacent the aperture, and wherein at least one of the foot and the flexible wing, and the elongated retention member is formed at least in part of a polymer that is biodegradable.

32. The device according to claim 31, wherein the entire device is formed of a polymer that is biodegradable.

33. The device according to claim 31, wherein the polymer comprises Polydioxanone, Poly-L-lactide, Poly-D-lactide, Poly-DL-lactide, Polyglycolide, ε-Caprolactone, Polyethylene glycol, or combinations thereof.

34. The device according to claim 31, wherein the polymer comprises polydioxano

* * * * *

UNITED STATES PATENT AND TRADEMARK OFFICE
CERTIFICATE OF CORRECTION

| | |
|---|---|
| PATENT NO. | : 9,737,286 B2 |
| APPLICATION NO. | : 13/781628 |
| DATED | : August 22, 2017 |
| INVENTOR(S) | : Peter Grant et al. |

It is certified that error appears in the above-identified patent and that said Letters Patent is hereby corrected as shown below:

In the Claims

Column 34, Line 40-41 should read:
34. The device according to claim 31, wherein the polymer comprises polydioxanone.

Signed and Sealed this
Twenty-sixth Day of December, 2023

Katherine Kelly Vidal
*Director of the United States Patent and Trademark Office*